(12) United States Patent
Kaleta et al.

(10) Patent No.: US 12,133,796 B2
(45) Date of Patent: Nov. 5, 2024

(54) PROSTHETIC HEART VALVE WITH RADIOPAQUE ELEMENTS

(71) Applicant: St. Jude Medical, Cardiology Division, Inc., St. Paul, MN (US)

(72) Inventors: Richard Kaleta, Arden Hills, MN (US); Jay Reimer, Saint Paul, MN (US); Chad Joshua Green, Forest Lake, MN (US); Brandon Moore, St. Louis Park, MN (US); Ryan Finn, St. Paul, MN (US); Noy Grimmer, Woodbury, MN (US); Emily M. Hagen, Maple Grove, MN (US); Henrique Oliveira Neder, Gutierrez-Belo Horizonte (BR)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 249 days.

(21) Appl. No.: 17/314,706

(22) Filed: May 7, 2021

(65) Prior Publication Data

US 2021/0346154 A1 Nov. 11, 2021

Related U.S. Application Data

(60) Provisional application No. 63/021,934, filed on May 8, 2020.

(51) Int. Cl.
*A61F 2/24* (2006.01)

(52) U.S. Cl.
CPC .... *A61F 2/2418* (2013.01); *A61F 2220/0075* (2013.01); *A61F 2250/0098* (2013.01)

(58) Field of Classification Search
CPC ........................................................ A61F 2/24
See application file for complete search history.

(56) References Cited

U.S. PATENT DOCUMENTS

| | | | |
|---|---|---|---|
| 6,251,135 B1* | 6/2001 | Stinson | A61F 2/82 623/1.34 |
| 9,089,422 B2* | 7/2015 | Ryan | A61F 2/2436 |
| 9,744,034 B2 | 8/2017 | Braido et al. | |
| 10,052,200 B2 | 8/2018 | Chung et al. | |
| 2002/0099439 A1* | 7/2002 | Schwartz | A61F 2/2418 623/1.23 |

(Continued)

OTHER PUBLICATIONS

European Search Report for Application No. EP 21172904, dated Sep. 14, 2021, 9 pages.

*Primary Examiner* — Jacqueline Woznicki
(74) *Attorney, Agent, or Firm* — SLEMAN & LUND LLP

(57) ABSTRACT

A prosthetic heart valve includes a non-collapsible annular frame extending in a longitudinal direction between an inflow edge and an outflow edge, and a valve assembly connected to the frame. The frame includes a plurality of annularly spaced commissure posts adjacent the outflow edge, each of the commissure posts including a tip and a post slot spaced apart from the tip. The prosthetic heart valve further includes a radiopaque element including an elongated main body having a first end and a second end. The radiopaque element may extend around the tip and through the post slot of at least one of the commissure posts so that a portion of the main body extends between the slot and the tip. Alternatively or additionally, a radiopaque element may be positioned adjacent a base of the frame.

13 Claims, 41 Drawing Sheets

(56) References Cited

U.S. PATENT DOCUMENTS

| | | | |
|---|---|---|---|
| 2004/0167619 A1* | 8/2004 | Case | A61F 2/2418 623/1.34 |
| 2007/0027528 A1* | 2/2007 | Agnew | A61F 2/2475 623/2.18 |
| 2007/0244545 A1* | 10/2007 | Birdsall | A61F 2/2418 623/1.34 |
| 2009/0043373 A1* | 2/2009 | Arnault De La Menardiere | A61F 2/04 623/1.35 |
| 2009/0198315 A1* | 8/2009 | Boudjemline | D04C 3/48 623/1.2 |
| 2010/0049306 A1* | 2/2010 | House | A61F 2/2418 623/1.26 |
| 2011/0144690 A1* | 6/2011 | Bishop | A61F 2/2436 606/195 |
| 2012/0179033 A1* | 7/2012 | Merhi | A61F 2/013 604/529 |
| 2013/0166023 A1* | 6/2013 | Pipenhagen | A61F 2/2403 623/2.17 |
| 2013/0274872 A1 | 10/2013 | Vesely | |
| 2014/0188221 A1* | 7/2014 | Chung | A61F 2/2409 623/2.18 |
| 2014/0277389 A1* | 9/2014 | Braido | A61F 2/2418 623/1.26 |
| 2015/0073545 A1* | 3/2015 | Braido | A61F 2/2418 623/2.18 |
| 2015/0209136 A1* | 7/2015 | Braido | A61F 2/2418 623/2.18 |
| 2015/0209141 A1* | 7/2015 | Braido | A61F 2/2418 623/2.17 |
| 2015/0366664 A1* | 12/2015 | Guttenberg | A61F 2/2472 623/2.17 |
| 2017/0065408 A1* | 3/2017 | Grundeman | A61F 2/2412 |
| 2017/0189174 A1* | 7/2017 | Braido | A61F 2/2436 |
| 2017/0231761 A1* | 8/2017 | Cohen-Tzemach | A61F 2/2418 623/2.18 |
| 2018/0289471 A1* | 10/2018 | Schreck | A61L 31/18 |
| 2018/0289475 A1* | 10/2018 | Chung | A61F 2/2409 |
| 2018/0296335 A1* | 10/2018 | Miyashiro | A61F 2/2418 |
| 2019/0298968 A1* | 10/2019 | Morin | A61F 2/2418 |
| 2020/0188098 A1* | 6/2020 | Alkhatib | A61F 2/2418 |
| 2021/0251750 A1* | 8/2021 | Rumpca | A61F 2/2418 |
| 2021/0275298 A1* | 9/2021 | Peterson | A61F 2/9522 |
| 2021/0275299 A1* | 9/2021 | Peterson | A61F 2/2433 |
| 2021/0346154 A1* | 11/2021 | Kaleta | A61F 2/2418 |
| 2021/0401567 A1* | 12/2021 | Bachmaier | A61B 17/0401 |
| 2022/0039945 A1* | 2/2022 | Guttenberg | A61F 2/2472 |
| 2022/0061985 A1* | 3/2022 | Peterson | A61F 2/2418 |
| 2022/0175524 A1* | 6/2022 | Harewood | A61B 34/20 |

* cited by examiner

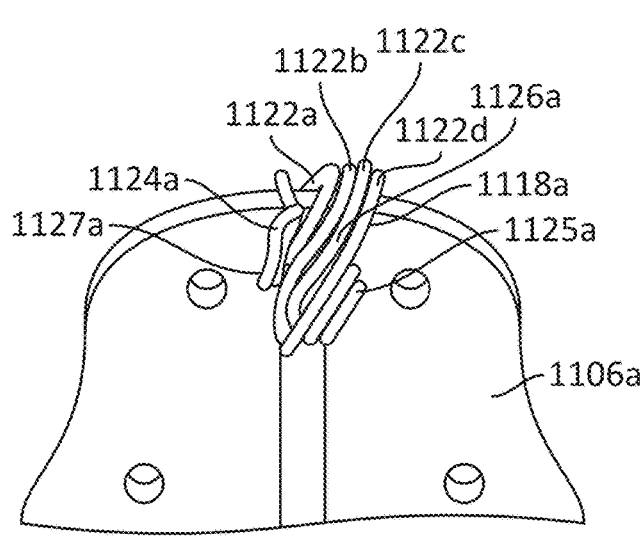 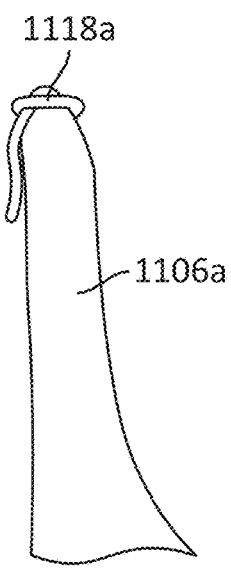
FIG. 4A  FIG. 4B
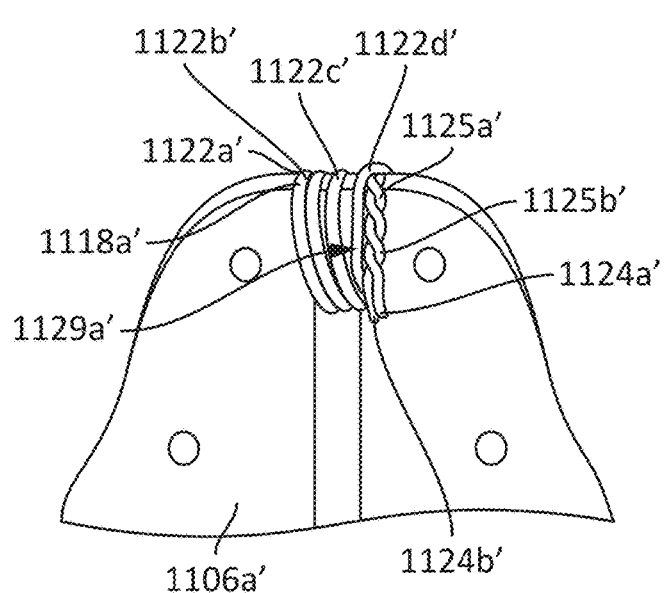 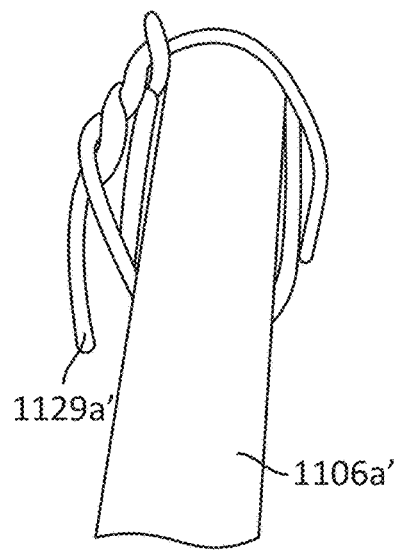
FIG. 5A  FIG. 5B

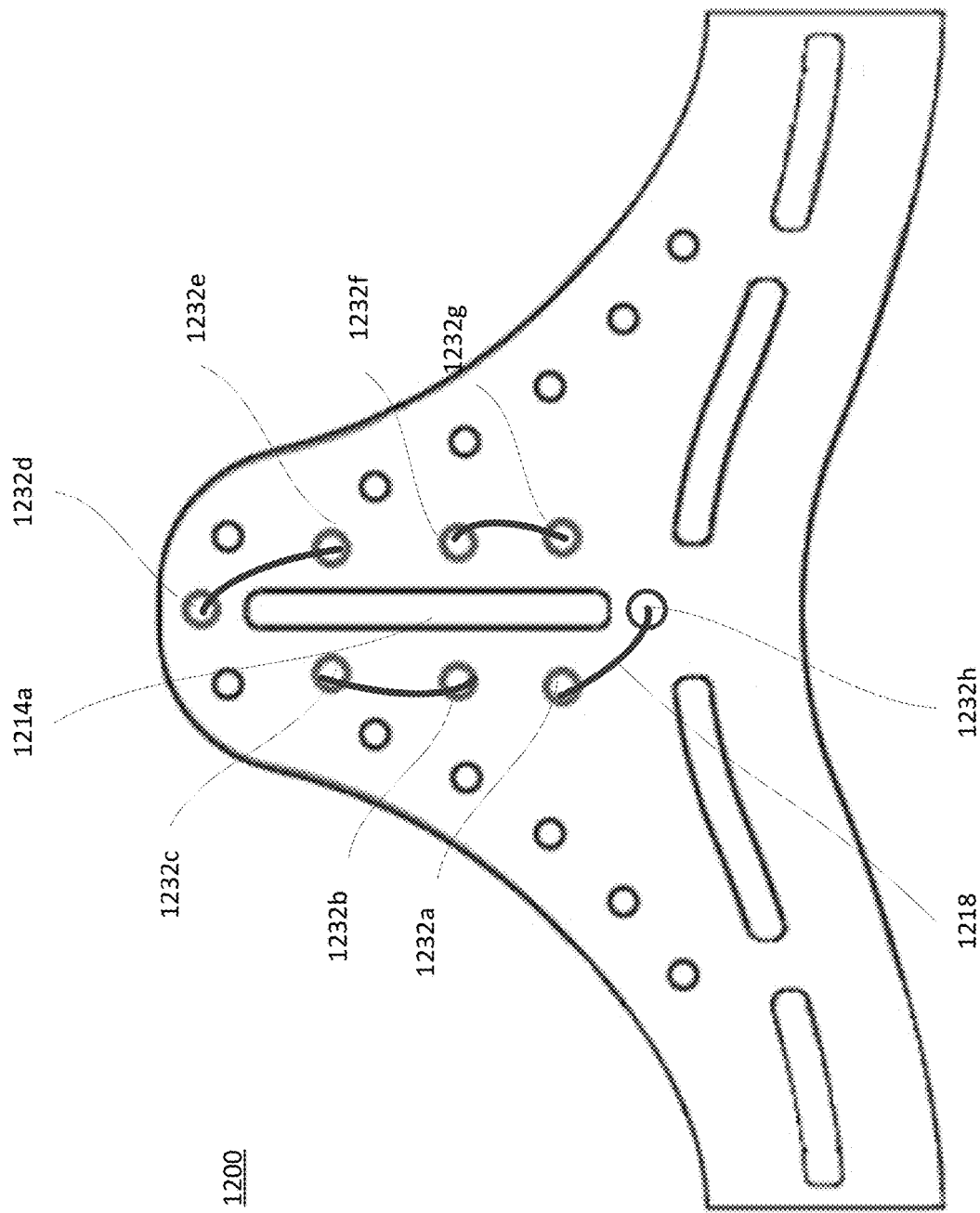

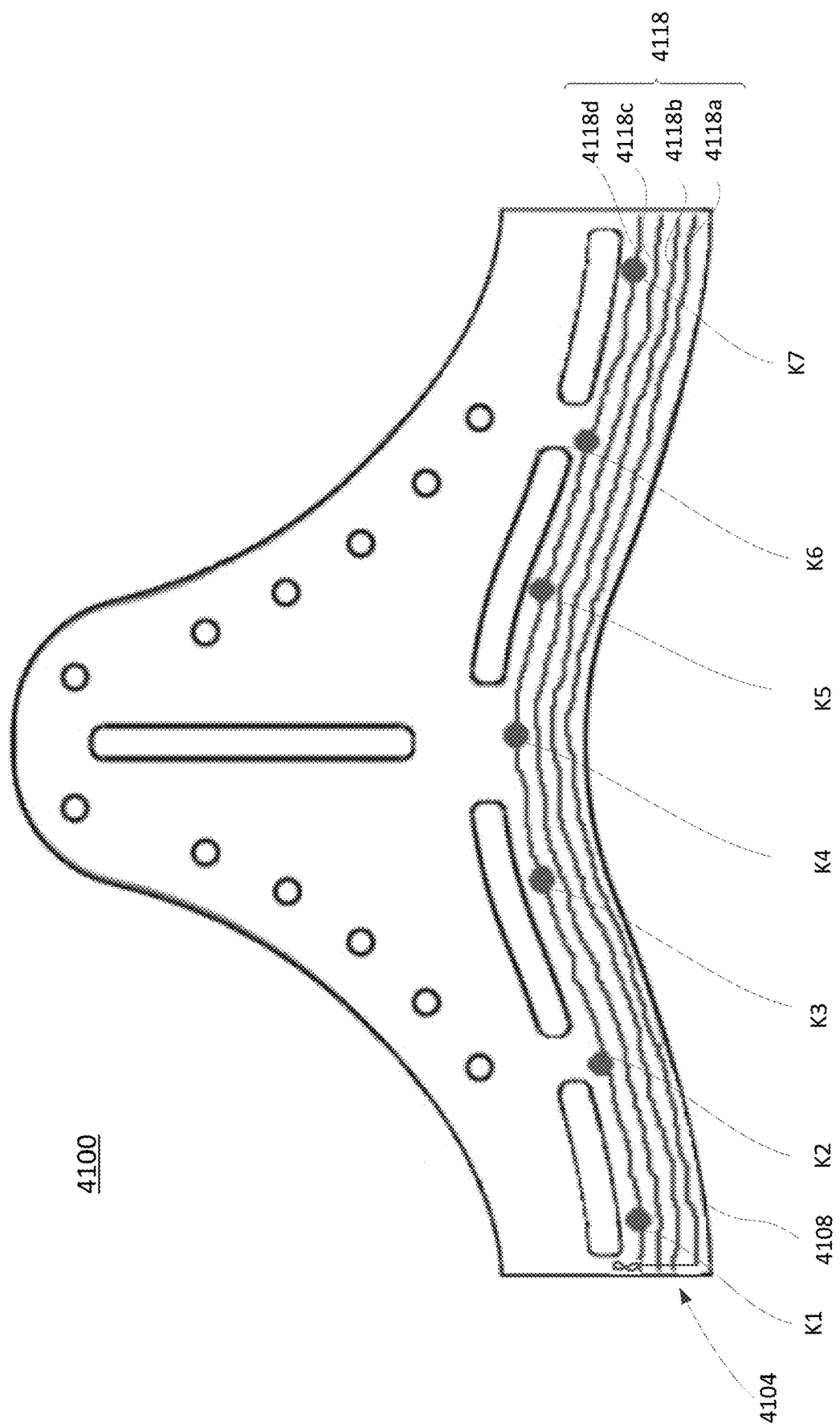

PROSTHETIC HEART VALVE WITH RADIOPAQUE ELEMENTS

CROSS-REFERENCE TO RELATED APPLICATIONS

This application claims the benefit of the filing date of U.S. Provisional Patent Application No. 63/021,934, filed May 8, 2020, the disclosure of which is hereby incorporated herein by reference.

BACKGROUND OF THE DISCLOSURE

The present disclosure relates in general to a heart valve for heart valve replacement and, in particular, to bioprosthetic heart valves. More particularly, the present disclosure relates to methods and devices for facilitating valve-in-valve implantation procedures using radiopaque elements.

BACKGROUND

When a native heart valve in an individual is diseased or damaged, a bioprosthetic heart valve may be surgically implanted in that individual to replace the native heart valve. At some time after the bioprosthetic heart valve has been successfully implanted and functioning within the individual, the implanted heart valve may become damaged or worn out such that it ceases to function properly. If the implanted heart valve fails to function properly, a new replacement prosthetic heart valve may be surgically implanted to resume normal functions. However, at the point at which the original implanted heart valve needs replacement, patients are often too old and frail for another invasive surgical procedure. For these patients, a less traumatic valve-in-valve procedure (hereinafter referred to as "VIV procedure") may be performed. In a VIV procedure, a new prosthetic heart valve is implanted inside of the surgical heart valve using a minimally invasive transcatheter procedure.

One challenge that arises from VIV procedures is that the diameter of the surgical heart valve limits the size of the transcatheter heart valve that can be implanted inside of it. When the originally implanted surgical heart valve is small (e.g., 19 or 21 millimeters in diameter), the size of the implanted transcatheter heart valve may be too small to meet the patient's blood flow requirements, such that the patient suffers from suboptimal hemodynamics. This results in the phenomenon of patient-prosthesis mismatch (hereinafter referred to as "PPM"). PPM has shown to be associated with increased mortality after VIV procedures.

PPM also occurs when patients do not know the size of the valve currently in their body. Given that the lifetime of a surgical valve can be anywhere from 10-20 years, records may have been lost or misplaced within that time period. Implantation of an inappropriately large transcatheter heart valve may result in stent deformation, valvular incompetence, and/or damage to the surrounding tissues. On the other hand, use of an inappropriately small transcatheter heart valve may result in suboptimal hemodynamics. Without knowledge of the exact size of the surgical valve within the patient's body, the physician will have difficulty determining the best size of transcatheter heart valve to replace the surgical valve. A physician will have to make a best estimate about the size of the surgical valve primarily based on the x-rays.

Another challenge presented with VIV procedures is determining the exact position and orientation of the deteriorated surgical valve prior to insertion of the replacement valve. In order to properly position the transcatheter valve within the deteriorated surgical valve, the surgeon must rely on x-rays or fluoroscopy to identify the current position of the surgical valve and the target site for implantation of the transcatheter heart valve.

Thus, knowing the position of the surgical valve within the body prior to the VIV procedure, as well as the size of the valve, is paramount. Current procedures for determining valve position include placing a single wrap of a stainless steel wire around an annular section of the stent which is within the valve cuff. The physician may identify this wire using x-rays/fluoroscopy. (See FIG. 1.) This structure can be insufficient to aid the physician because the wire may not clearly appear on x-rays/fluoroscopy. Additionally, the annular wire interferes with VIV procedures that involve cracking the surgical valve stent prior to inserting the transcatheter valve. Thus, there exists a need for improved devices and methods to aid physicians with identifying the position of a deteriorated surgical valve within a patient's body, as well as with determining the size of the deteriorated valve.

BRIEF SUMMARY

According to a first embodiment of the present disclosure, a prosthetic heart valve includes a non-collapsible annular frame extending in a longitudinal direction between an inflow edge and an outflow edge. The frame has a plurality of annularly spaced commissure posts adjacent the outflow edge. A flow direction through the frame extends from the inflow edge toward the outflow edge. A radiopaque element includes an elongated main body having a first end and a second opposed end and extends around the tip and through the opening of at least one of the commissure posts so that at least a portion of the main body extends between the opening and the tip. A valve assembly is connected to the frame and includes a plurality of leaflets.

According to a second embodiment of the present disclosure, a prosthetic heart valve includes a non-collapsible annular frame extending in a longitudinal direction between an inflow edge and an outflow edge. The frame includes a plurality of annularly spaced commissure posts adjacent the outflow edge, each of the commissure posts including a tip and a post slot spaced apart from the tip. The frame further includes a radiopaque element including an elongated main body having a first end and a second end. The radiopaque element may extend around the tip and through the post slot of at least one of the commissure posts so that a portion of the main body extends between the slot and the tip. A radiopaque element may extend around a base of the frame. A valve assembly may be connected to the frame and may include a plurality of leaflets.

According to a third embodiment of the present disclosure, a heart valve includes a non-collapsible annular frame extending in a longitudinal direction between an inflow edge and an outflow edge. The frame has a plurality of annularly spaced commissure posts adjacent the outflow edge. Each of the commissure posts has a tip and a post slot spaced apart from the tip, the frame including a plurality of apertures. A radiopaque wire extends through at least one of the plurality of apertures. The valve assembly is connected to the frame and includes a plurality of leaflets.

According to a fourth embodiment of the present disclosure, a prosthetic heart valve includes a non-collapsible annular frame extending in a longitudinal direction between an inflow edge and an outflow edge. The frame has an annular base and a plurality of annularly spaced commissure posts adjacent the outflow edge. Each of the commissure posts has a tip and a post slot spaced apart from the tip. A radiopaque wire extends a plurality of revolutions around the base so as to form a first wire wrap and a second wire wrap. A valve assembly may be connected to the frame and include a plurality of leaflets.

According to a fifth embodiment of the present disclosure, a prosthetic heart valve includes a non-collapsible annular frame extending in a longitudinal direction between an inflow edge and an outflow edge. The frame has an annular base and a plurality of annularly spaced commissure posts adjacent the outflow edge. Each of the commissure posts has a tip and a post slot spaced apart from the tip. A radiopaque wire extends at least partially around the base so as to form a first wire wrap and a second wire wrap. A valve assembly may be connected to the frame and include a plurality of leaflets.

According to a sixth embodiment of the present disclosure, a prosthetic heart valve includes a non-collapsible annular frame extending in a longitudinal direction between an inflow edge and an outflow edge. The frame has a plurality of annularly spaced commissure posts adjacent the outflow edge, and each of the commissure posts has a tip and a post slot spaced apart from the tip. A radiopaque wire extends around a base of the frame and has one or more radiopaque indicators indicating a size of the frame. The valve assembly is connected to the frame and including a plurality of leaflets.

According to a seventh embodiment of the disclosure, a prosthetic heart valve includes a non-collapsible annular frame extending in a longitudinal direction between an inflow edge and an outflow edge, a radiopaque wire, and a valve assembly. The frame has an annular base and a plurality of annularly spaced commissure posts adjacent the outflow edge. Each of the commissure posts have a tip and a post slot spaced apart from the tip. The radiopaque wire extends partially around the base and forms a first wire wrap and a second wire wrap. The radiopaque wire has a first looped end and a second looped end spaced apart from the first looped end. The first looped end can be secured to the second looped end by a suture. The valve assembly is connected to the frame and includes a plurality of leaflets.

According to an eight embodiment of the disclosure, a prosthetic heart valve comprises a non-collapsible annular frame, a radiopaque element and a valve assembly. The frame extends in a longitudinal direction between an inflow edge and an outflow edge. The frame has a plurality of annularly spaced commissure posts adjacent the outflow edge, each of the commissure posts having a tip and a post slot spaced apart from the tip. The radiopaque element include an elongated main body that has a first end and a second end. The valve assembly is connected to the frame and includes a plurality of leaflets.

It is to be noted that the features of the above-described arrangements are not exclusive to each other, and that any one of such features and arrangements can be combined with one or more of the other features and arrangements to arrive at further aspects of the disclosure.

BRIEF DESCRIPTION OF THE DRAWINGS

A more complete appreciation of the subject matter of the present disclosure may be realized by reference to the following detailed description and the accompanying drawings, in which:

FIG. 4A is an enlarged fragmentary view of the frame shown in FIGS. 3A and 3B;

FIG. 4B is a side view of what is shown in FIG. 4A;

FIG. 5A is an enlarged fragmentary view of an alternate embodiment of the frame shown in FIGS. 3A and 3B;

FIG. 5B is a side view of what is shown in FIG. 5A;

FIG. 9A is a fragmentary front view of a one-third section of the frame of FIG. 8;

FIG. 25 is a view similar to FIG. 10 according to another embodiment thereof;

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the circumferential direction refers to the direction extending along the circumference of the prosthetic heart valve.

Figure 1A:
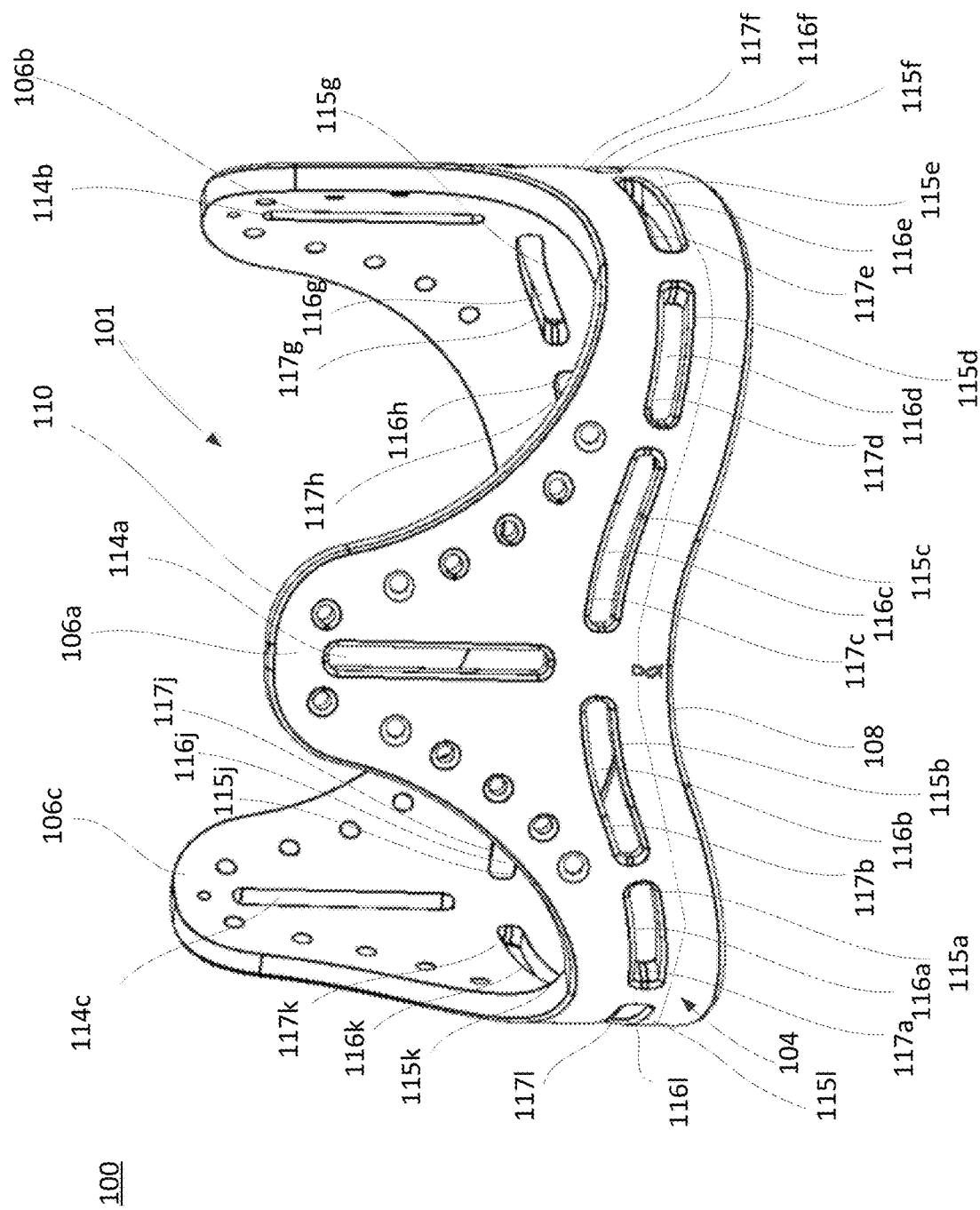
FIG. 1A is a perspective view of the frame of a prior art surgical heart valve.

FIG. 1A is a perspective view of a frame 100 for a prosthetic heart valve according to the prior art. Frame 100 is a component of a surgical heart valve, i.e., a prosthetic heart valve that is implanted in a patient through open chest, open heart surgery. Generally, certain embodiments of the present disclosure include frames similar to frame 100, although each embodiment includes a different structural radiopaque feature that enables one to view the exact location of the commissure posts and/or annulus of the frame, in vivo, as will be described in further detail below. The ability to identify the exact location of the frame's commissure posts and/or annulus, as well as determine the size of the already-implanted valve, enables a more precise selection of a replacement transcatheter valve prior to a VIV procedure, as well as the implantation of the transcatheter valve within the surgical heart valve during a VIV procedure.

Referring to FIG. 1A, frame 100 is a hollow, non-collapsible annular stent-like structure. Frame 100 is referred to as "hollow" because the interior region 101 that is bounded by the annular structure is open. Frame 100 is typically made of an acetal copolymer material, including polyetheretherketone or acetal. The copolymer frame may be manufactured by injection molding, but other methods of manufacturing may be utilized, including machining and laser cutting a plastic tube or the like.

Figure 1B:
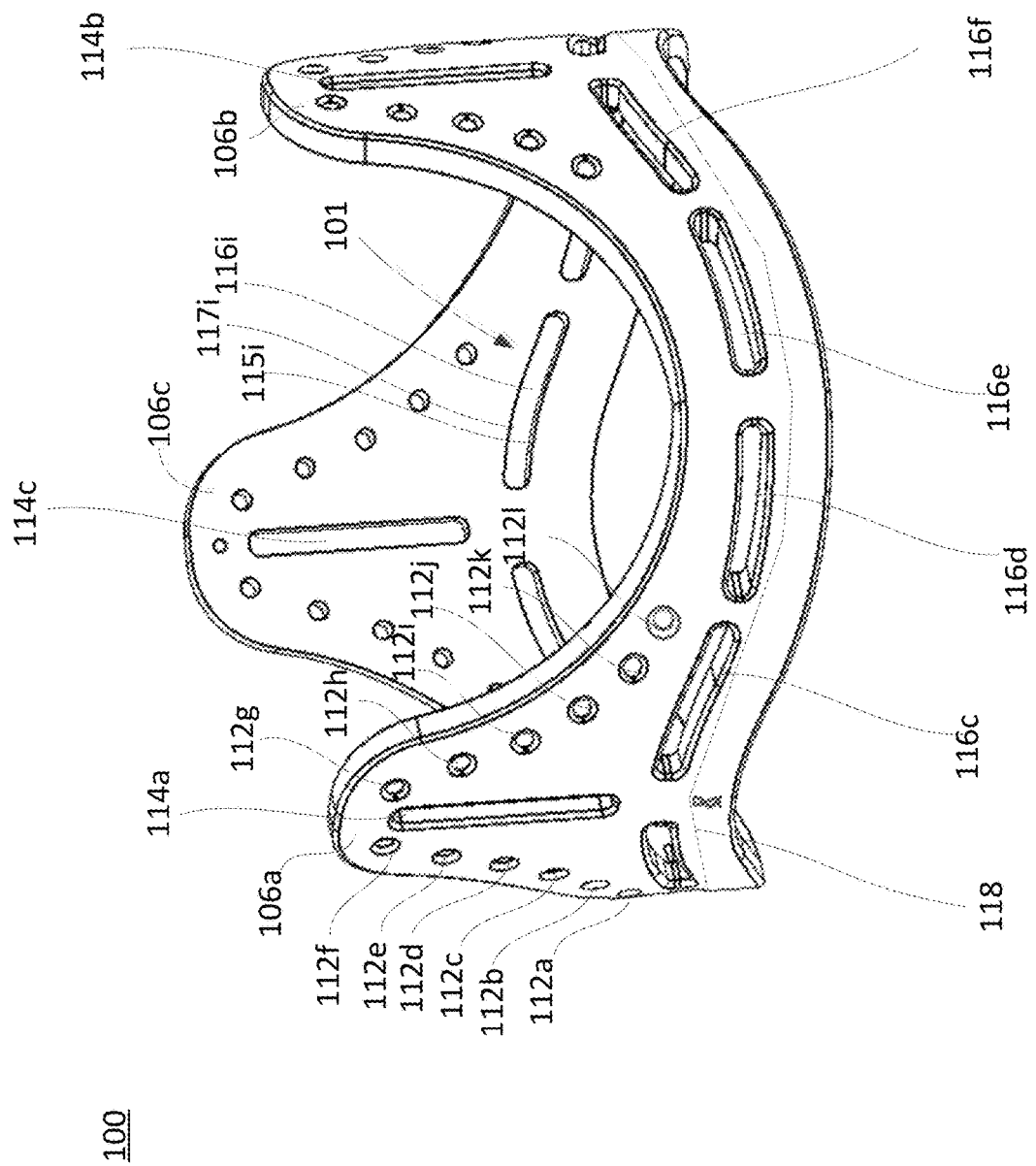
FIG. 1B is another perspective view of the frame in FIG. 1A.
Figure 1C:
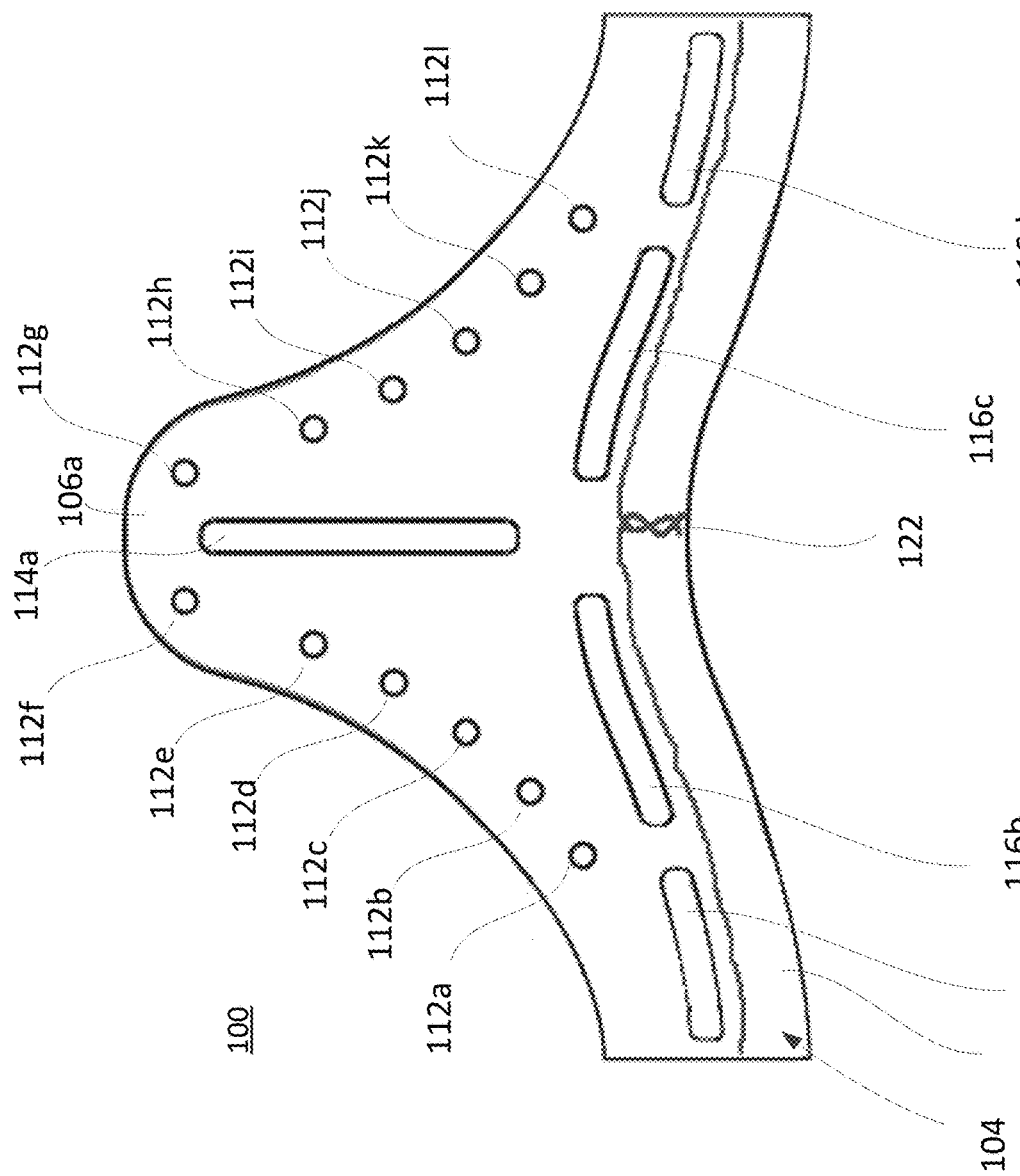
FIG. 1C is a one third section of the frame of FIG. 1A.

Because the surgical heart valve being discussed is a tricuspid valve (e.g., for use in replacing a patient's aortic valve), frame 100 has three commissure posts 106a, 106b, and 106c that may be equally spaced from one another around the circumference of the frame. Each commissure post stands up from the annularly continuous base 104 of the frame. The base includes a lower-most, blood-inflow edge 108. As used throughout the present description, the terms lower, below, upper, above, bottom and top refer to a frame oriented as shown in FIGS. 1A, 1B, 1C, with FIG. 1C representing a one-third portion only of frame 100. Inflow edge 108 may be scalloped as one proceeds around the frame to approximately match the natural scallop of the native valve annulus. In particular, the scallop of inflow edge 108 may rise in the vicinity of each commissure post 106, and may fall between each annularly adjacent pair of commissure posts.

Frame 100 also includes an annularly continuous blood-outflow edge 110 (which merges with and becomes part of each commissure post 106). Outflow edge 110 may be much more deeply scalloped than inflow edge 108. In particular, outflow edge 110 rises adjacent each commissure post 106 (actually merging into each commissure post), and falls between each annularly adjacent pair of commissure posts.

Inflow edge 108, outflow edge 110, and the flexibility of frame 100 are designed to help ensure proper opening and coaptation of the finished valve in use. (Coaptation is the coming together of the free edges of the valve leaflets when the valve is closed.) Frame 100 is further designed to decrease maximum stresses in the frame during use, which gives the finished valve an increased safety factor.

A plurality of openings in the form of apertures and slots may be present in frame 100, at least some of which may be used to attach fabric and/or tissue over frame 100. The apertures and slots may be used to pass needles through frame 100 when attaching the fabric and/or tissue to the frame, as discussed in connection with FIG. 2. The apertures may extend along the outflow edge of each of the commissure posts 106a, 106b, 106c. For example, apertures 112a-1121 are shown adjacent outflow edge 110 of commissure post 106a in FIGS. 1B-1C.

Geometric openings are also provided within frame 100 in order to increase the flexibility of the frame and withstand fatigue, particularly as the valve leaflets open and close during use. As shown in FIGS. 1A-1B, a plurality of base openings 116a, 116b, 116c, 116d, 116e, 116f, 116g, 116h, 116i, 116j, 116k, 116 extend around the base 104 of frame 100. The base openings may be provided between each pair of adjacent commissure posts 106. For example, four base openings 116c, 116d, 116e, 116f may extend between commissure posts 106a and 106b. Each base opening includes a respective bottom edge 115a-1151 and a respective top edge 117a-1171. Bottom edges 115 may extend generally parallel to inflow edge 108. Commissure posts 106a-106c may further include respective post slots 114a-114c that extend along the length of the respective commissure posts.

As shown, an annular wire 118 may extend around the base 104 of frame 100, and its ends may be tied off with a twist 122. As shown in FIG. 1C, the ends of annular wire 118 may be intertwined or twisted together. Twist 122 may appear at any position along base 104, depending on where the wrapping of annular wire 118 begins and ends. In the example shown, twist 122 is at the same position as the commissure post 114a.

Figure 2:
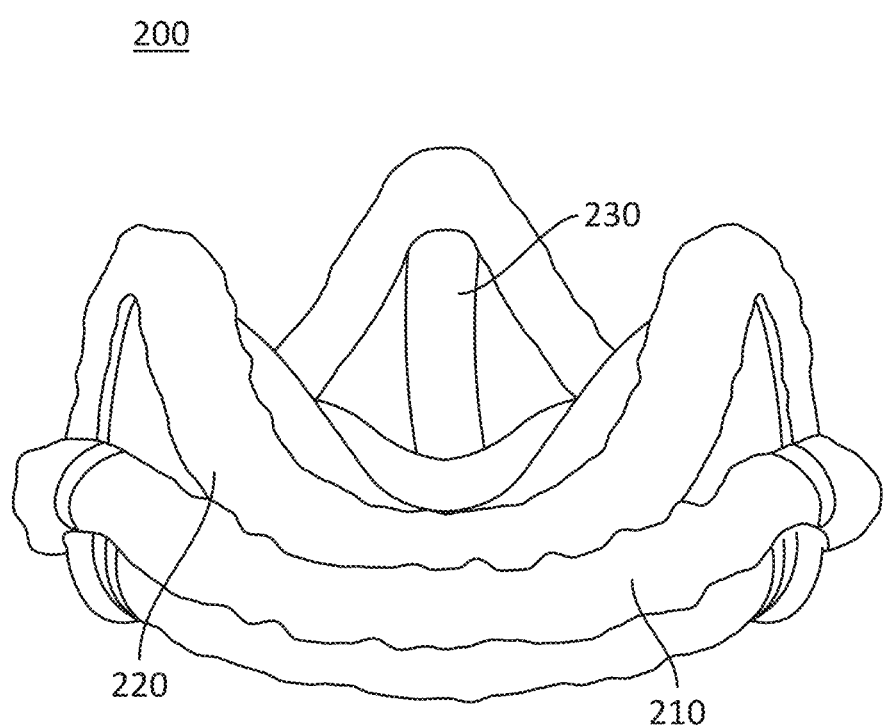
FIG. 2 is a perspective view of an embodiment of a surgical heart valve of the prior art.

FIG. 2 illustrates a prior art surgical heart valve 200 formed from frame 100. Surgical heart valve 200 may include a sewing cuff 210 that extends around base 104 and overlies annular wire 118, as well as one or more layers of fabric and/or biological tissue covering the sewing cuff and frame 100. For example, a ring (not shown) formed of silicone or another appropriate material may be positioned around the outside of base 104 and may follow the scalloping of inflow edge 108. A layer of fabric (not shown) may then be applied tightly over the inside surface of frame 100, over the outside surface of the frame, and around the exposed surfaces of the ring so that the fabric layer conforms to the outflow edge 110 of the frame. Sutures may be used to hold the fabric layer to the underlying structures.

Optionally, a fabric sleeve (not shown) may be sutured or otherwise attached to cover the top of each commissure post 106 prior to the application of the fabric layer. These fabric sleeves may help reduce the possibility that the tips of the commissure posts will poke through the fabric layer or any subsequently applied layers.

A layer of biological tissue 220 may then be applied over the fabric layer both inside and outside of frame 100 and may attach to the fabric-covered ring. The biological tissue may be mammalian pericardial tissue, such as bovine, porcine or equine pericardium, or other appropriate types of tissue. The tissue layer may be secured to the underlying structure by sutures. Additional tissue, preferably of the same type, may be cut to shape and assembled to the interior of the covered frame to form leaflets 230. Alternatively, leaflets 230 can be formed from animal leaflets, including a bovine cusp or porcine cusp. The lower edges of the leaflets may follow the scalloped shape of inflow edge 108. All three leaflets shown in FIG. 2 may be formed from a single integral sheet of tissue. Rather than biological tissue, leaflets 230 and the outer covering of surgical heart valve 200 may be formed from a biocompatible polymer, or from a tissue/polymer combination. The various layers that may be applied to frame 100 to form surgical heart valve 200 are more fully described in U.S. Pat. No. 9,510,944, the disclosure of which is hereby incorporated by reference herein.

The surgical heart valves in accordance with a first embodiment of the present disclosure may be similar to heart valve 200 described above, and may include the same fabric, tissue and/or polymer leaflets and covering layers, but may be modified to include features that allow for portions of the valve to be more easily seen and identified on an x-ray/fluoroscopy before and during a VIV procedure.

Radiopaque Elements on One or More Commissure Posts

Figure 3A:
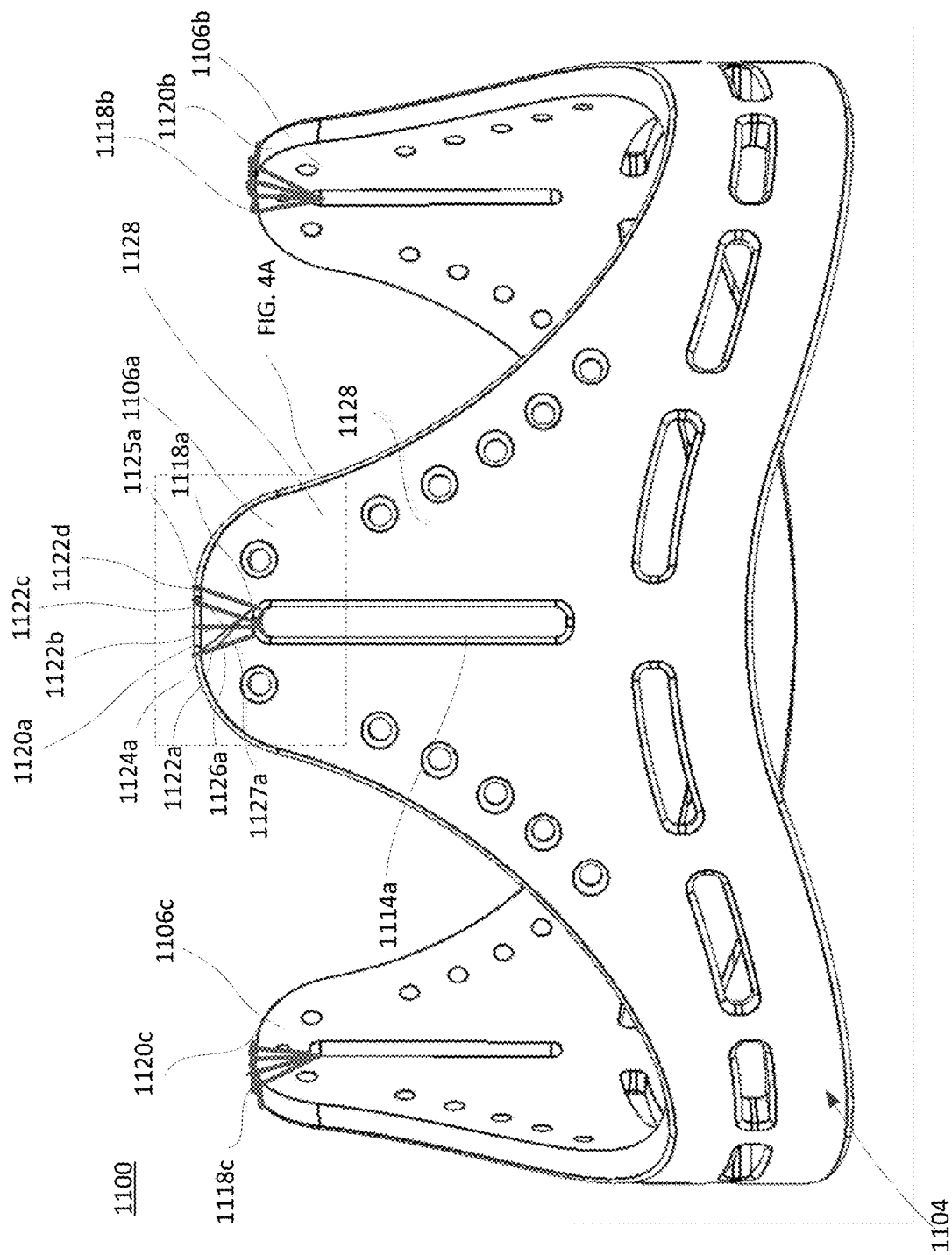
FIG. 3A is a front elevational view of the frame of a surgical heart valve having radiopaque elements according to an embodiment of the present disclosure.
Figure 3B:
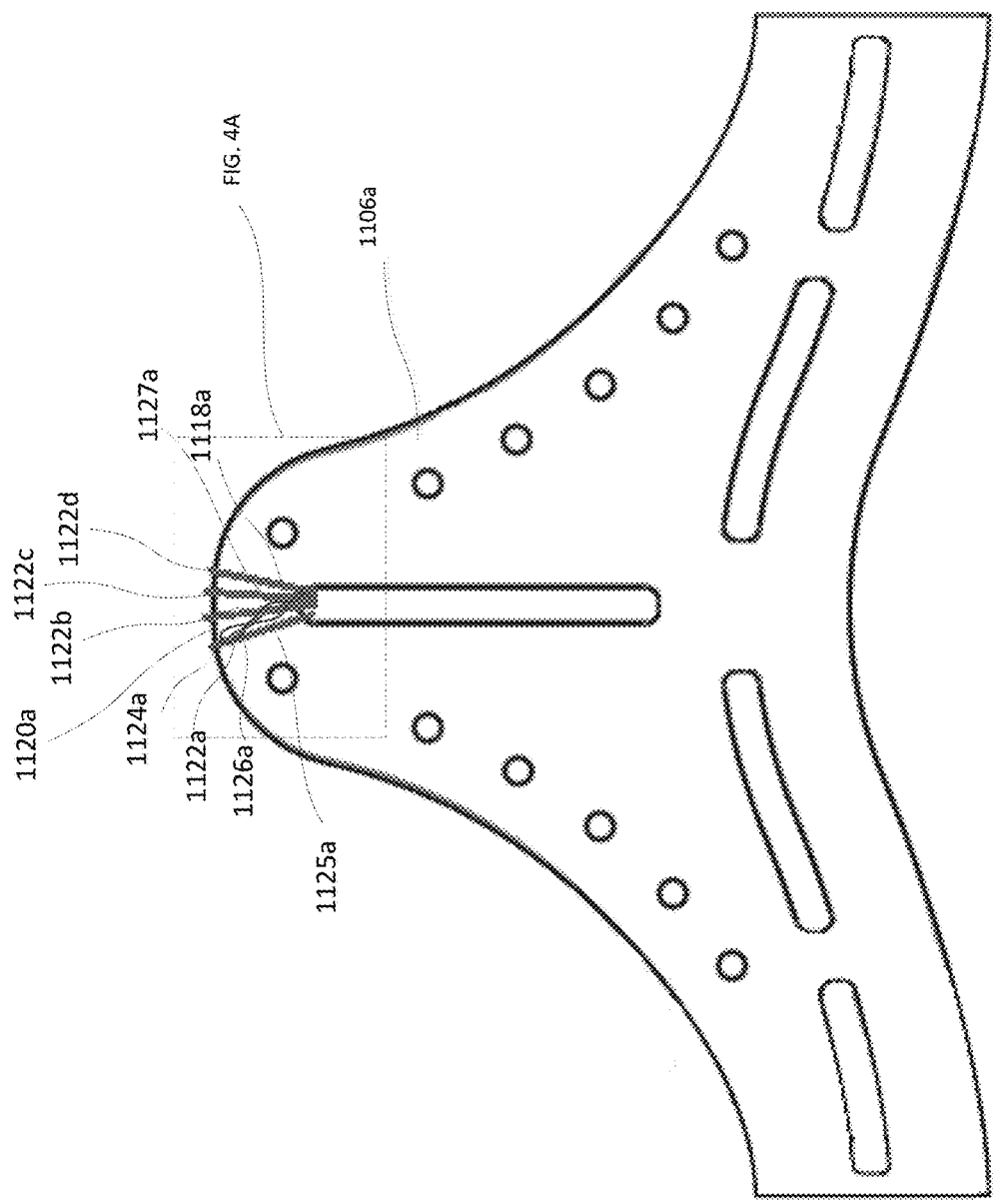
FIG. 3B is a fragmentary front view of a one-third section of the frame of FIG. 3A.
Figure 6A:
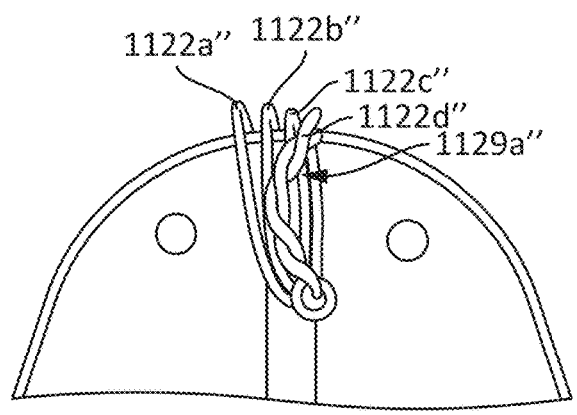
FIG. 6A is an enlarged fragmentary view of another alternate embodiment of the frame shown in FIGS. 3A and 3B.
Figure 6B:
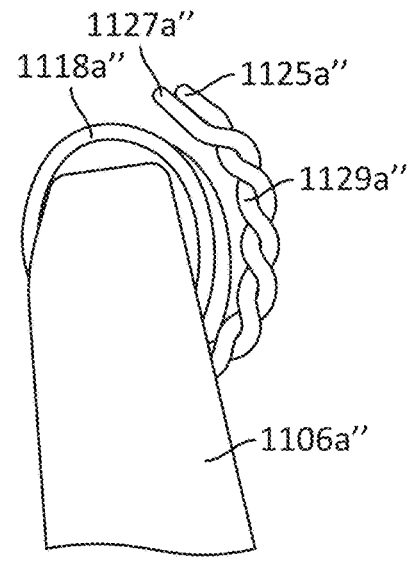
FIG. 6B is a side view of what is shown in FIG. 6A.

Referring to FIGS. 3A-3B, a frame 1100 is shown with the same underlying structure as frame 100 in FIGS. 1-2, but without an annular wire adjacent the base 1104. To assist the surgeon in better identifying the location of frame 1100, and particularly, the positions and orientations of the commissure posts within a human body, frame 1100 further includes at least one element having radiopaque properties positioned on one or more of the commissure posts. Such radiopaque elements can block radiation, rather than allowing radiation to pass through them, which causes the radiopaque element to be visible under a fluoroscope or on x-rays.

The radiopaque element may be a metal wire formed from stainless steel, but the metal wire may be comprised of any radiopaque material, including other metals, including titanium, or aluminum, or metal alloys. The wire may alternatively be a radiopaque clad wire that incorporates a metal, such as gold, platinum-iridium, tantalum, tantalum-tungsten and other metals or metal alloys bonded to a high strength wire, such as stainless steel or nitinol wire. Examples of radiopaque clad wire include tantalum clad stainless steel and gold clad nitinol.

The wire may have any desired diameter, but in one example can range in size from about 0.23 mm to about 1 mm in diameter. In other examples, the wire may have a diameter greater than about 1 mm or less than about 0.23 mm. It is to be appreciated that the wire must not be too thick or wrapped too many times around any one of the commissure posts 1106a, 1106b, 1106c. Otherwise, the wire-wrapped portions of the frame become rigid and interfere with the coaptation of the valve leaflets.

In one example, a radiopaque wire may be positioned towards the respective tips 1120a, 1120b, 1120c of commissure posts 1106a, 1106b, 1106c. With specific reference to commissure post 1106a, as shown in FIGS. 3B, 4A, 4B, radiopaque wire 1118a includes a first end 1124a, a second end 1126a, and a main body wrapped around the tip 1120a of commissure post 1106a. Radiopaque wire 1118a may extend through post slot 1114a, around the tip 1120a of commissure post 1106a, and back around through post slot 1114a. The radiopaque wire 1118a may be wrapped around the tip 1120a of commissure post 1106a and through post slot 1114a any number of times, but in this example, wire 1118a wraps around the commissure post tip four times, such that four individual wire wraps or rays 1122a, 1122b, 1122c, 1122d are seen across the outer surface 1128 of frame 1100. In other examples, the wire may be wrapped around the commissure post tip fewer than four times or as little as one time, as well as greater than four times, such as five or six times.

Wire 1118a may be secured to frame 1100 in any number of ways. In the illustrated example, prior to wrapping, an initial excess length 1125a of wire 1118a adjacent first end 1124a may be provided that is not wrapped around commissure post 1106a. Once radiopaque wire 1118a is wrapped around commissure post 1106a the desired number of times, another excess length 1127a of wire 1118a adjacent second end 1126a may be provided. The excess lengths 1125a, 1127a may be positioned adjacent one another and then tucked underneath the main body of wire 1118a. In this example, the first and second ends are not directly secured to each another and are instead tucked underneath rays 1122a, 1122b, 1122c, 1122d against the outer surface 1128 of frame 1100. FIG. 4B shows a side view of wrapped wire 1118a illustrating that this configuration allows for a narrow profile that closely matches the profile of frame 1100. This allows for a less bulky configuration and one that can aid in manufacturability.

Figure 7A:
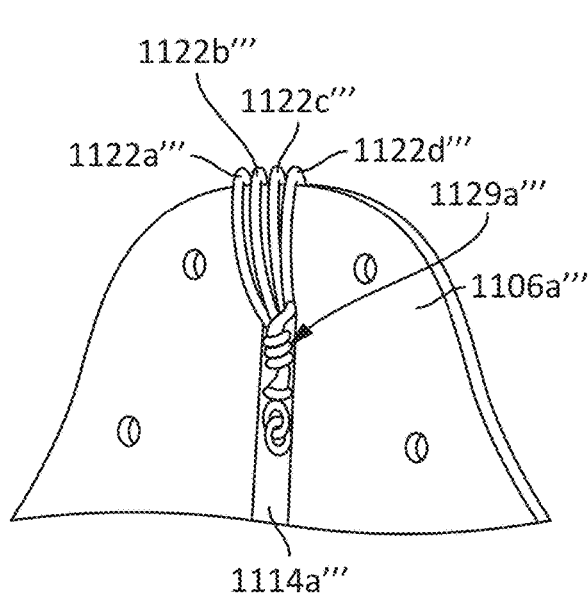
FIG. 7A is an enlarged fragmentary view of a still further embodiment of the frame shown in FIGS. 3A and 3B.
Figure 7B:
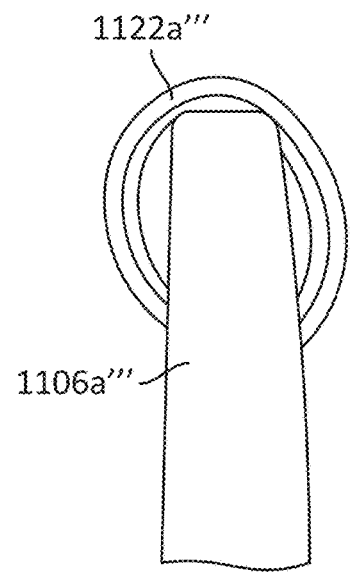
FIG. 7B is a side view of what is shown in FIG. 7A.

Alternate techniques for securing the wire to frame 1100 are also contemplated herein. FIGS. 5A-7B illustrate alternative examples in which the first and second ends of the wire are secured to one another. With reference to FIGS. 5A-5B, the excess length 1125a' adjacent the first end 1124a' of wire 1118a' and the excess length 1127a' adjacent the second end 1126a' of the wire may be twist tied or intertwined together. The resulting twisted section 1129a' may be folded adjacent wire rays 1122a', 1122b', 1122c', 1122d'. As shown, twisted section 1129a' may be positioned adjacent ray 1122d'. Alternatively, as shown in FIGS. 6A-6D, the excess lengths 1125a" and 1125b" of wire 1118a" may be intertwined so that the twisted section 1129a" overlaps the main body or rays 1122a", 1122b", 1122c", 1122d" of the wire in a diagonal direction. Alternatively, as shown in FIGS. 7A-7B, the twisted section 1129a'" may be positioned within the slot 1114a'" of commissure post 1106a, such that the twisted section 1129*a*''' is positioned directly below rays 1122*a*''', 1122*b*''', 1122*c*''', 1122*d*'''.

Figure 7C:
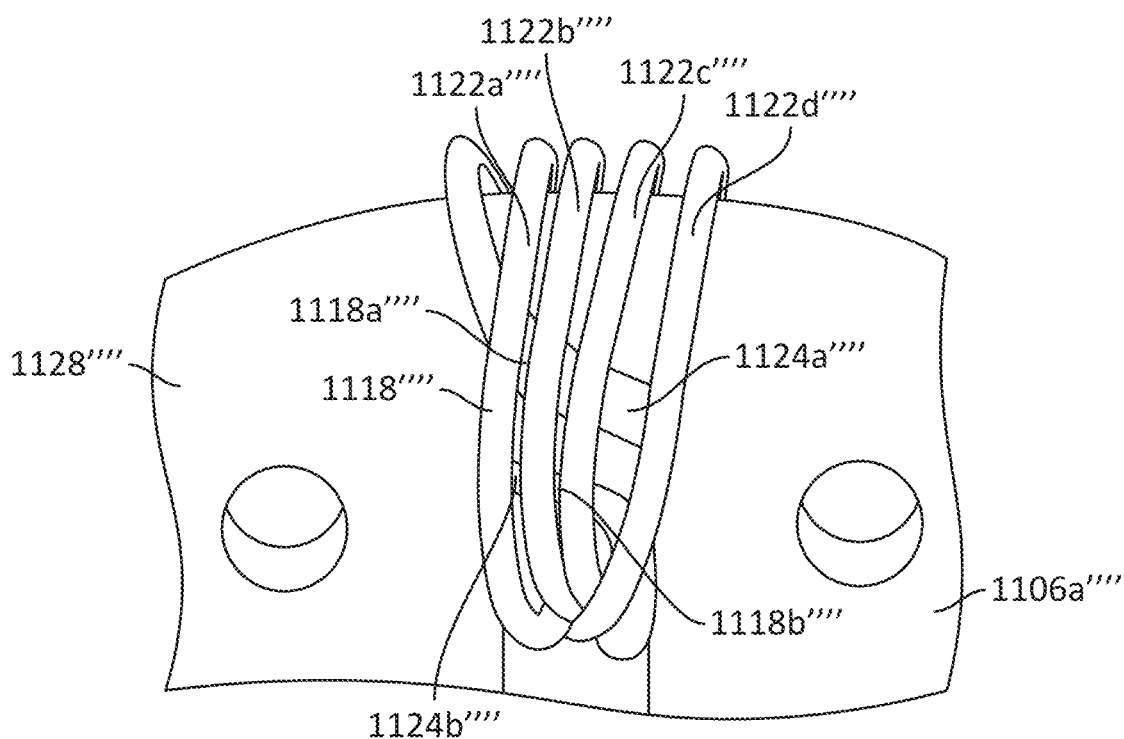
FIG. 7C is an enlarged fragmentary view of another alternate embodiment of the frame shown in FIGS. 3A and 3B.
Figure 7D:
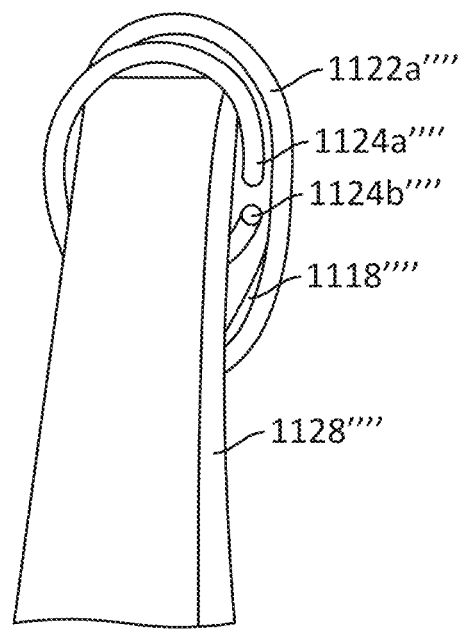
FIG. 7D is a side view of what is shown in FIG. 7C.

FIGS. 7C-7D illustrates another technique and example for securing the wire to the frame, in which the ends of the wire remain free ends that are not secured to one another. As shown, a first end 1124*a*'''' and a second end 1124*b*'''' of the wire 1118'''' are tucked underneath or below the wire wraps or rays 1122*a*'''', 1122*b*'''', 1122*c*'''', and 1122*d*''''. This can help to prevent the first and second ends of the wire 1118'''' from protruding beyond the wire rays 1122*a*'''', 1122*b*'''', 1122*c*'''', and 1122*d*'''', as well as through the fabric and/or tissue that will be attached to the commissure posts 1106*a*'''' of the frame.

The wire 1118'''' can be wrapped in any way that will ensure the first end 1124*a*'''' and the second end 1124*b*'''' are tucked underneath or below one or more rays. In one example, an excess length 1118*a* of wire 1118'''', including the first end 1124*a*'''', may be positioned at the front and outer surface 1128'''' of the commissure post 1106*a*''''. The length of wire 1118'''' can then be wrapped around the rear of the commissure post 1106*a*'''' and back through the post slot 1114*a*'''' of the commissure post 1106*a*'''' so that the wire 1118'''' overlies the first end 1124*a*''''. The wire 1118'''' can be wrapped any number of times around the commissure post 1106*a*'''' and back through the post slot 1114*a*''''. In this example, wire 1118'''' is wrapped around and back through the post slot 1114*a*'''' five times, so as to create four wire rays 1122*a*'''', 1122*b*'''', 1122*c*'''', and 1122*d*'''' that both extend through the post slot 1114*a*'''' and over the tip 1120'''' of the commissure post 1106*a*''''. Once the wire has been wrapped the desired number of times, an excess length 1118*b* of wire 1118'''' adjacent the second end 1124*b*'''' can be tucked or placed underneath each of the four wire rays 1122*a*'''', 1122*b*'''', 1122*c*'''', and 112*d*''''. As shown, the second end 1124*b*'''' can be positioned directly below the first end 1124*a*'''' or closer to the inflow end (not shown) of the stent. As a result of this construction, both the first and second ends 1124*a*'''', 1124*b*'''' will be positioned between the four wire rays 1122*a*'''', 1122*b*'''', 1122*c*'''', and 1122*d*'''' and the frame.

Radiopaque wire may also be wrapped around more than one commissure post. For example, with reference back to FIG. 3A, wire 1118*b* may be wrapped around the tip of commissure post 1106*b* and wire 1118*c* may be wrapped around the tip of commissure post 1106*c*. For ease of discussion, only radiopaque wire 1118*a* has been discussed, but it is to be understood that a radiopaque wire may be similarly wrapped around the other commissure posts 1106*b* and 1106*c*, and that the same attributes of the wire and techniques may be applied.

It is to be further appreciated that the radiopaque element used to form the arrays or wire wraps need not be limited to a radiopaque wire, but may include any radiopaque elements that may extend around, along, within or adjacent the commissure post. For example, one or more individual flexible and radiopaque bands may be clipped over the tips of the commissure posts and positioned directly adjacent one another to form the arrays on the commissure posts.

Frame 1100 may be formed from a polymeric material, including an injection molded monolithic polymer. As used herein, the term "monolithic" refers to a structure that is formed entirely from a polymeric material, rather than to structures that may have a non-polymeric core and a polymeric coating, or a polymeric core and a non-polymeric coating. The term "monolithic" is not intended to be limited to structures formed from a single polymeric material. Thus, "monolithic" polymer structures include those that may be formed from a mixture of different polymeric materials, as well as those that may include layers or regions formed from the same or different polymeric materials. Moreover, although injection molding is a preferred method for manufacturing frame 1100, it is contemplated that the stent may be formed by other techniques known in the art. For example, stent 1100 may be formed by machining or laser cutting a tube of polymeric material in a manner similar to the manner in which the prior art metal stents are formed.

Figure 8:
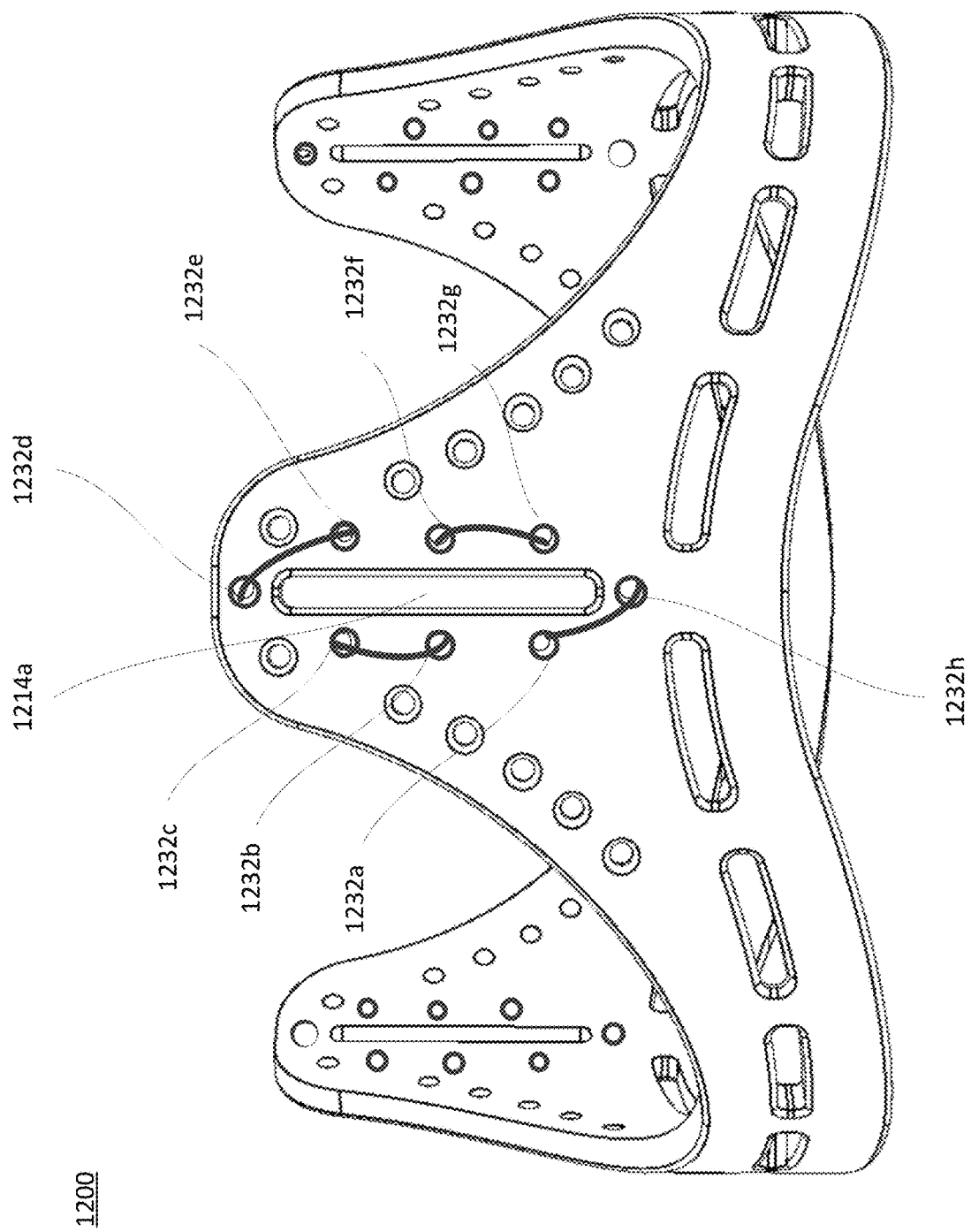
FIG. 8 is a front elevational view of the frame of a surgical heart valve having radiopaque elements according to another embodiment of the disclosure.
Figure 9B:
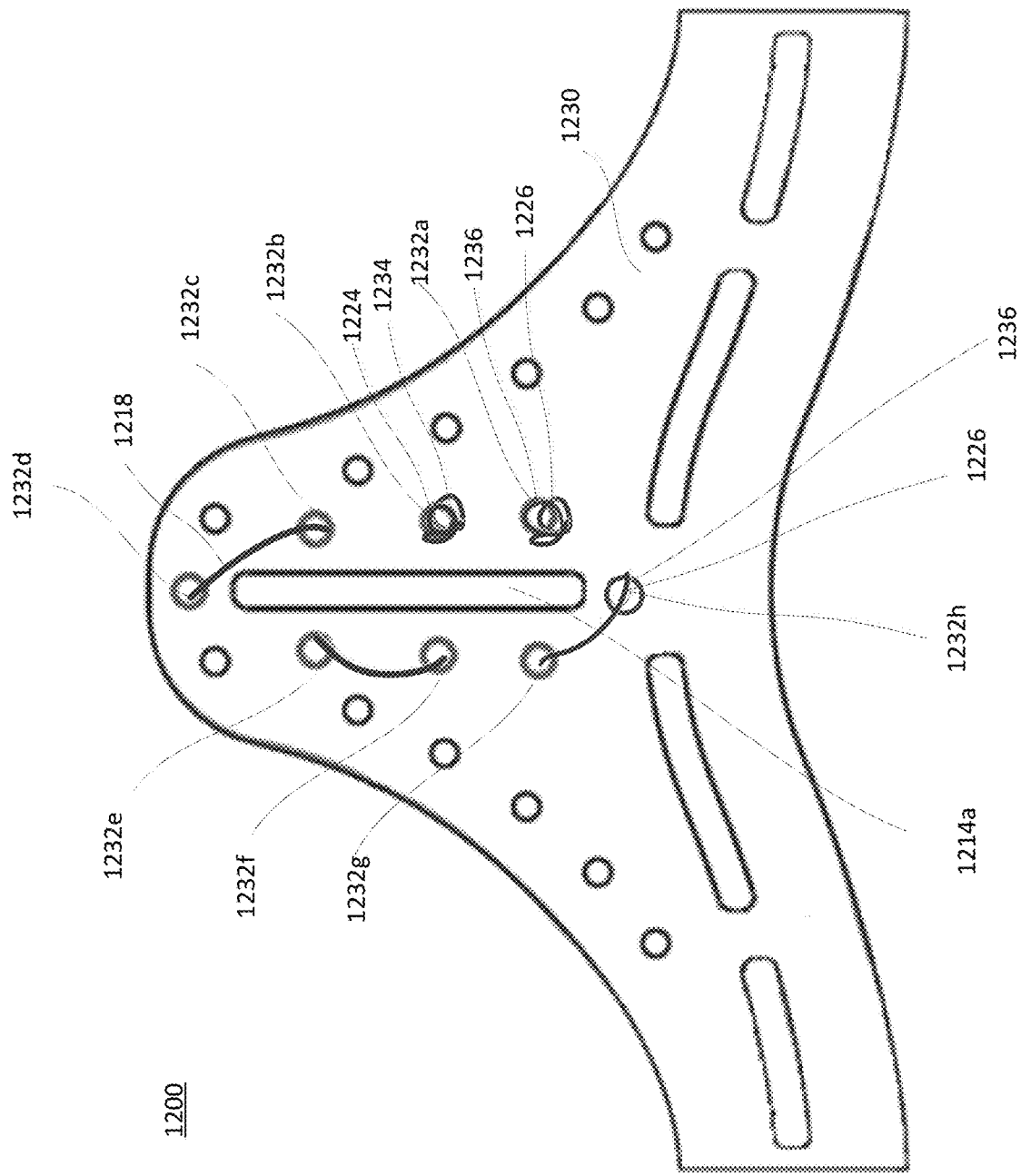
FIG. 9B is a rear view of what is shown in FIG. 9A.

Various alternative configurations may be used to provide a visual indicator on an x-ray or fluoroscope to identify the position and orientation of the commissure posts within a human body. FIGS. 8-14 illustrate alternative structures that allow a radiopaque material to extend along at least a portion of a commissure post. With reference first to FIGS. 8-9B, frame 1200 is similar to frame 1100 described above, but further includes additional apertures along and around the length of commissure post slot 1214*a* which may be used to receive radiopaque elements or components to help secure a radiopaque element to the commissure post. As shown, three apertures 1232*a*, 1232*b*, 1232*c* are positioned to the left of commissure post slot 1214*a*, three apertures 1232*e*, 1232*f*, 1232*g* are positioned to the right of the commissure post slot, a single aperture 1232*d* is provided adjacent the top of the commissure post slot, and a single aperture 1232*h* is provided adjacent the bottom of the commissure post slot. Apertures 1232*a-h* may be any size, but are preferably sized to be slightly larger than the diameter of at least one radiopaque wire to be woven into the apertures.

A radiopaque wire, such as the previously described radiopaque wire 1118*a*, may be weaved into and out of each of the apertures. With reference to FIG. 9A, an enlarged fragmentary front view of a one-third section of frame 1200, and FIG. 9B, a rear view of what is shown in FIG. 9A, radiopaque wire 1218 extends along and around the length of commissure post opening 1214*a*. A first end 1224 of radiopaque wire 1218 may be tied into a knot 1234 at the rear surface 1230 of frame 1200 (FIG. 9B) at aperture 1232*b* and then weaved through the rear and out of the front of aperture 1232*b*, and then into the front and out of the rear of aperture 1232*c*. Radiopaque wire 1218 may be continuously weaved into and out of the remaining apertures 1232*d-h*. Second end 1226 of radiopaque wire 1218 may be passed through aperture 1232*a* and tied into a knot 1236 or secured to frame 1200 by any means. In one alternative example, the first and second ends 1224, 1226 of wire 1218 may extend toward one another from apertures 1232*b*, 1232*a*, respectively, and may be secured to one another, such as by tying the ends together or by tying second end 1226 to knot 1234. It is to be appreciated that in other embodiments, instead of securing the first end 1224 and second end 1226 together at rear surface 1230 of frame 1200, the first and second ends 1224, 1226 can be secured together at the opposed front surface (FIG. 9A) of frame 1200. In such embodiment, knot 1236 is positioned away from the leaflets, which can help to mitigate leaflet damage due to use over time.

Figure 10:
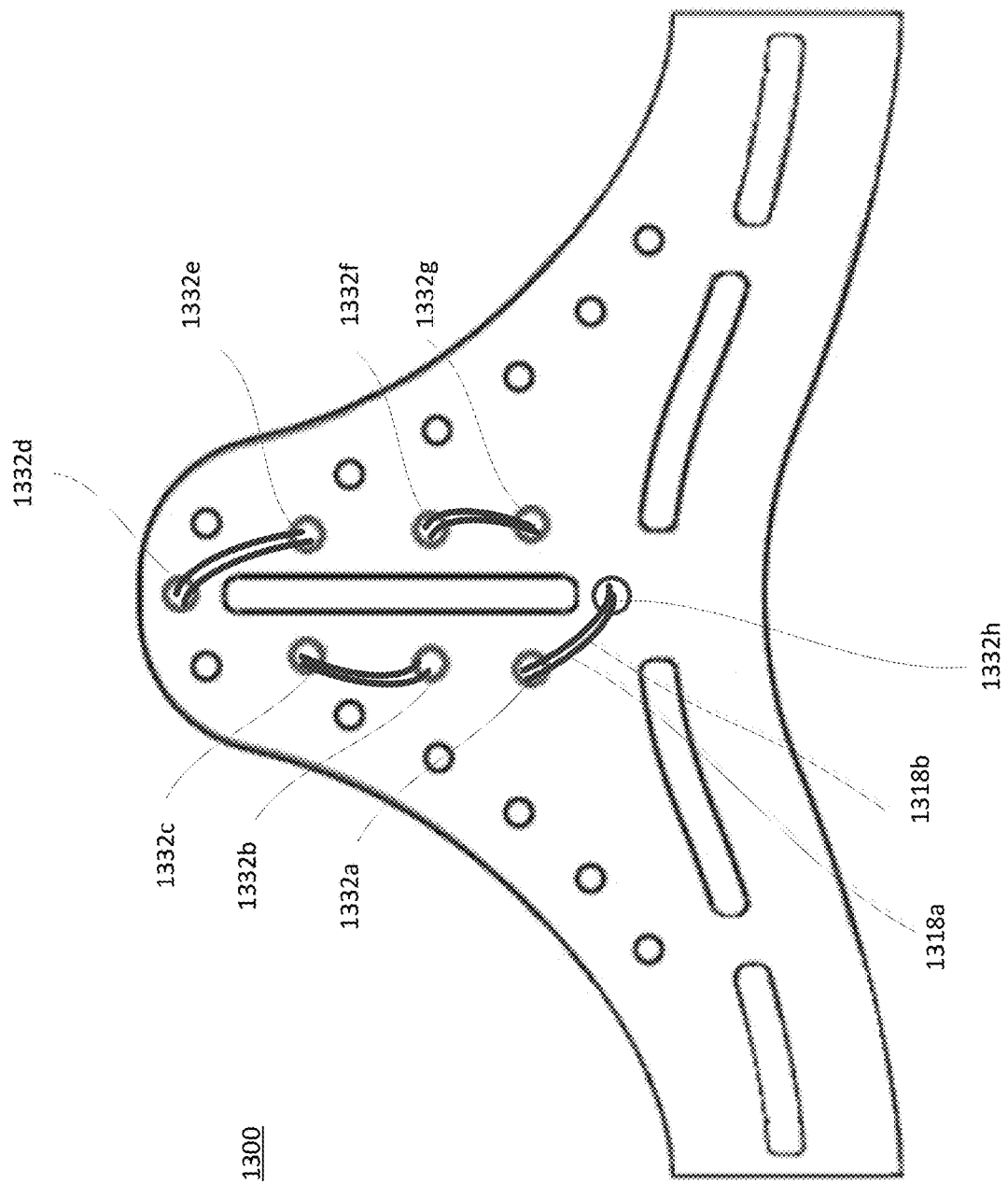
FIG. 10 is a fragmentary front view of a one-third section of the frame of a surgical heart valve having radiopaque elements according to another embodiment of the disclosure.

The radiopaque wire may be weaved through the apertures more than one time, if desired, which will increase the visibility of the radiopaque wire in an x-ray or fluoroscope. With reference to FIG. 10 and example frame 1300, a first radiopaque wire 1318*a* and a second radiopaque wire 1318*b* are weaved through apertures 1332*a*-1332*h*, such that there are two adjacent wires extending into and out of each aperture. As in the prior example, the first end can be tied into a knot (not shown) at the rear surface. Radiopaque wires may be weaved through apertures 1332*a*-1332*h* any number of times, provided that the collective diameter of the wires extending through the apertures does not exceed the diameter of any one of the apertures through which the wires extend. The second ends may also be tied off into a knot in the rear. Increasing the number of wires may help to improve the visibility of the commissure posts on a scan.

Figure 11A:
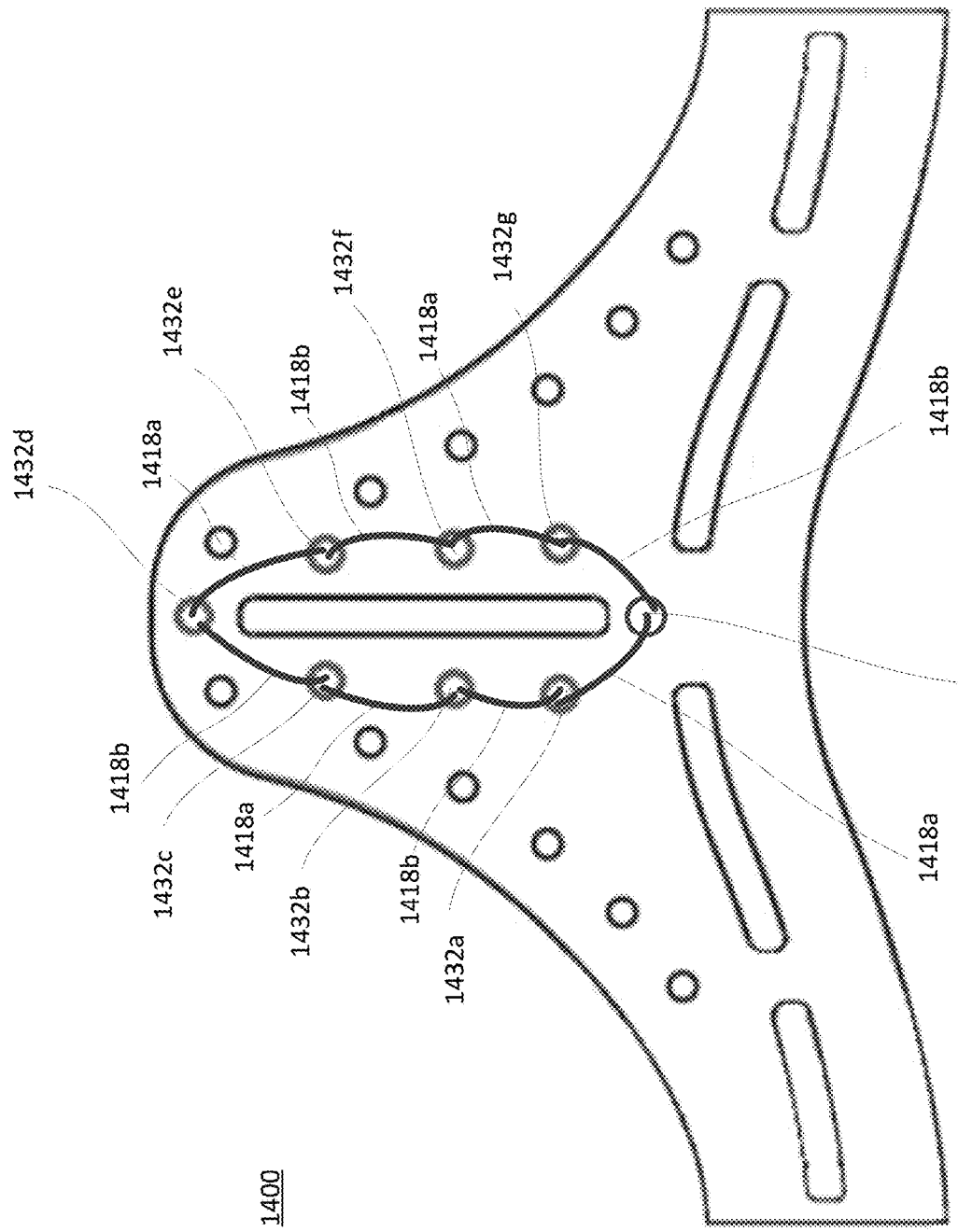
FIG. 11A is a view similar to FIG. 10 according to another embodiment thereof.
Figure 11B:
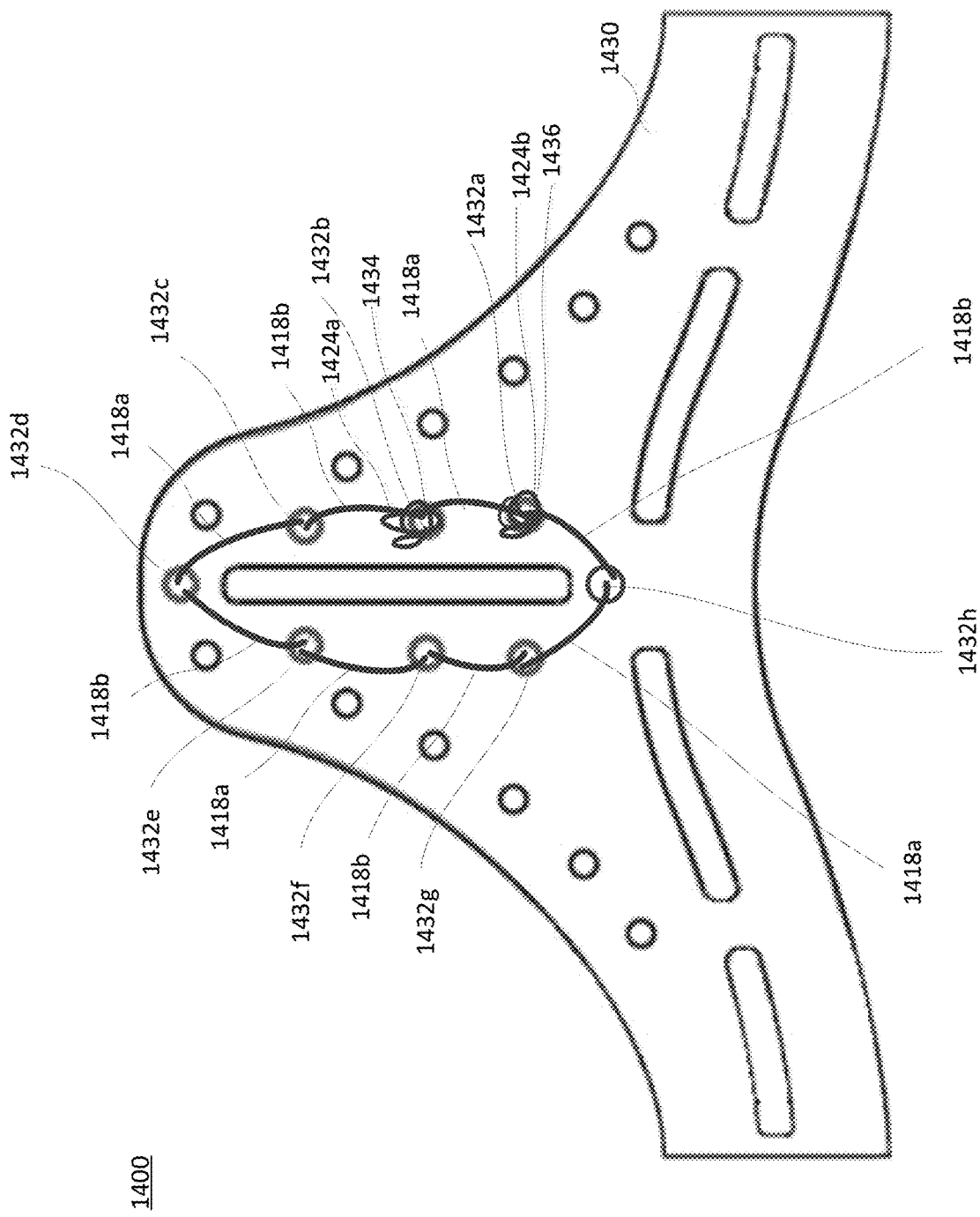
FIG. 11B is a rear view of what is shown in FIG. 11A.

Alternatively, weaving of the first and second wires may be staggered so that radiopaque wire is seen extending between each of the apertures from both sides of the frame, as opposed to between pairs of apertures spaced apart from one another, as in the previous example of FIG. 10. Referring to FIG. 11A, a fragmentary front view of a one-third section of frame 1400, wire 1418a is shown extending around annular slot 1414a and between apertures 1432b-1432c, apertures 1432d and 1432e, 1432f-1432g, and apertures 1432h-1432a. As in the previous example, the first end 1424a of first wire 1418a may be tied in a knot 1434 at the rear surface 1430 of aperture 1432b (or alternatively tied in a knot at the front surface of aperture 1432b shown in FIG. 11A). The first end 1424b of a second radiopaque wire 1418b may be tied into a knot 1436 at the rear surface 1430 of aperture 1432a and weaved into and out of alternating openings 1432a-b, 1432c-1432d, 1432e-1432f, and 1432g-1432h, also as seen on the front surface of frame 1400 shown in FIG. 11A.

Figure 12:
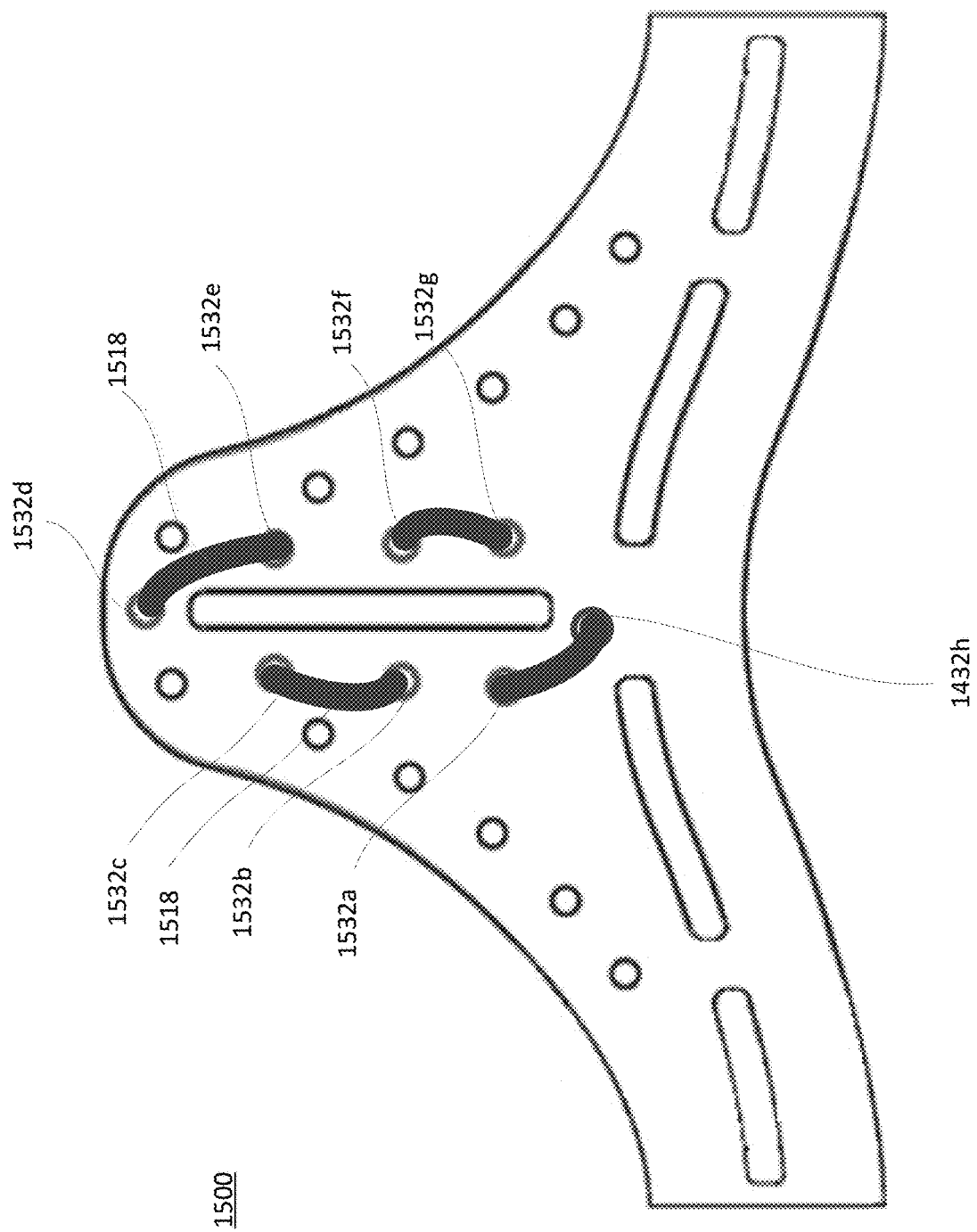
FIG. 12 is a view similar to FIG. 10 according to another embodiment thereof.

The thickness of the wire may alternatively or additionally be varied to increase visibility of the commissure posts on x-rays, fluoroscopes or the like. FIG. 12 illustrates the use of a wire 1518 having a diameter that is only slightly smaller than the diameter of the wire apertures 1532a through 1532h in frame 1500. Wire 1518 is weaved into and out of each of the apertures 1532a-1532h, as in the previous examples. An example wire may have a diameter of about 0.8 mm, but a wire with a diameter that is greater than or less than 0.8 mm may be used.

Figure 13:
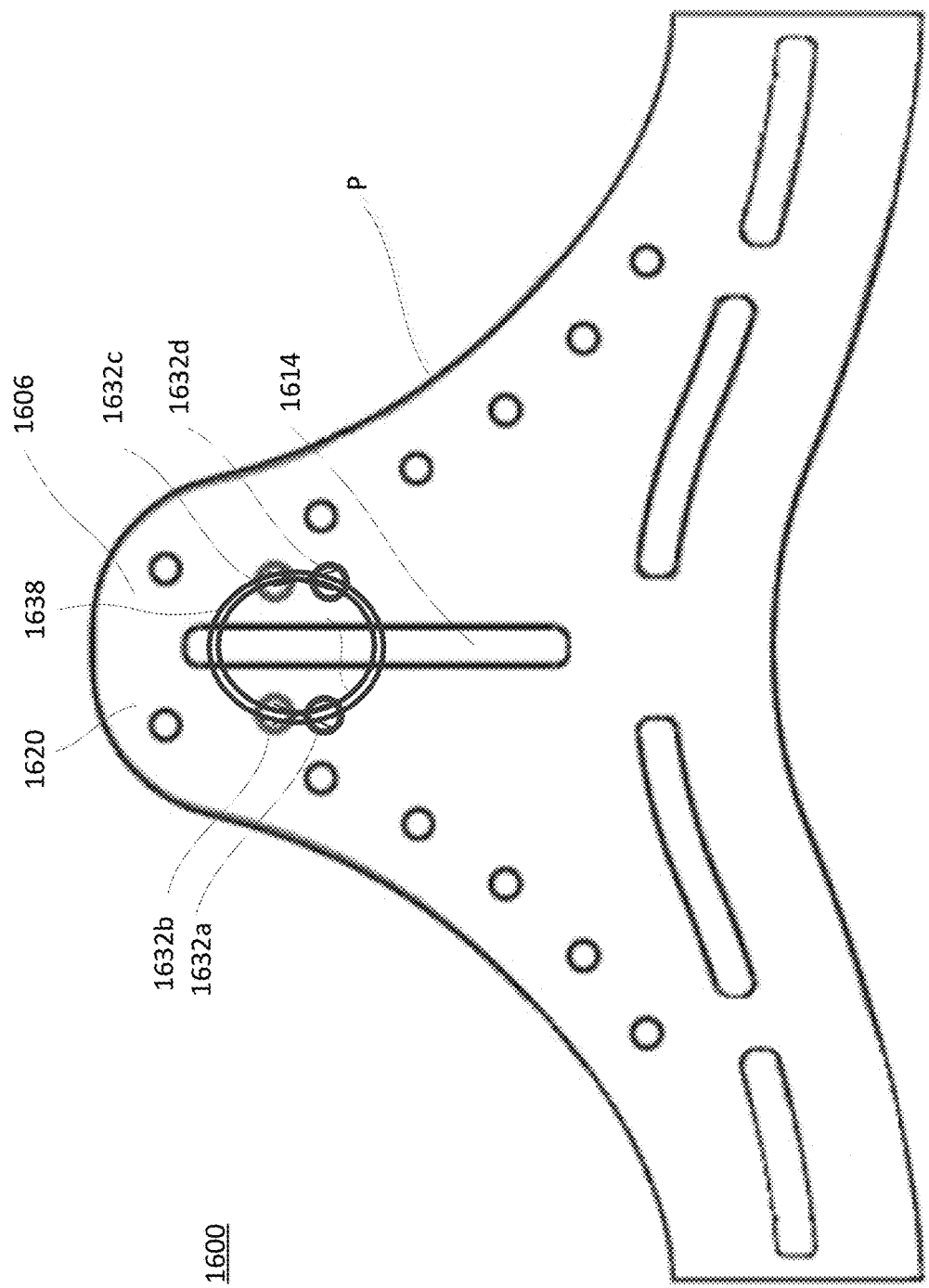
FIG. 13 is a view similar to FIG. 10 according to another embodiment thereof.

Radiopaque objects or markers may be attached to the commissure posts, or to any other portion of the frame. FIG. 13 illustrates a fragmentary front view of a one-third section of an alternative frame 1600 that includes at least two wire apertures 1632a and 1632b to the left of commissure post slot 1614, and two wire apertures 1632c and 1632d to the right of the commissure post slot. A radiopaque washer 1638 may be attached to the frame toward the top edge of commissure post slot 1614. Washer 1638 may be a round washer having a diameter that does not extend beyond the peripheral edge P of frame 1600. Washer 1638 may be attached directly to frame 1600 by any means. In this example, a wire or sutures may be threaded through apertures 1632a, 1632b and 1632c, 1632d to secure washer 1638 to commissure post 1606. In other examples, washer 1638 may instead be attached directly to the fabric that will be provided around frame 1600 during manufacture of the surgical heart valve. In still other examples, washer 1638 may be attached to commissure post 1606 in a variety of ways, including the use of a wire, suture, or other means of attachment that may extend around the commissure tip 1620, through the opening of the washer, and through commissure post slot 1614.

Figure 14:
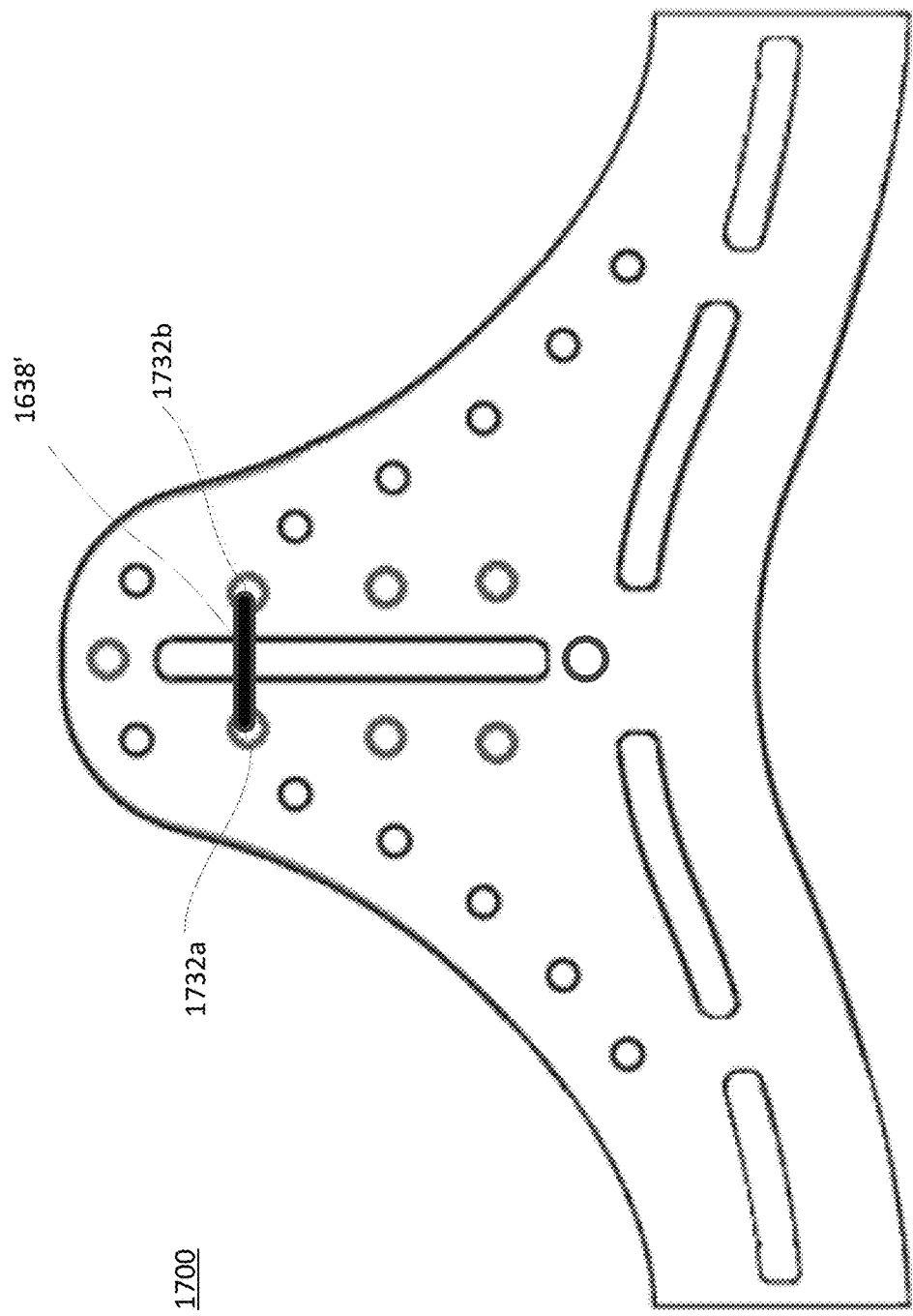
FIG. 14 is a view similar to FIG. 10 according to another embodiment thereof.

The radiopaque objects or markers may take on any variety of shapes, sizes, and forms. FIG. 14 illustrates an alternative object attached to a frame. In this example, an elongated radiopaque bead 1638' is attached to frame 1700. Any size and style of bead may be used. In this example, bead 1638' includes a bore or lumen (not shown) extending through its length. A securing element, such as a wire, suture or the like, may extend through the bore of bead 1638' and through the respective apertures 1732a, 1732b on opposed sides of the bead.

Radiopaque Elements on Base of Frame

Figure 15A:
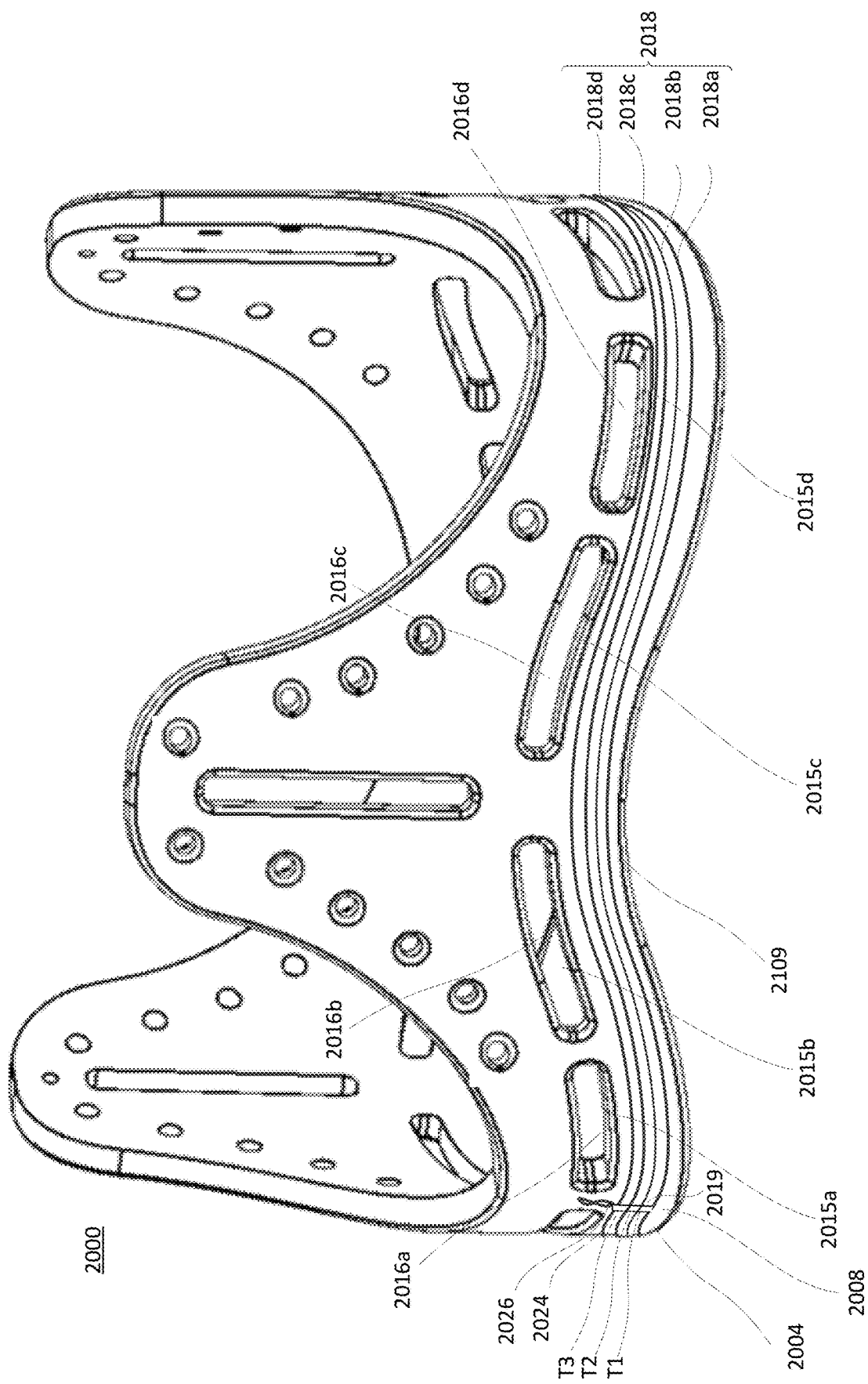
FIG. 15A is a perspective view of a frame of a surgical heart valve having radiopaque elements according to another embodiment of the disclosure.
Figure 15B:
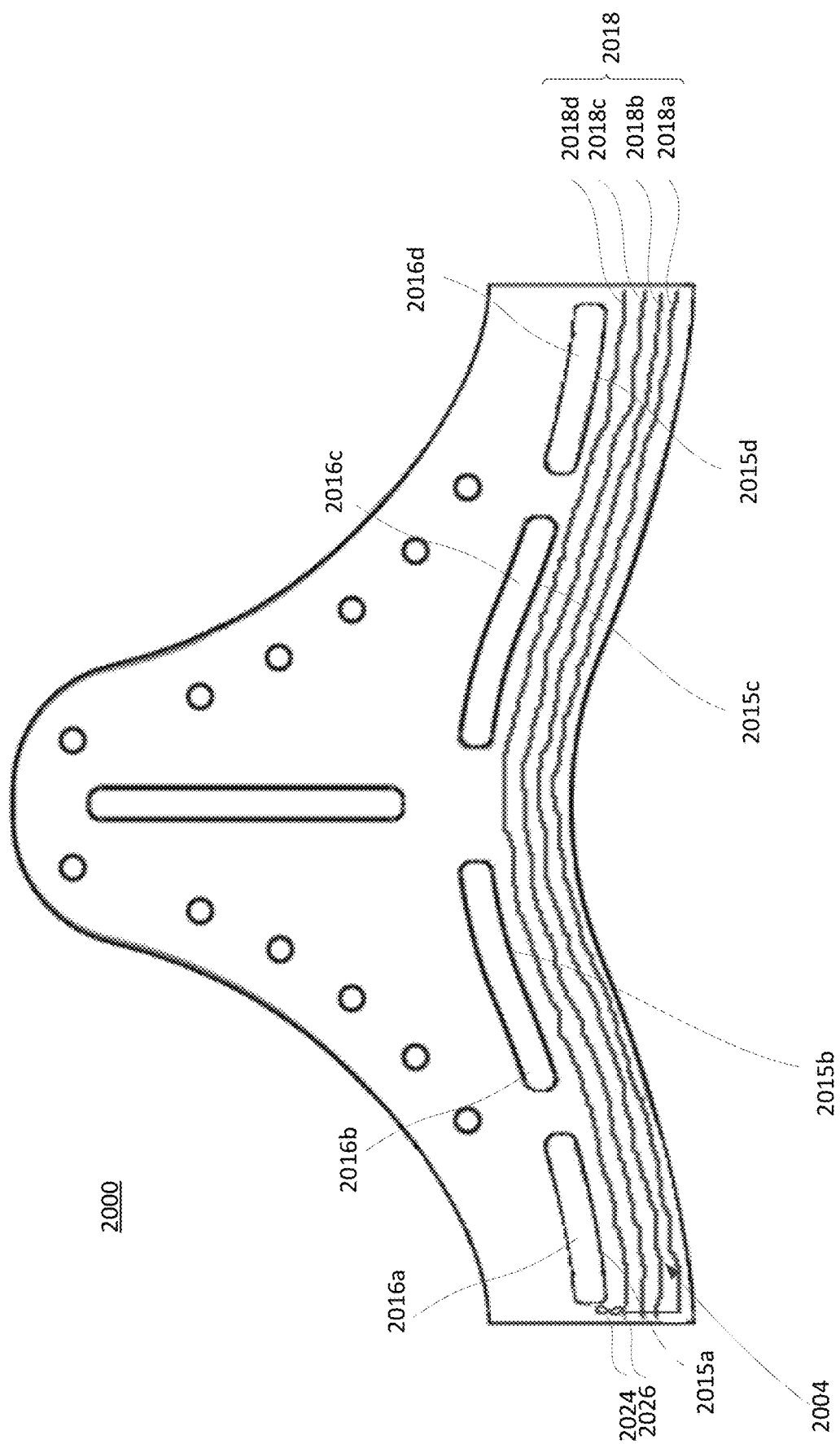
FIG. 15B is a fragmentary front view of a one-third section of the frame of FIG. 15A.

Radiopaque elements may additionally or alternatively be provided around the base of the frame annulus to help identify the position of the base within a patient's body. FIG. 15A is a perspective view of a frame 2000, while FIG. 15B is a fragmentary front view of a one-third section of the frame. Frame 2000 is similar to frame 100 described above, but further includes an annular wire 2018 that extends circumferentially around the entire base 2004 of the frame. In this example, annular wire 2018 is a single length of wire that is continuously wrapped around the base of frame 2000 four times. A first wire wrap 2018a, a second wire wrap 2018b, a third wire wrap 2018c, and a fourth wire wrap 2018d extend around base 2004.

The wire wraps 2018 extending around the base 2004 of frame 2000 can be provided in a variety of patterns. As shown, each wrap 2018 may be evenly spaced between inflow edge 2008 and each of the respective bottom edges 2015a-d of base openings 2016a-2016d. Each wire wrap may have a shape or profile matching the scalloped shape of inflow edge 2008. In other examples, the annular wire wraps may be more closely spaced together or spaced further apart.

As shown in FIGS. 15A-B, an excess length 2019 at the first end 2024 of wire 2018 may be provided prior to wrapping the wire. The excess length 2019 may extend in two directions, a first upwards direction toward the bottom edge 2015a of base opening 2014a and a second perpendicular direction in which wire 2018 begins wrapping around the base 2004 of frame 2000. The second, third and fourth wire wraps 2018b-d may be wrapped over excess length 2019 adjacent first end 2024 or in other embodiments underneath the excess length.

Wire 2018 may be a single wire that continuously extends around the base 2004 of frame 2000, with the wire having a first end 2024 and a second end 2026. When the wrapping of the wire begins, the first wrap 2018a may be positioned around base 2004 closest to inflow edge 2008. A second wire wrap 2418b, third wire wrap 2418c, and fourth wire wrap 2418d will successively extend around the base. To allow a single wire to continuously extend around base 2004, a transitional length of wire may extend between each row of wire wrapping. For example, a wire transition T1 may extend between first wire wrap 2018a and second wire wrap 2018b; a wire transition T2 may extend between the second wire wrap and third wire wrap 2018c; and a wire transition T3 may extend between the third wire wrap and fourth wire wrap 2018d. Each of the transitions is a length of wire extending in a vertical or upwards direction. It is to be appreciated that the length of wire between any two wraps, as well as the specific transition between any two wire wraps, may be any desired shape or line that allows one continuous wire to be wrapped around base 2004 of frame 2000. Additionally, transitions T1, T2, T3 need not all be at the same annular position around base 2004, but may be at staggered positions around the base.

When the desired number of wraps have been made, in this example four wraps, the first and second ends 2024, 2026 may be intertwined together in the manner previously described to secure wire 2018 to frame 2000. In alternative examples, second end 2026 may include an excess length of wire so that the second end extends toward the first end 2024 for securing the first and second ends together. Similarly, both the first end 2024 and the second end 2026 may include excess lengths of wire to allow the first and second ends to meet and be secured or tied together at a position between the first wire wrap 2018a and the last wire wrap 2018d.

Figure 16A:
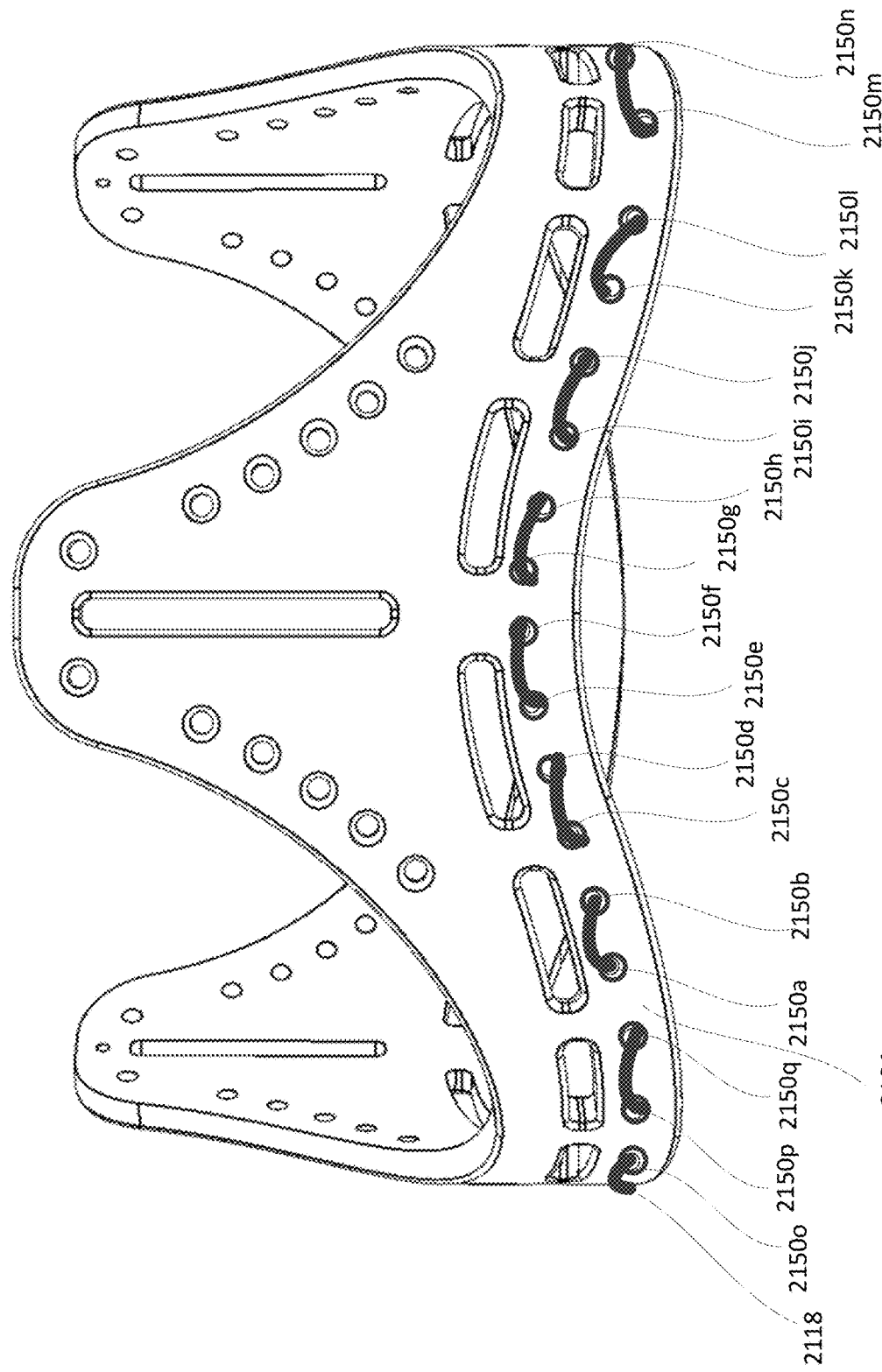
FIG. 16A is a front elevational view of the frame of a surgical heart valve having radiopaque elements according to another embodiment of the disclosure.
Figure 16B:
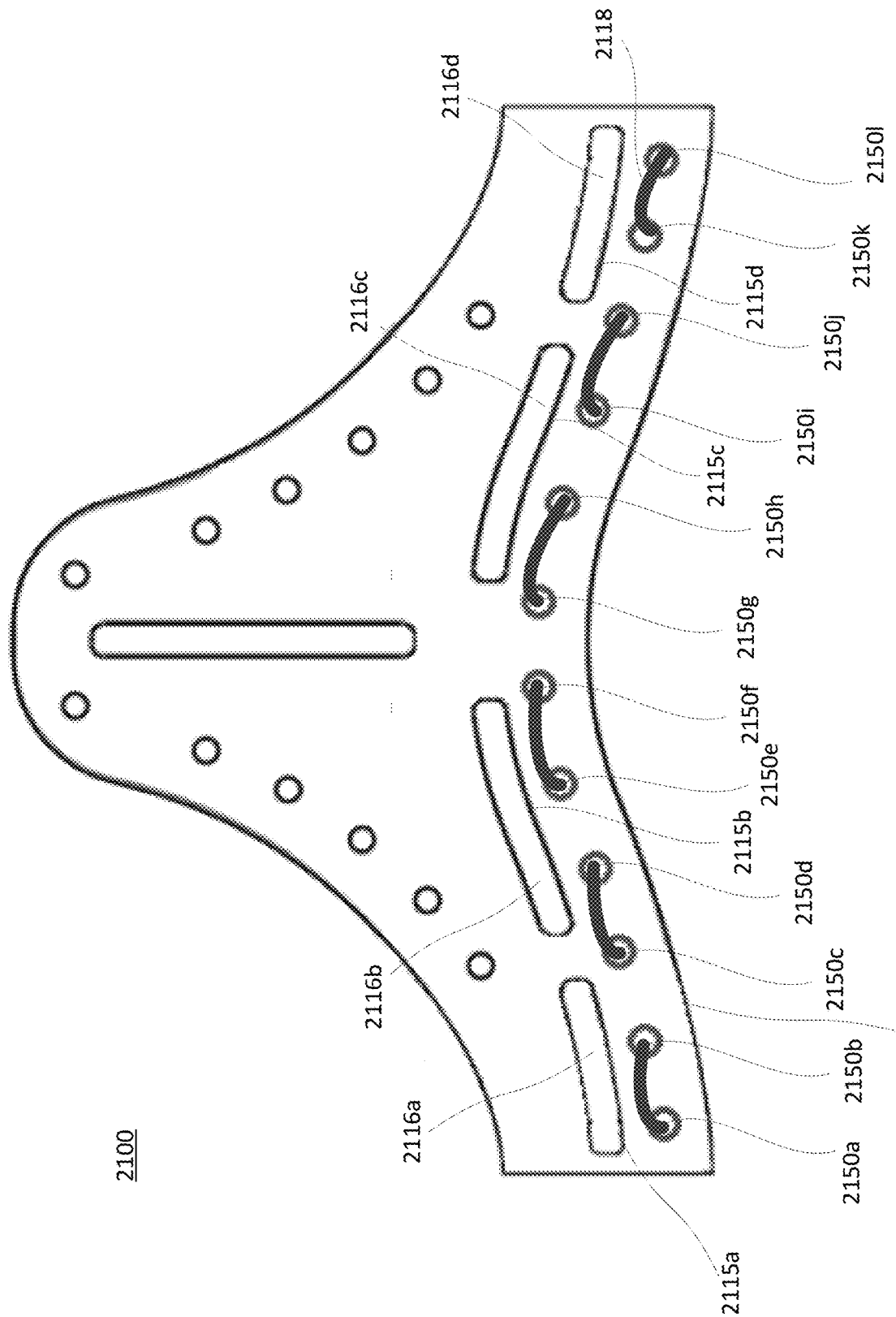
FIG. 16B is a fragmentary front view of a one-third section of the frame of FIG. 16A.

In another example, additional apertures may be provided along the annular base 2104 of frame 2100 to accommodate one or more wires extending therethrough. With reference to FIGS. 16A-B, apertures 2150*a-q* extend around base 2104 between inflow edge 2108 and respective bottom edges 2115*a-d* of base openings 2116*a-d*. The apertures extend around the entirety of base 2104, but for ease of discussion, only the apertures visible in FIGS. 16A and 16B are shown. Apertures 2150*a*-21501 follow the scallop-shaped contour of the inflow edge 2108 and extend around the entire circumference (not shown) of frame 2100. As in the example of FIGS. 9A-9C, wire 2118 may be weaved into and out of each of the apertures. One end (not shown) of wire 2118 may be tied in a knot or otherwise secured to the inside of frame 2100 as the second end (not shown) is threaded into and out of each of the apertures. For example, the second end will be threaded in from the rear and out from the front of aperture 2150*a*; in from the front and out from the rear of aperture 2150*b*; in from the rear and out from the front of aperture 2150*c*; in from the front and out from the rear of aperture 2150*d*; in from the rear and out from the front of aperture 2150*e*; in from the front and out from the rear of aperture 2150*f*; in from the rear and out from the front of aperture 2150*g*; in from the front and out from the rear of aperture 2150*h*; in from the rear and out from the front of aperture 2150*i*; in from the front and out from the rear of aperture 2150*j*; in from the rear and out from the front of aperture 2150*k*; in from the front and out from the rear of aperture 2150*l*; in from the rear and out from the front of aperture 2150*m*; in from the front and out from the rear of aperture 2150*n*; in from the front and out from the rear of aperture 2150*o*; in from the rear and out from the front of aperture 2150*p*; and in from the front and out from the rear of aperture 2150*q*. Wire 2118 may extend continuously through the remaining apertures (not shown) positioned around the base 2104 of frame 2100. The second end may be tied in a knot behind any of the apertures or may be secured to frame 2100 using any known means. In other examples, instead of one continuous wire extending around the entirety of base 2104, two or more segments of wire may be separately threaded into and out of the apertures around the base.

Apertures 2150*a*-1 may be positioned at an equal distance between inflow edge 2108 and the respective bottom edges 2115*a-d* of base openings 2116*a-d*. In other examples, apertures 2150*a*-1 may be positioned closer to base openings 2116*a-d* or, alternatively, closer to inflow edge 2108. In still other examples, the locations of apertures 2150*a*-1 may vary relative to one another, such that some may be closer to inflow edge 2108 than others. Additionally, there may be multiple rows of apertures, namely, two or more rows of apertures.

Figure 17:
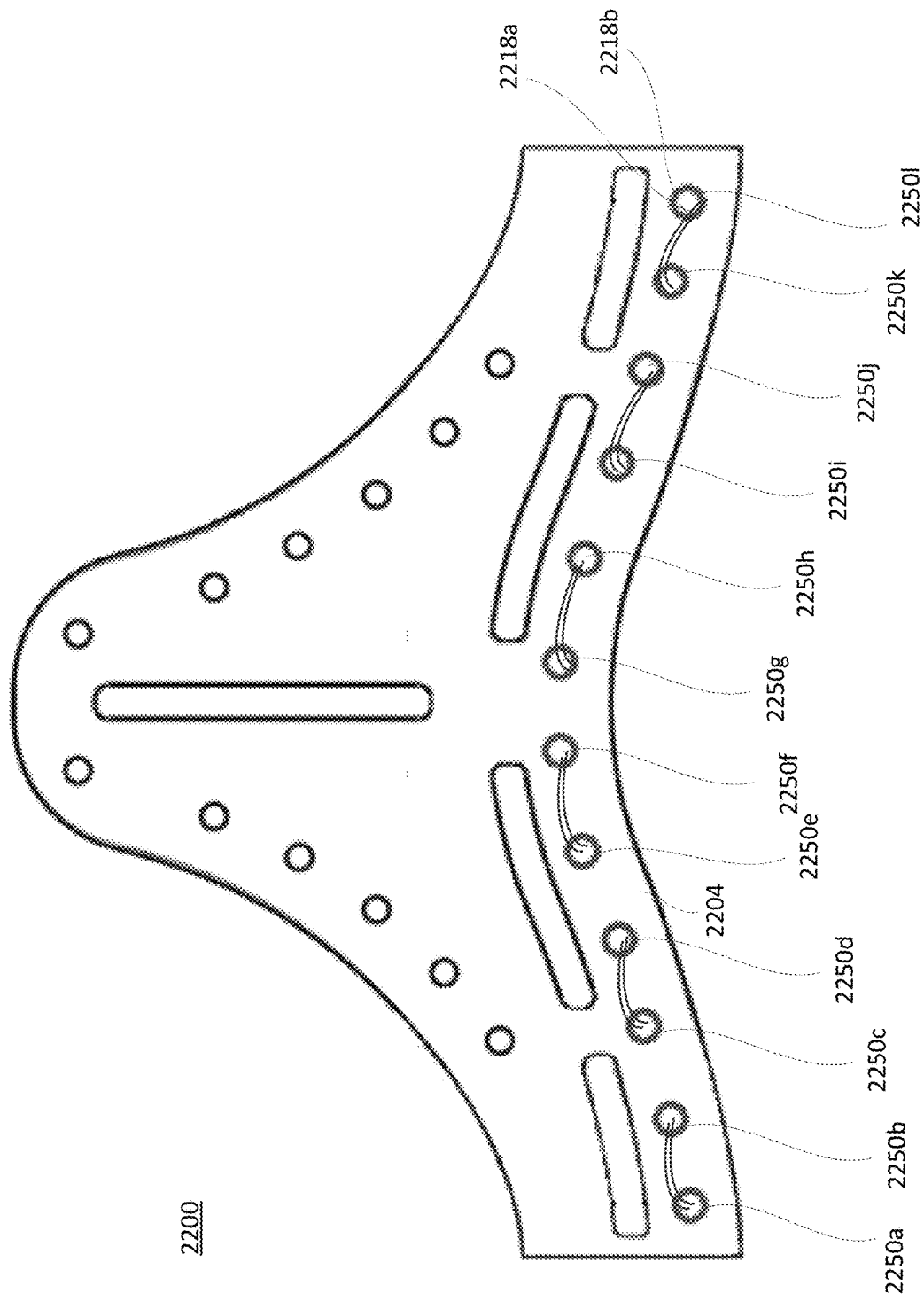
FIG. 17 is a view similar to FIG. 10 according to another embodiment thereof.

Any number of wires may be threaded through the apertures, provided the diameters of the respective wires can fit through the respective apertures. As shown in FIG. 17, frame 2200 includes apertures 2250*a*-22501. A first wire 2218*a* may be threaded through apertures 2250*a*-22501, as discussed with regard to FIG. 16, as may a second wire 2218*b*. Wires 2218*a* and 2218*b* may have a combined diameter that is less than the diameter of the apertures. Wires 2218*a* and 2218*b* may be threaded through the apertures in tandem, i.e., both wires may be threaded into the front and out from the rear of the same apertures. Alternatively, the wires may be offset by an aperture such that one wire is threaded into the front and out from the rear of one aperture, while the other wire is threaded into the front and out from the rear of the next adjacent aperture. Thus, in this latter embodiment, the wires will alternately be threaded into the front and out from the rear of every aperture, as discussed in connection with FIG. 11A. This may allow for the appearance of a continuous wire extending around base 2204. In still other arrangements, more than two sets of wires may be threaded through the apertures.

As previously discussed, during a TAVR procedure, some surgeons choose to crack the existing surgical valve prior to insertion of the replacement transcatheter valve. Cracking is not possible or is made more difficult when annular wire is wrapped around the circumference of the frame and the ends of the annular wire are tied together or secured to the frame in a way that makes it difficult to expand the diameter and size of the frame. To enable a surgeon to crack the frame, while still providing a structure that will enable the base to be visible on a fluoroscope or x-ray, the first and second ends of the wire may be left as free ends that are not attached or secured to one another, or may be very loosely attached to one another or to the frame. Some examples are discussed below.

Figure 18A:
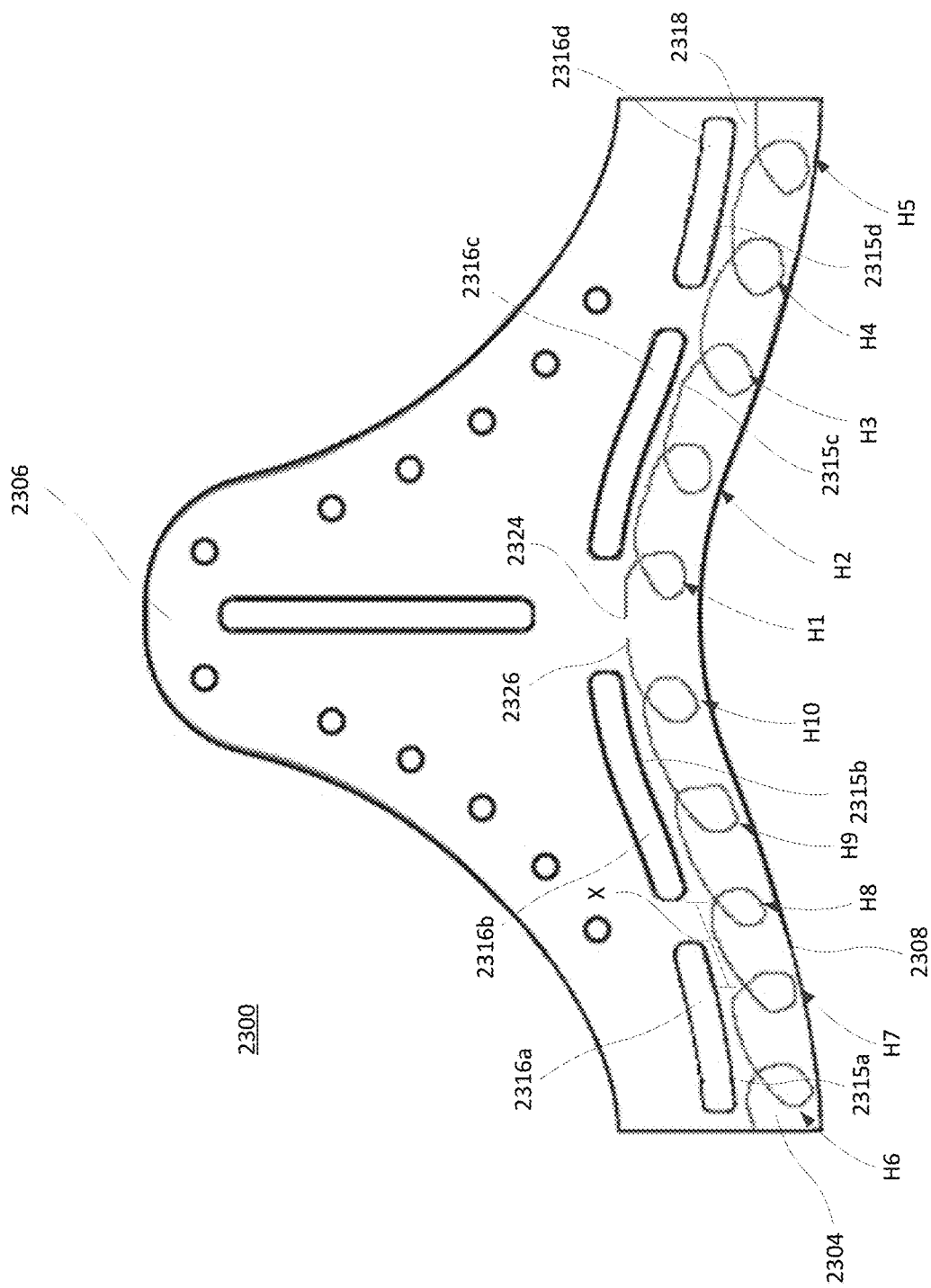
FIG. 18A is a view similar to FIG. 10 according to another embodiment thereof.

FIG. 18A is a fragmentary front view of a one-third section of a frame 2300 showing wire 2318 extending around the frame. It is to be appreciated that in a preferred example, wire 2318 extends around the entire periphery or circumference of frame 2300, but only a one-third section is shown for ease of discussion. Wire 2318 is positioned between the inflow edge 2308 and bottom edges 2315*a-d* of base openings 2316*a*-2316*d*. The first free end 2324 of wire 2318 is shown at a position below commissure post 2306. Wire 2318 may be wrapped around the circumference of frame 2300 in a flattened helical or looped pattern until reaching the second free end 2326 of the wire.

Any number of circular loops may be provided along each one-third portion of frame 2300. In this example, ten circular loops H1-H10 are positioned adjacent inflow edge 2308. The circular loops are continuous, with the end of one loop extending into the start of the next loop. In alternative examples, circular loops may be provided on only a one-third section of frame 2300, or only one or two circular loops may be provided on frame 2300. In other examples, the loops may take on any shape, such as square and triangular. Similarly, instead of loops, excess lengths of wire may be wrapped around the frame 2300 in any other shape or form so as to allow for expansion of the wire when frame 2300 is expanded.

The circular loops may be evenly spaced apart from one another by a pre-set distance X, depending on the desired number of circular loops to be provided on frame 2300. In other examples, the pre-set distance X between each circular loop may be increased or decreased, or the pre-set distance may vary between the loops rather than being uniform.

Once wire 2318 has been wrapped around the entire circumference of base 2304, first free end 2324 and second free end 2326 of wire 2318 remain spaced apart from one another. They are not intertwined or otherwise secured together. It is to be appreciated that even though the first and second free ends 2324, 2326 of wire 2318 are not secured together, the properties of the wire, such as the combination of strength and ductility, enable the wire to maintain its shape and position around the base, as well as remain releasably secured and attached to frame 2300. Additionally, during preparation of the valve, a cuff (FIG. 2) will extend over base 2304 of frame 2300 to help keep wire 2318 in position.

During a TAVR procedure, a previously implanted surgical valve having frame 2300 may be cracked by expanding a balloon or other expandable structure within the interior of the valve. During such expansion, the circular loops H in wire 2318 may get smaller as the wire "stretches" along with frame 2300. As a result of coiled loops H, wire 2318 will not inhibit the expansion of frame 2300, enabling both greater ease in cracking the frame and greater visibility of the frame during surgery.

Figure 18B:
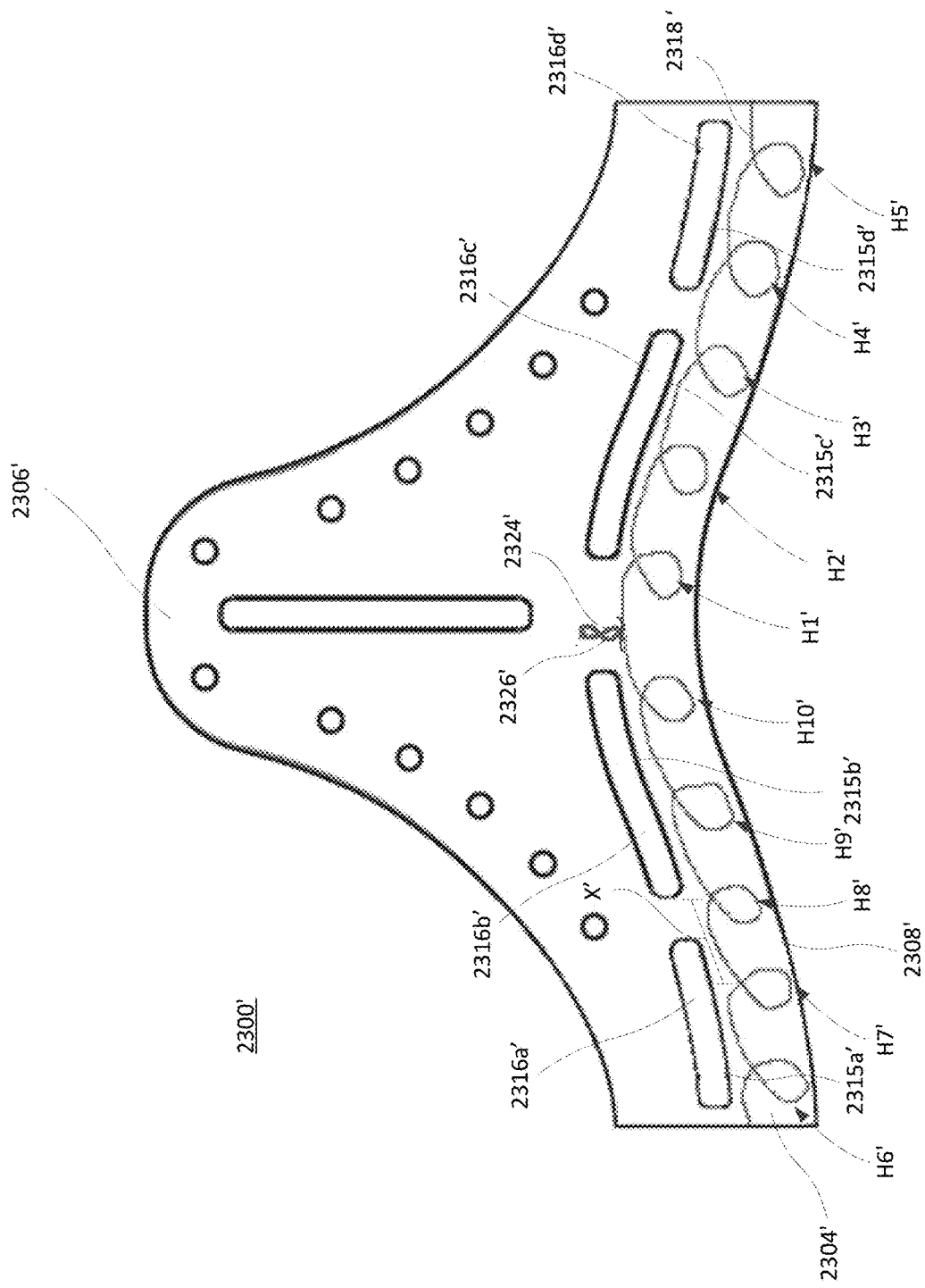
FIG. 18B is a view similar to FIG. 10 according to another embodiment thereof.

FIG. 18B illustrates another example which is similar to FIG. 18A, except that the first end 2324' and second end 2326' are secured together. FIG. 18B is a fragmentary front view of a one-third section of a frame 2300' showing wire 2318' extending around the frame. It is to be appreciated that in a preferred example, wire 2318' extends around the entire periphery or circumference of frame 2300', but only a one-third section is shown for ease of discussion. Wire 2318' is positioned between the inflow edge 2308' and bottom edges 2315a'-d' of base openings 2316a'-2316d'. The first end 2324' of wire 2318' is shown at a position below commissure post 2306'. Wire 2318' may be wrapped around the circumference of frame 2300' in a flattened helical or looped pattern until reaching the second end 2326' of the wire.

Any number of circular loops may be provided along each one-third portion of frame 2300'. In this example, ten circular loops H1'-H10' are positioned adjacent inflow edge 2308'. The circular loops are continuous, with the end of one loop extending into the start of the next loop. In alternative examples, circular loops may be provided on only a one-third section of frame 2300', or only one or two circular loops may be provided on frame 2300'. In other examples, the loops may take on any shape, such as square and triangular. Similarly, instead of loops, excess lengths of wire may be wrapped around the frame 2300 in any other shape or form so as to allow for expansion of the wire when frame 2300' is expanded.

The circular loops may be evenly spaced apart from one another by a pre-set distance X', depending on the desired number of circular loops to be provided on frame 2300'. In other examples, the pre-set distance X' between each circular loop may be increased or decreased, or the pre-set distance may vary between the loops rather than being uniform.

Once wire 2318' has been wrapped around the entire circumference of base 2304', first 'end 2324' and second end 2326' of wire 2318' may be secured to one another. In one example, as previously disclosed, they may be intertwined with one another or otherwise secured together. It is to be appreciated that even though the first and second ends 2324', 2326' of wire 2318' are not secured together, the properties of the wire, such as the combination of strength and ductility, enable the wire to maintain its shape and position around the base, as well as remain releasably secured and attached to frame 2300'.

As noted above, during a TAVR procedure and expansion of the frame, the circular loops H' in wire 2318 may get smaller as the wire "stretches" along with frame 2300. Even though first and second 2326' and 2326' are secured together, as a result of coiled loops H, wire 2318 will not inhibit the expansion of frame 2300, enabling both greater ease in cracking the frame and greater visibility of the frame during surgery. Additionally, during preparation of the valve, a cuff (FIG. 2) will extend over base 2304 of frame 2300 to help keep wire 2318 in position. With the first and second ends 2324', 2326' secured together, this can help to prevent the first and second ends 2324', 2326' from piercing through the cuff.

Figure 19A:
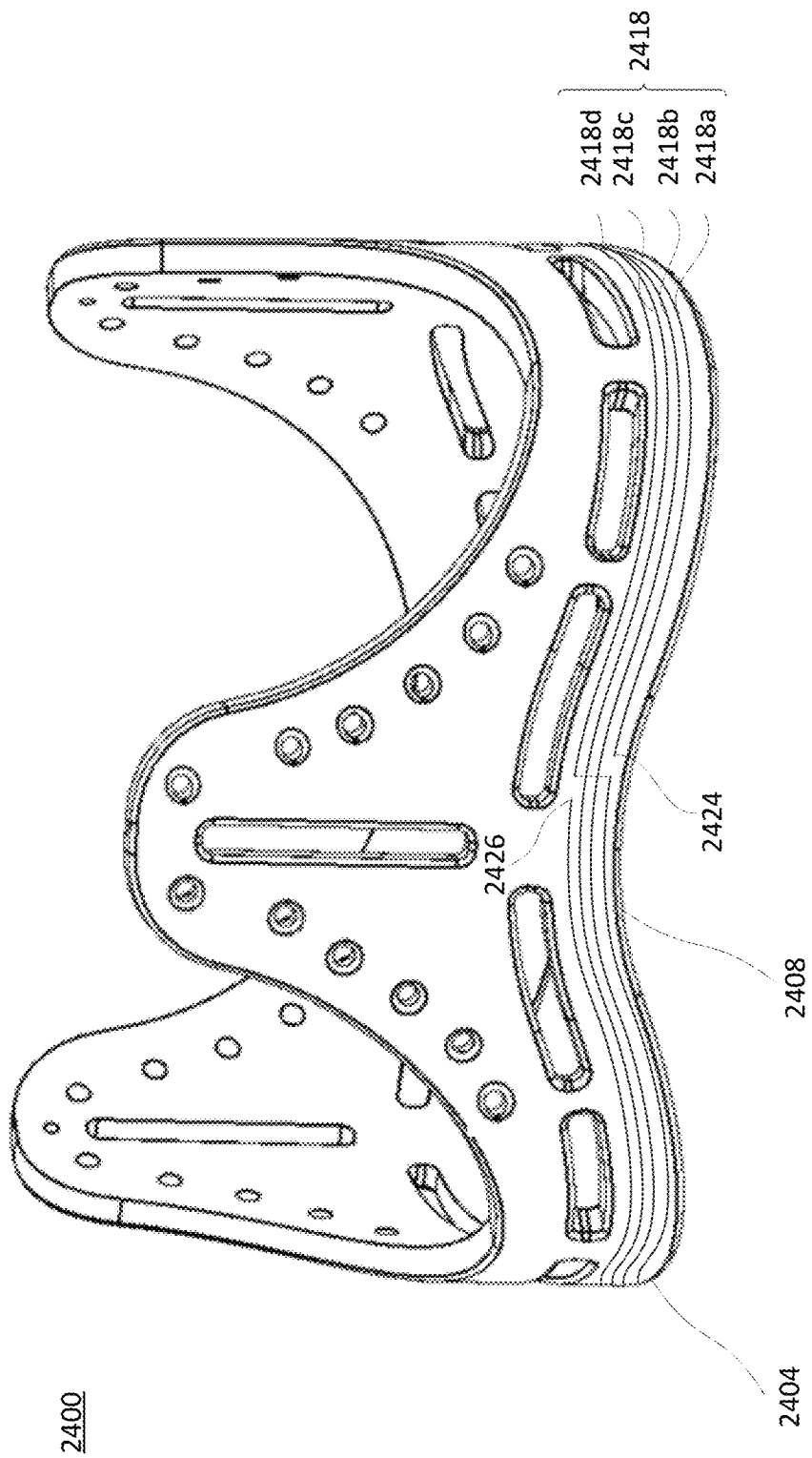
FIG. 19A is a perspective view of the frame of a surgical heart valve having radiopaque elements according to another embodiment of the disclosure.
Figure 19B:
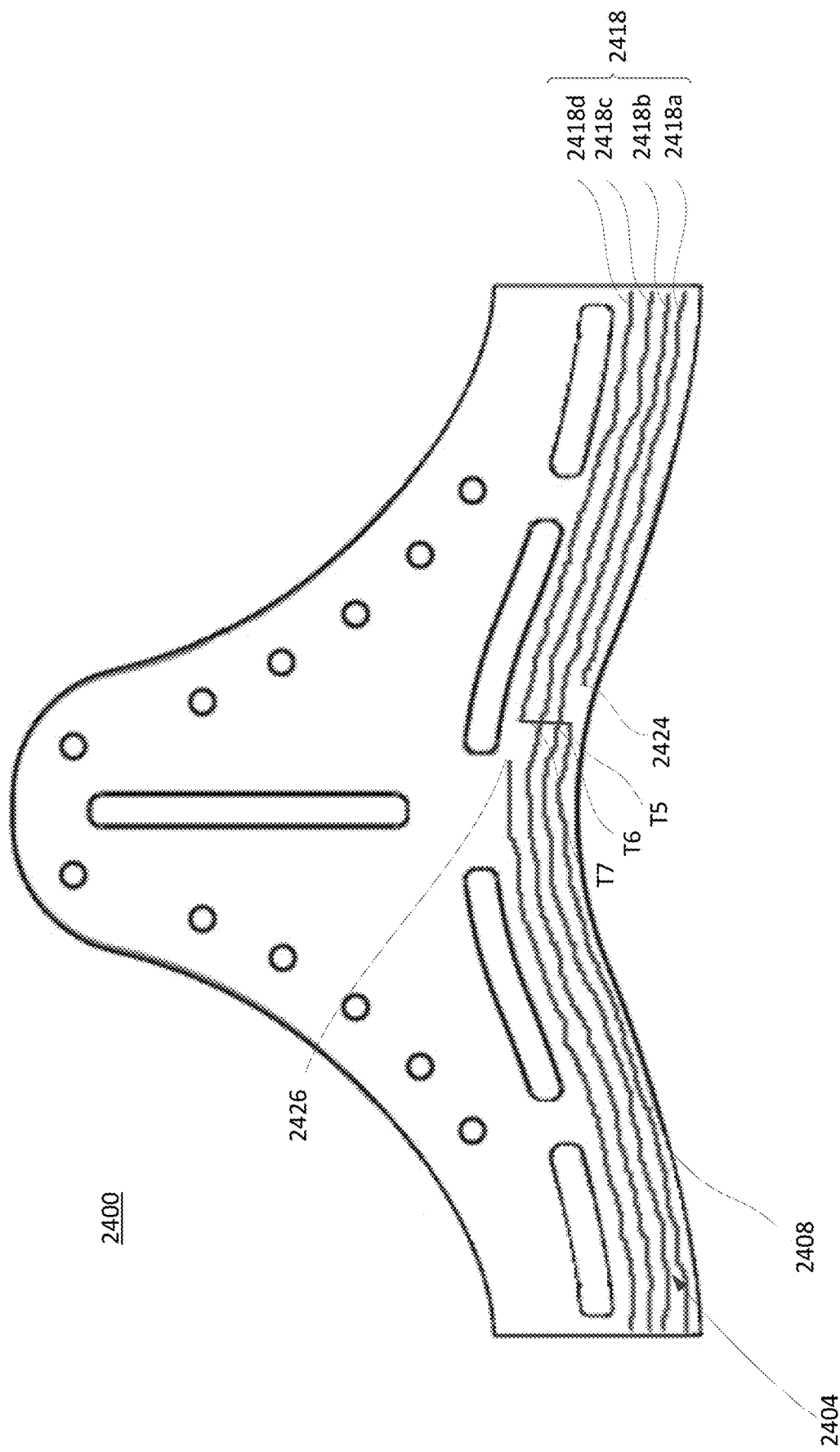
FIG. 19B is a fragmentary front view of a one-third section of the frame of FIG. 19A.

FIGS. 19A-19B illustrate another example frame 2400 in which the first and second ends of a wire are not secured together and remain free ends. The overall configuration is similar to the configuration shown in FIG. 15A, except that the first free end 2424 and second free end 2426 of wire 2418 are not secured to one another and spaced apart from one another to enable the frame to expand during a TAVR procedure. As shown in this example, wrapping of wire 2418 begins with first free end 2424 at a position closest to inflow edge 2408. Wire 2418 is wrapped in a horizontal direction around base 2404 of frame 2400 and generally follows the scalloped shape of inflow edge 2408. As with wire 2018 in FIGS. 15A-15B, a single wire continuously extends around base 2404 so that there is a first wire wrap 2418a, a second wire wrap 2418b, a third wire wrap 2418c, and a fourth wire wrap 2418. With reference to FIG. 19B, there is a length of wire that extends between each wire wrap to allow for a transition from one row or wire wrap to the next. As shown, there is a wire transition T5 between first wire wrap 2418a and second wire wrap 2418b; a wire transition T6 between second wire wrap 2418b and third wire wrap 2418c; and a wire transition T7 between third wire wrap 2418c and fourth wire wrap 2418d. Wire transitions T5-T7 are each lengths of wire that extend upward in a vertical direction, but it is to be appreciated that the transitions between any two wire wraps may be any desired shape or line that enables one continuous wire to be wrapped around the base 2404 of frame 2400.

After wire 2418 has been wrapped around base 2404, the second free end 2426 of the wire is not secured or tied to the first free end 2424 of the wire or to frame 2400. As a result, wire 2418 will be free to expand and will not inhibit the expansion of frame 2400 when cracking is desired.

Figure 20:
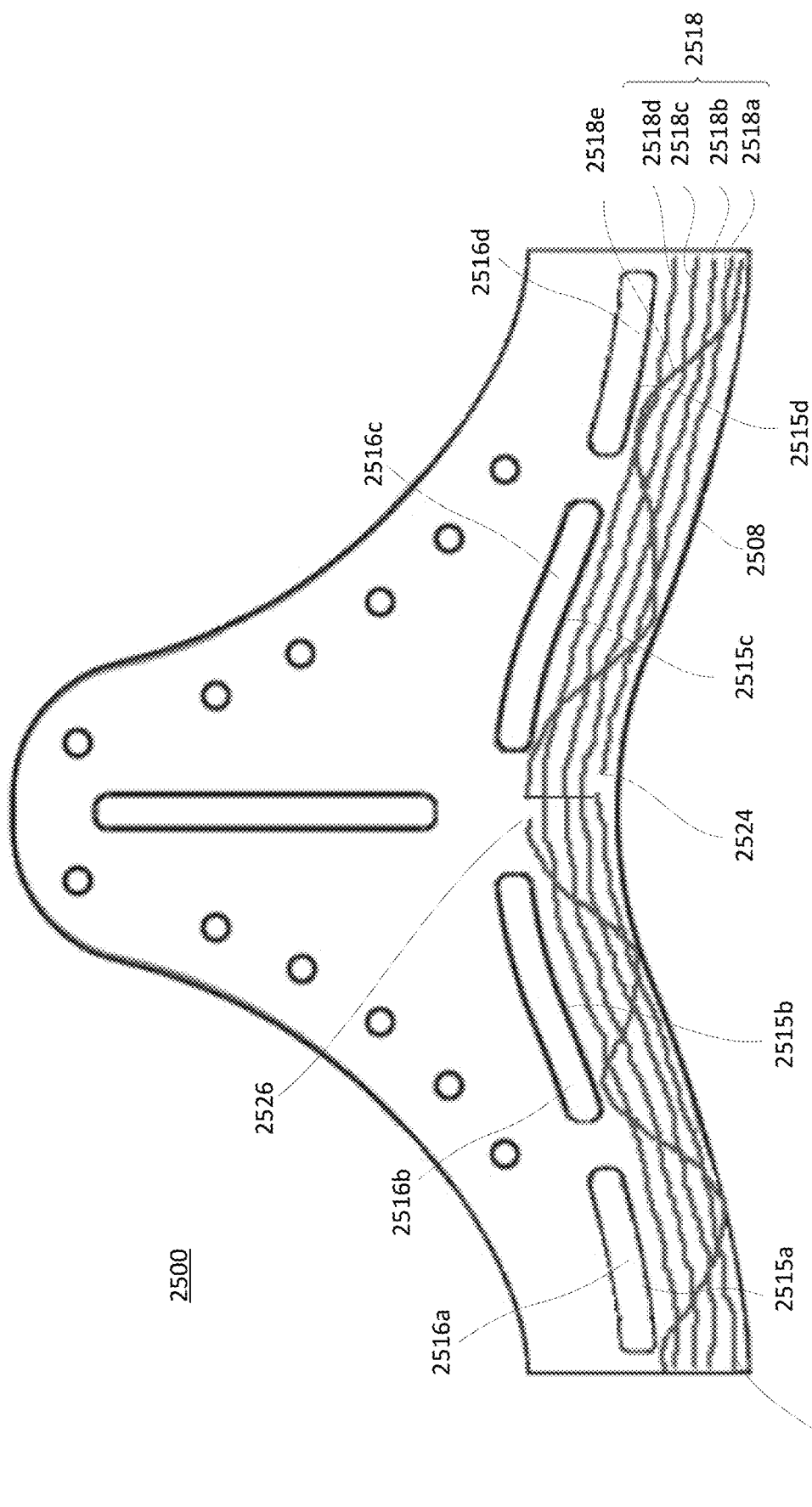
FIG. 20 is a view similar to FIG. 10 according to another embodiment thereof.

With reference to another example shown in FIG. 20, frame 2500 has a configuration similar to that of frame 2400 shown in FIGS. 19A-19B, and includes first through fourth wire wraps 2518a-2518d extending in a horizontal direction between inflow edge 2508 and the bottom edges 2515a-2515d of base openings 2516a-2516d. Frame 2500 differs from frame 2400 by including a fifth wire wrap 2518e that extends around one or more of the annular wraps 2518a-2518d. As shown, fifth wire wrap 2518e extends over the first through fourth wire wraps 2518a-2518d in a sinusoidal pattern around the entirety (not shown) of base 2504. This may further help to secure wire 2518 to frame 2500 prior to a cuff being provided thereon. Additionally, the first free end 2524 and the second free end 2526 of wire 2518 are not attached to one another or to frame 2500. The fifth wire wrap 2518e may take any variety of shapes or overlapping patterns, and may extend over a fewer number of the wire wraps, such as two or three wire wraps. In another example, fifth wire wrap 2518e may be weaved over and under any number of annular wire wraps to releasably secure wire 2518 to frame 2500.

The wires in FIGS. 19A, 19B, and 20, or any example in which the ends of the wire are not secured to each other, may be further secured adjacent the respective frames by the addition of the cuff and fabric overlying the frame during formation of the valve. The cuff and fabric will secure the wire to the frame. Alternatively, the wire may be weaved into the fabric or cuff that will overlie the frame.

Figure 20A:
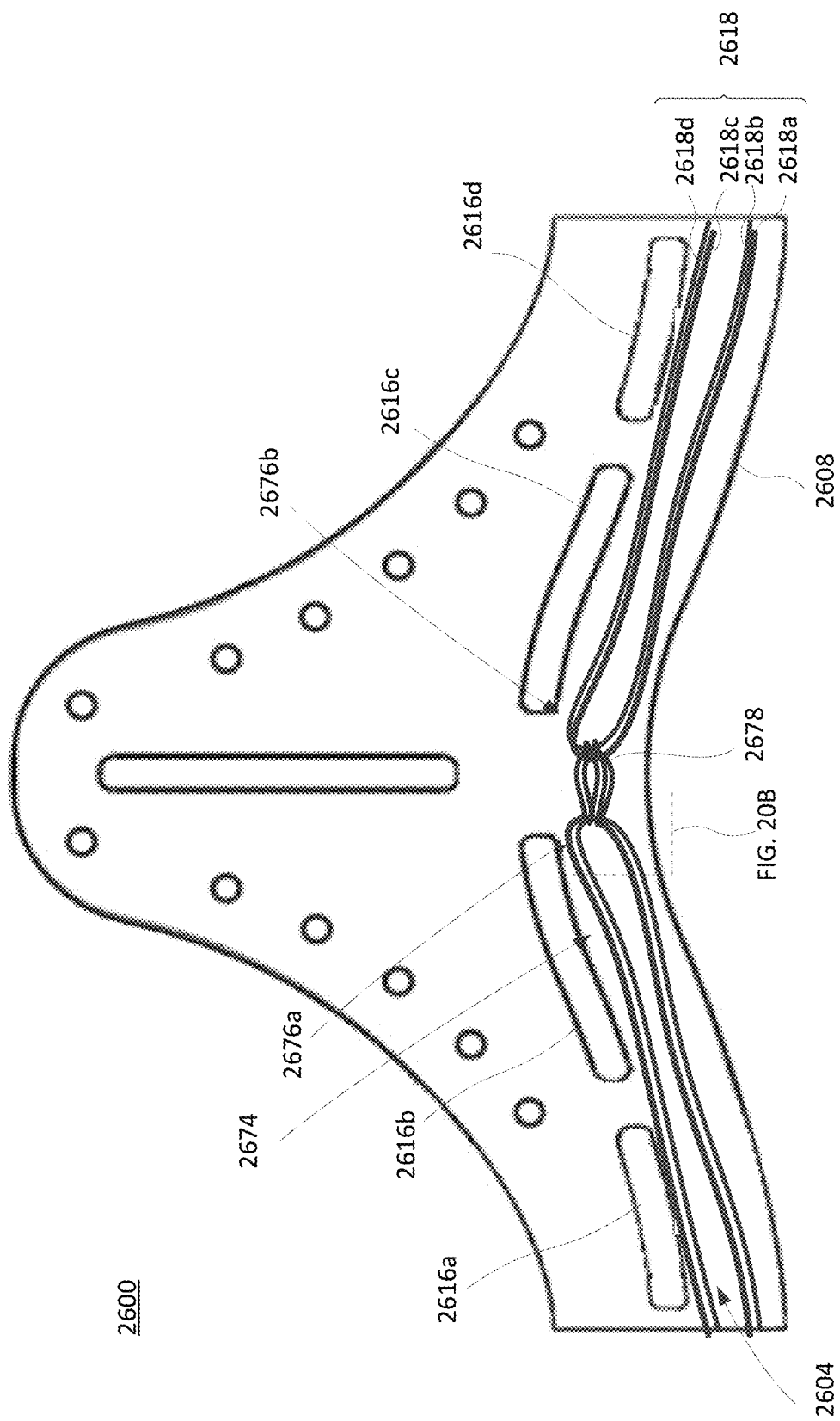
FIG. 20A is a view similar to FIG. 10 according to another embodiment thereof.
Figure 20B:
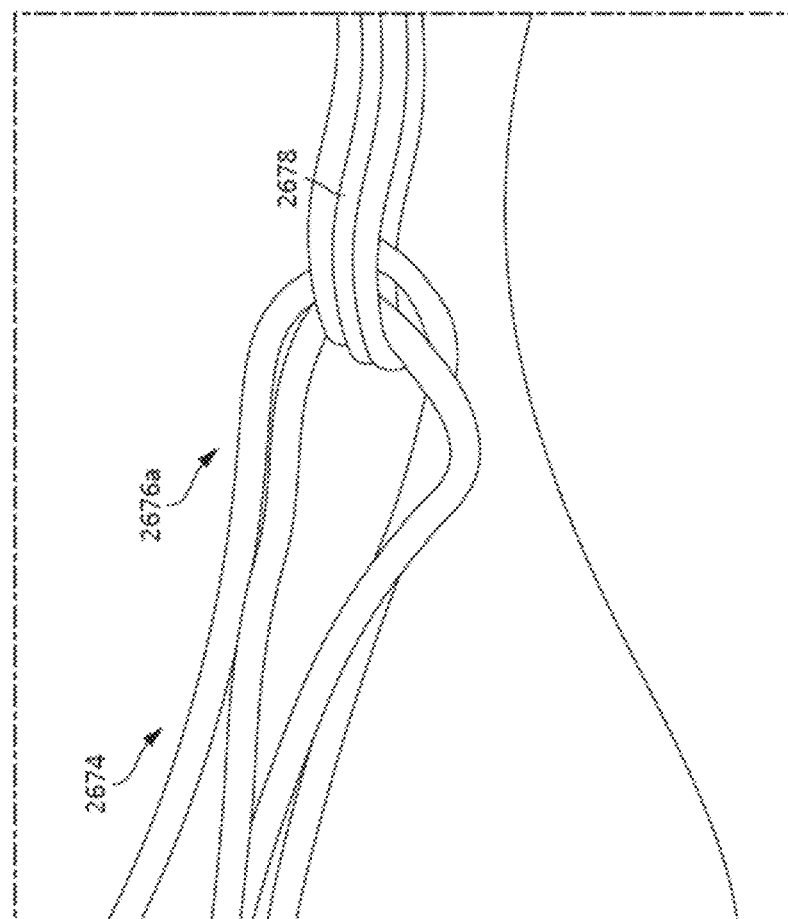
FIG. 20B is an enlarged portion of FIG. 20A.

Another alternative combination in which radiopaque elements are positioned on the base 2604 of a frame is illustrated in FIG. 20A, a one-third section of frame 2600. As shown, a radiopaque wire 2618 is provided at the base 2604 of frame 2600 in the form of a C-wrap 2674. The C-wrap 2674 extends around a portion of the circumference of base 2604 between the inflow edge 2608 of frame 2600 and base openings 2616a-2616d. As shown, in this example, the C-wrap includes a first wrap 2618a, a second wrap 2618b, a third wrap 2618c, and a fourth wrap 2618d that extend around the base 2604. The first looped end 2676a and the second looped end 2676b of the C-wrap 2674 can be joined together by a suture 2678. For example, the suture 2678 can be wrapped through the first and second looped ends 2676a, 2676b several times to secure the C-wrap 2674 against the frame 2600 and in this example arrangement, the suture 2678 is wrapped three times to secure the C-wrap. In other examples, the suture can be wrapped around one time, or more than one time. FIG. 20B shows an enlarged view of the portion of the C-wrap 2674 and the suture 2678 extending through the first looped end 2676a of the C-wrap 2674.

The C-wrap arrangement allows for the C-wrap, which in this example includes each of the first through fourth wire wraps 2618a, 2618b, 2618c, 2618d, to be tightly held and secured against the stent. This can help to prevent the wire wrap from interfering with the needle during sewing of the cuff. Additionally, this can be helpful during valve in valve replacement. In one example, once the valve has deteriorated, a balloon can be placed inside the valve and expanded to crack the frame 2600 for a valve in valve procedure, as disclosed herein. The suture 2678 connecting the first and second looped ends 2676a, 2676b of C-wrap 2674 can break upon balloon expansion, thereby allowing the frame 2600 to break and the annulus wire C-wrap 2674 and the frame 2600 to expand.

Figure 20C:
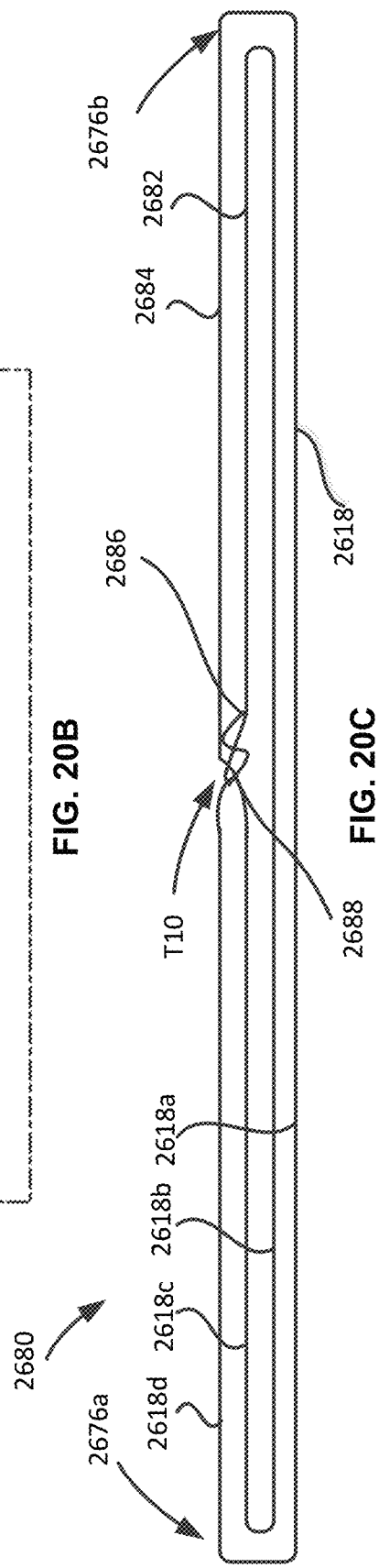
FIG. 20C is a schematic view of a the loop.

To create the C-wrap, a single radiopaque wire can be wrapped any number of times to form a closed loop that is in any desired pattern or shape. In one example, radiopaque wire 2618 is wrapped around a mandrel or other device(s) (not shown) to form a closed loop 2680 that is in the form of an elongated rectangle, as shown in FIG. 20C. The closed loop 2680 is formed by wrapping the radiopaque wire 2618 around the mandrel two times to form a first wire loop 2682 and a second wire loop 2684. A transition region T10 is further shown where the wire 2618 transitions between the first wire loop 2682 and the second wire loop 2684. In other examples, any shape of loop may be formed, such as circular or triangular. The leading first end 2686 of the radiopaque wire 2618 and the second end 2688 of the radiopaque wire 2618 can be twisted together, as in previous examples, to ensure that the ends of the radiopaque wire 2618 are secure. The closed loop 2680 can then be removed from the mandrel and then be wrapped around the annular base 2604 of frame 2600 to form a "C" shape around the annular base that includes four wire wraps 2618a, 2618b, 2618c, 2618d and first end 2676a and second end 2676b. As shown, because the "C" wrap 2674 is sized to extend around most, but not all, of the annular base 2604, the first and second looped ends 2676a, 2676b do not meet one another. Sutures 2678 can be threaded through the first end 2676a and second end 2676b of the elongated shape, as shown in FIG. 20A, to secure the C-wrap 2674 to the frame 2600. In other examples, the C-wrap frame is secured by three sutures, but multiple closed loops can be created. For example, four individual loops can be separately formed and stacked on top of one another. The four loops can be positioned around a portion of the base to form the C-wrap so that the first and second looped ends 2676a, 2676b of each loop do not extend all the way around the annular base and are spaced apart from one another. The first and second looped ends 2676a, 2676b of each loop may be secured to one another by sutures, thereby further securing the first, second third and fourth wire wraps 2618a, 2618b, 2618c, 2618d to the annular base 2604 of the frame.

Radiopaque Elements on Commissure Posts and Base of Frame

It is to be appreciated that any one of the aforementioned embodiments disclosing radiopaque elements on the commissure posts of a frame in FIGS. 3-14 may be combined with any one of the embodiments disclosing a frame with radiopaque elements on the base of frame in FIGS. 15A-20. This allows for radiopaque elements to be present on both the commissure posts and base of a frame, which in turn, provides for maximum visibility of the position of a surgical valve on an x-ray or fluoroscope. With this understanding, a few example combinations are described herein.

Figure 21:
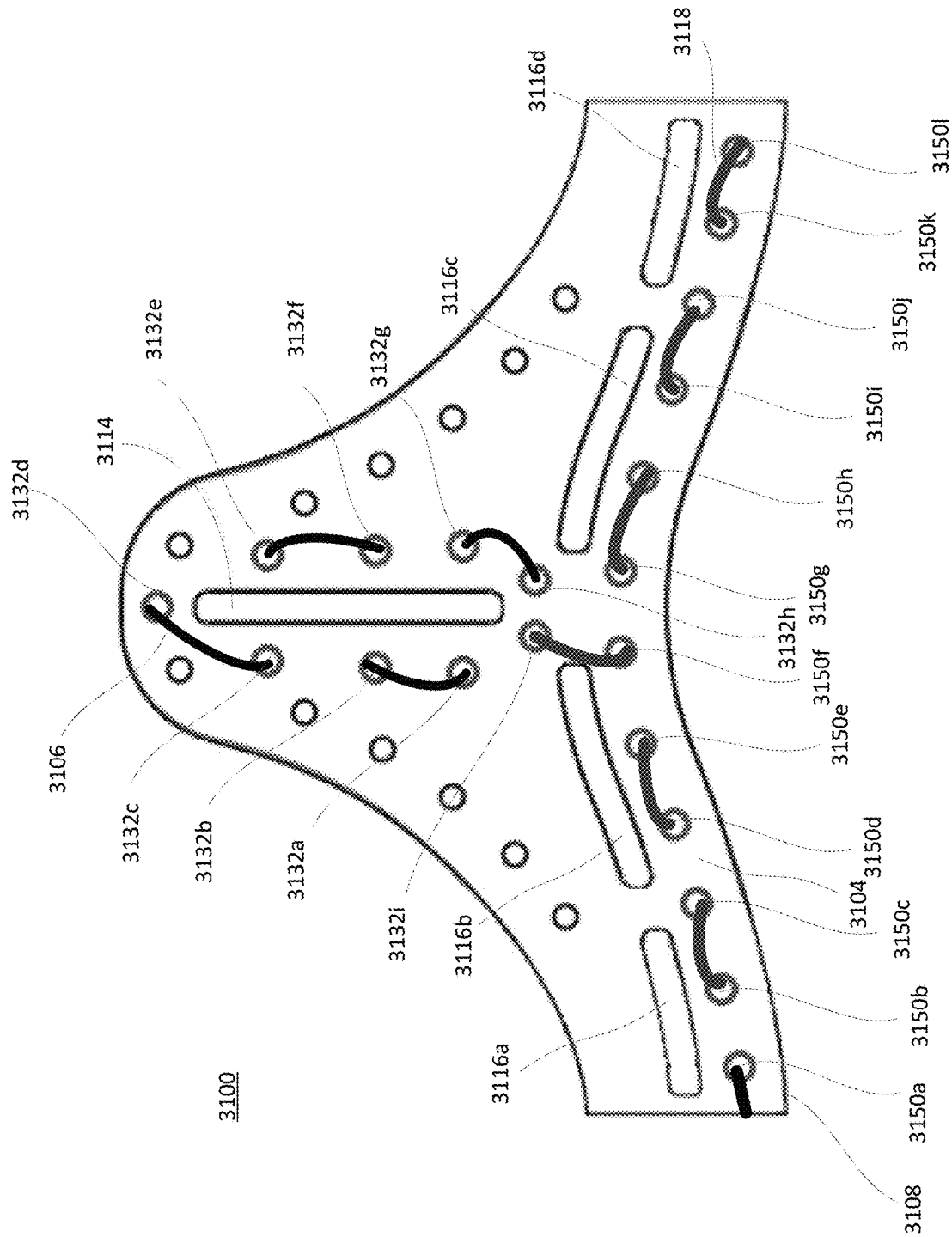
FIG. 21 is a view similar to FIG. 10 according to another embodiment thereof.

In one example, with reference to FIG. 21, a one-third section of frame 3100 is shown with radiopaque elements on both the commissure post 3106 and base 3104 of the frame. Apertures 3150a-3150l extend along base 3104 between inflow edge 3108 and base openings 3116a-3116d. Additional apertures 3132a-3132i are also positioned around central slot 3114 in commissure post 3106. Wire 3118 may be weaved into and out of each of the apertures, as in the previously described embodiments of FIGS. 8, 9A and 15A-15B.

A single wire may be weaved through each of the apertures on both commissure post 3106 and base 3104. Wire 3118 may continuously extend through apertures 3150a-3150f on base 3104, and then from aperture 3150f upwards to aperture 3132i on commissure post 3106. Wire 3118 may continue to weave into and out of apertures 3132a-3132h around commissure post 3106, and may then transition from aperture 3132h on the commissure post to aperture 3150g on base 3104. Wire 3118 may then weave through the remaining apertures 3150h-3150l on the base. The same wire apertures may be present on the remainder (not shown) of frame 3100, through which wire 3118 may extend. Alternatively, more than one wire may be used on frame 3100. For example, a first wire may be used in the apertures on base 3104, and a second wire may be used in the apertures on commissure post 3106. Multiple wires may also be woven in tandem through the same apertures, or individually through different apertures.

Figure 22:
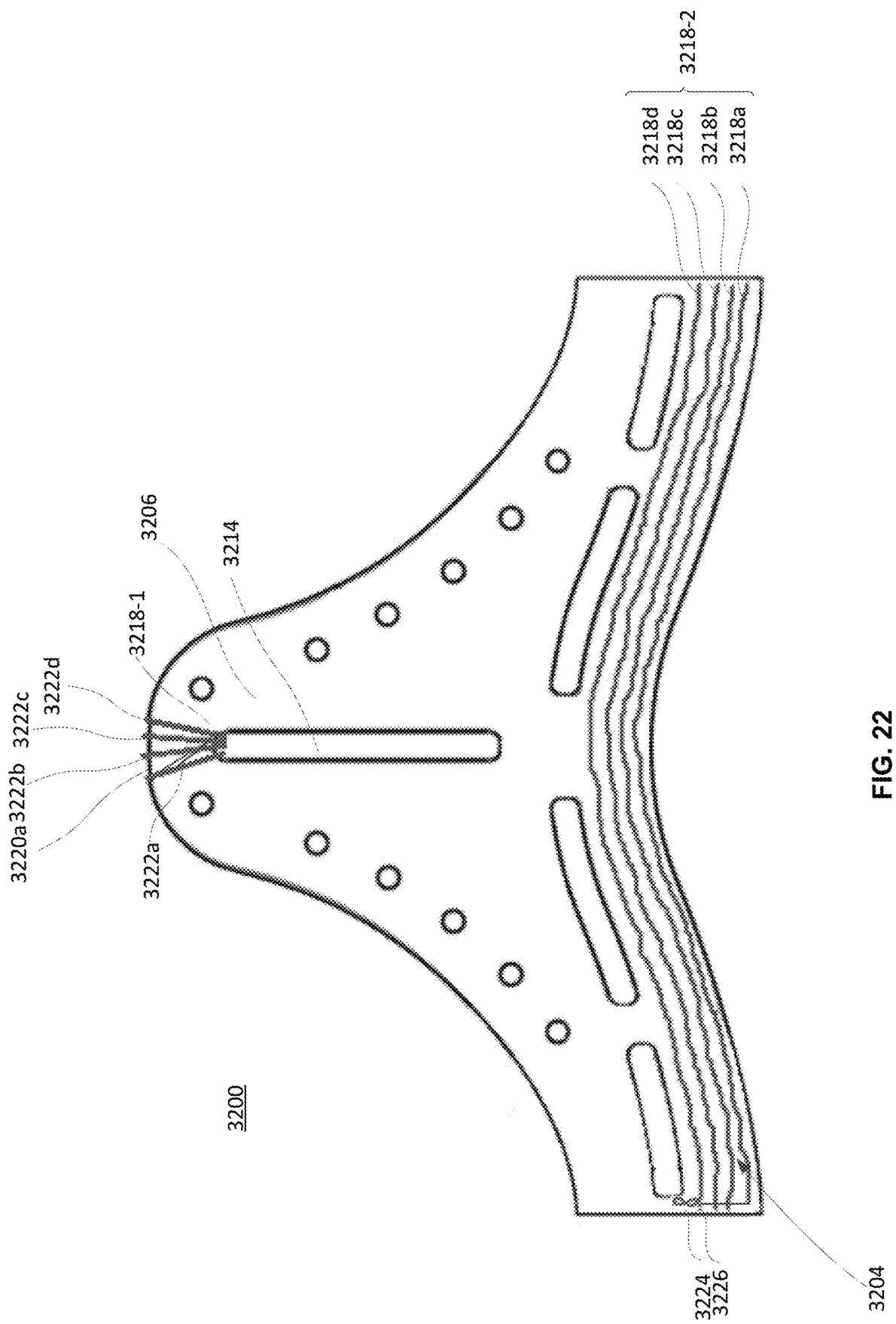
FIG. 22 is a view similar to FIG. 10 according to another embodiment thereof.

With reference to FIG. 22, a one-third section of frame 3200 is shown with radiopaque elements on both the commissure post 3206 and base 3204 of the frame. This example incorporates the examples of FIGS. 3-3A and 15A-15B, as described above, and the prior descriptions are equally applicable here. As shown, a first radiopaque wire 3218-1 extends around the tip 3220 of commissure post 3206 and through commissure post slot 3214. Wire 3218-1 is wrapped four times through commissure post slot 3214, such that there are four rays 3222a, 3222b, 3222c, and 3222d of wire 3218a-1 on commissure post 3206. A second wire 3218-2 is wrapped around the circumference of the base 3204 of frame 3200, as previously described herein. Wire 3218-2 includes a first wrap 3218a, a second wrap 3218b, a third wrap 3218c, and a fourth wrap 3218d, but any number of wraps may be utilized, including two or more wraps.

Figure 23:
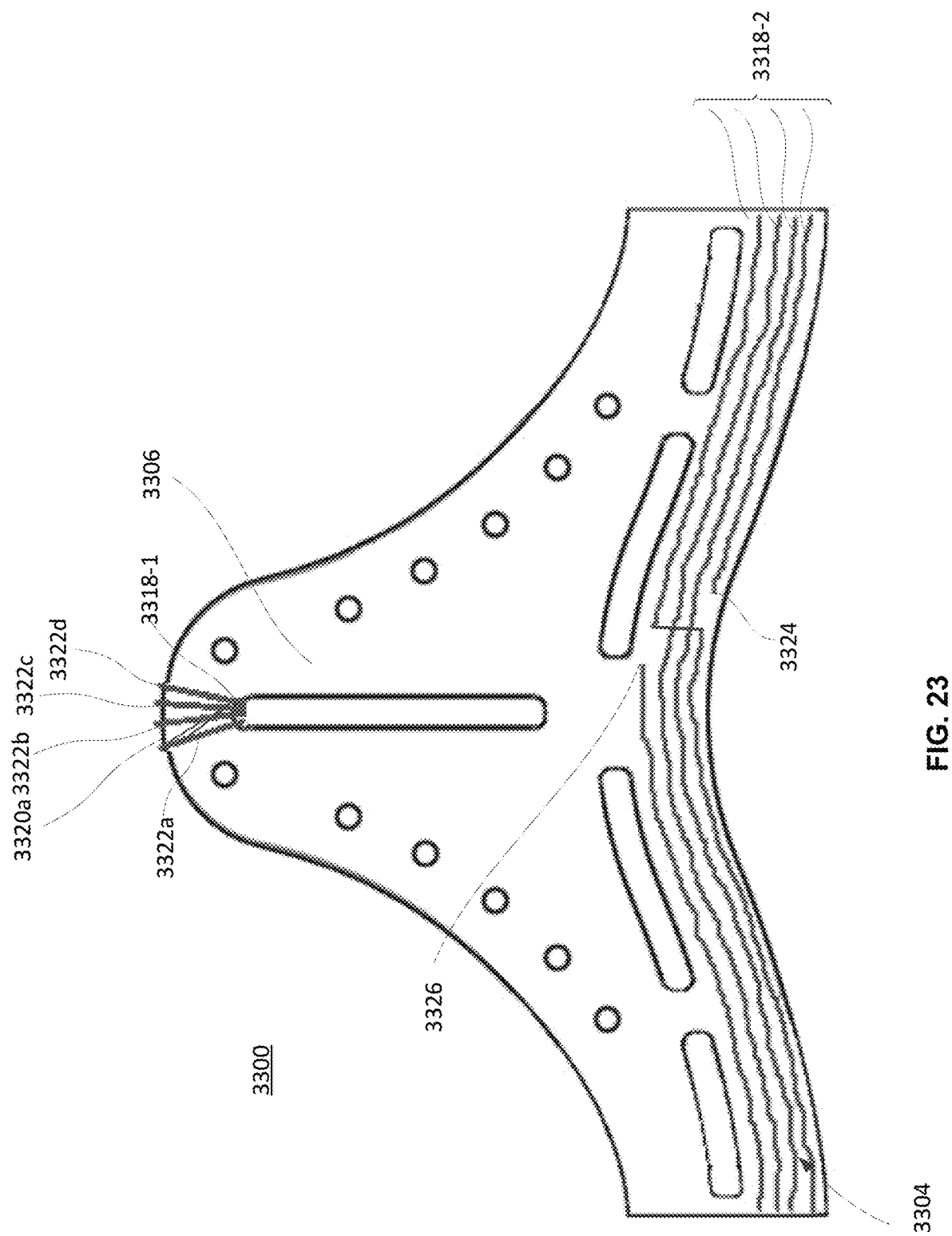
FIG. 23 is a view similar to FIG. 10 according to another embodiment thereof.

The first end 3224 and the second end 3226 of wire 3218-2 may be intertwined with one another to secure the wire to frame 3200, such as in any one of the configurations shown in FIGS. 4A-7B, or any configuration that would help to secure wire 3218-2 to the frame. Alternatively, as shown in FIG. 23, wire 3318-2 around the base 3304 of an alternative frame 3300 may be wrapped so that first free end 3324 and second free end 3326 of the wire are spaced apart from one another and not secured together. As discussed in more detail with regard to corresponding FIGS. 19A-19B, the first free end 3324 and the second free end 3326 of wire 3318-2 allow for expansion of frame 3300 when it is desired to crack the frame. Frame 3300 also includes first through fourth wire wraps 3322a-3322d of wire 3318-1 around the tip 3320 of commissure post 3306.

Figure 24A:
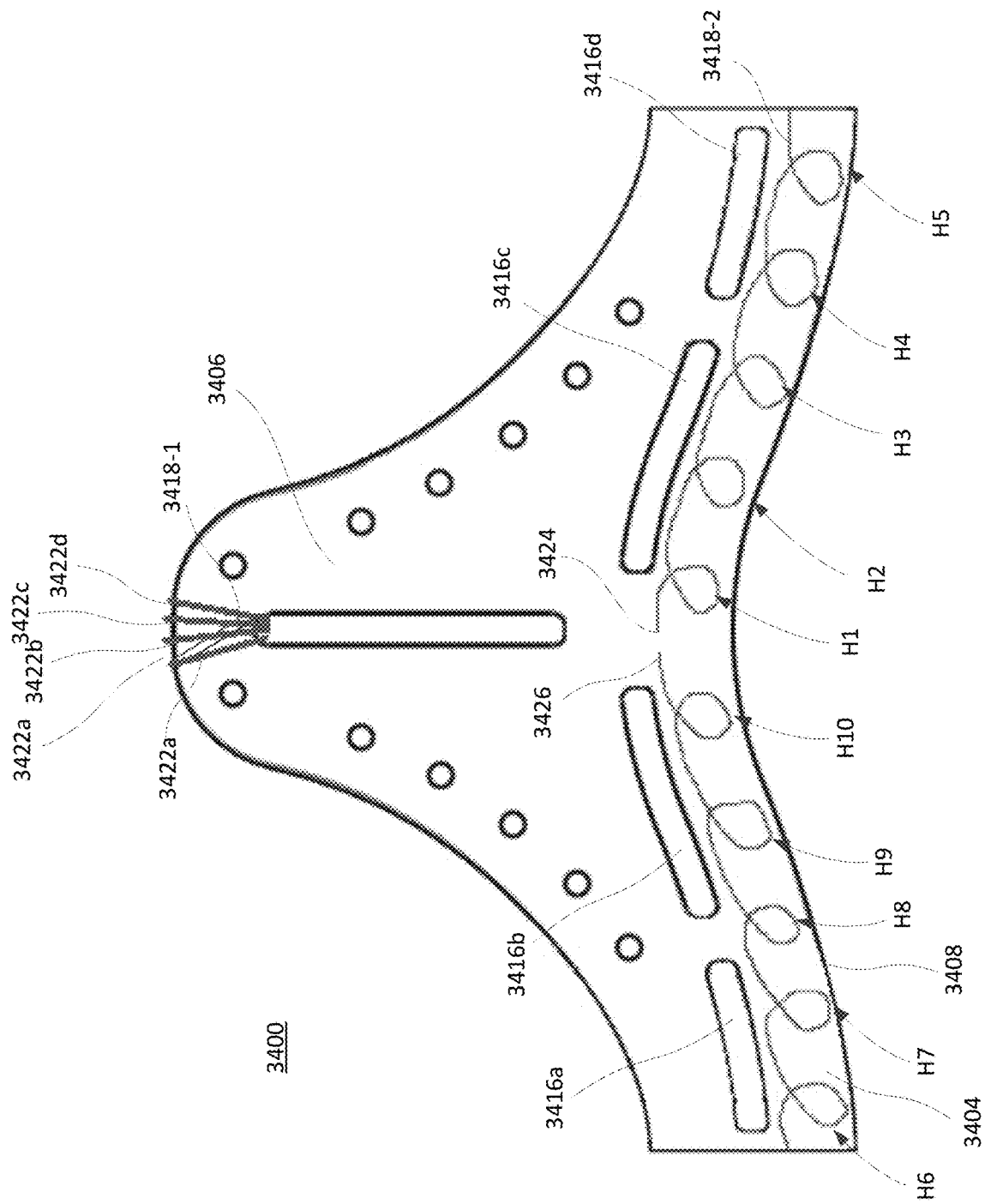
FIG. 24A is a view similar to FIG. 10 according to another embodiment thereof.

Another alternative combination in which radiopaque elements are positioned on both the commissure post and base of a frame is shown in FIG. 24A. Frame 3400 illustrates first through fourth wire wraps 3422a-3422d of wire 3418-1 extending around the tip 3420 of commissure post 3406, such as previously described. Additionally, wire 3418-2 positioned between the inflow edge 3408 of frame 3400 and base openings 3416a-3416d extends around base 3404 in a flattened helical or looped pattern. As shown, there are ten circular loops H1-H10 extending across the one-third portion of the illustrated base 3404. The first end 3424 and second end 3426 of wire 3418-2 at base 3404 are shown as free ends, but in other examples may be secured together, as discussed below with regard to FIG. 24A. In other examples, the loops may take on any shape, such as square and triangular. Similarly, instead of loops, excess lengths of wire may be wrapped around the frame 3400 in any other shape or form so as to allow for expansion of the wire when frame 3400 is expanded.

Figure 24B:
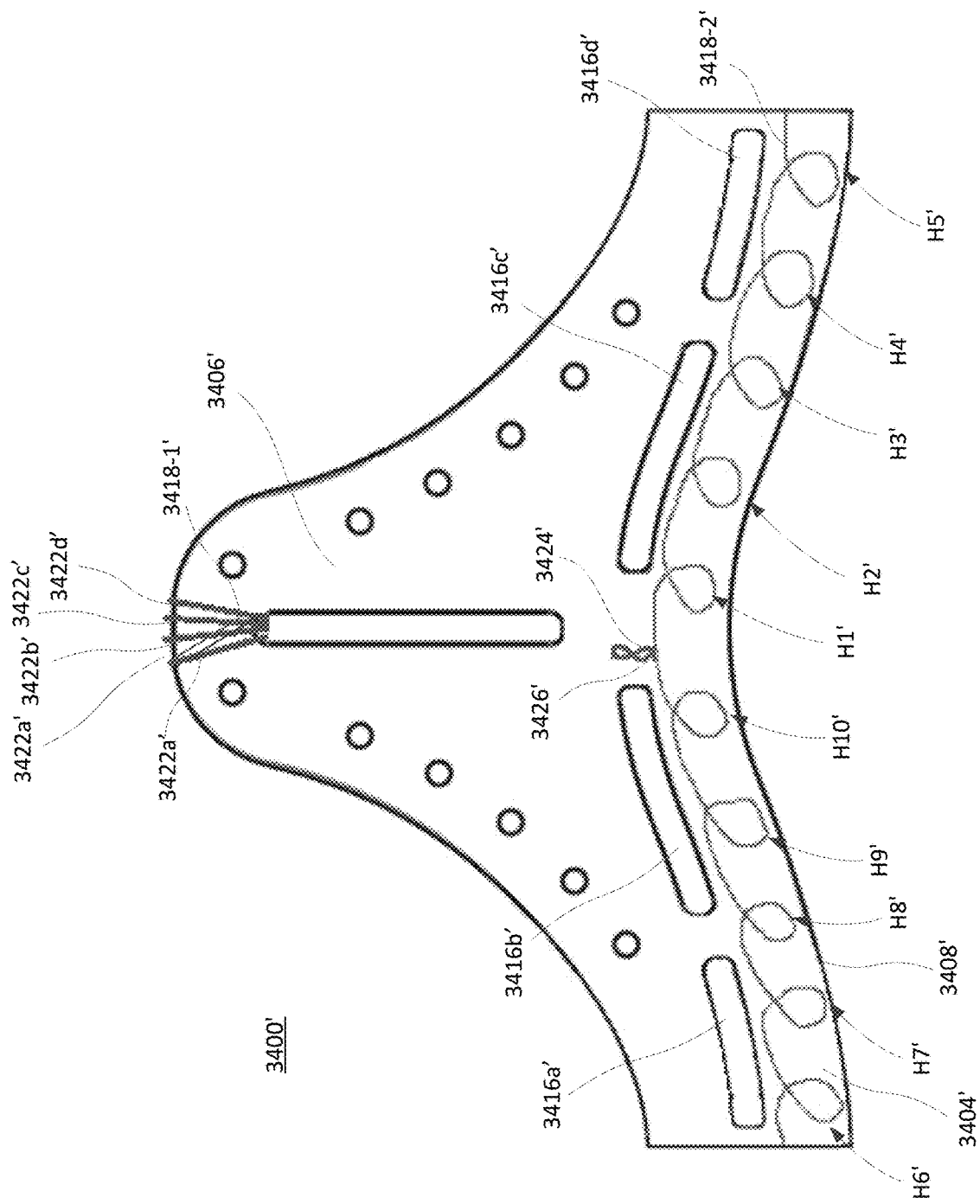
FIG. 24B is a view similar to FIG. 10 according to another embodiment thereof.

Another alternative combination in which radiopaque elements are positioned on both the commissure post and base of a frame is shown in FIG. 24B. Frame 3400' is identical to frame 3400 in FIG. 24A, except that the first free end 3424' and second free end 3426' of wire 3418-2' are secured together. Frame 3400' similarly illustrates first through fourth wire wraps 3422a'-3422d' of wire 3418-1' extending around the tip 3420' of commissure post 3406', such as previously described. Additionally, wire 3418-2' positioned between the inflow edge 3408' of frame 3400' and base openings 3416a'-3416d' extends around base 3404' in a flattened helical or looped pattern. As shown, there are ten circular loops H1'-H10' extending across the one-third portion of the illustrated base 3404'. The first end 3424' and second end 3426' of wire 3418-2' at base 3404' are intertwined together. In other examples, the loops may take on any shape, such as square and triangular. Similarly, instead of loops, excess lengths of wire may be wrapped around the frame 2300 in any other shape or form so as to allow for expansion of the wire when frame 2300' is expanded.

Figure 24C:
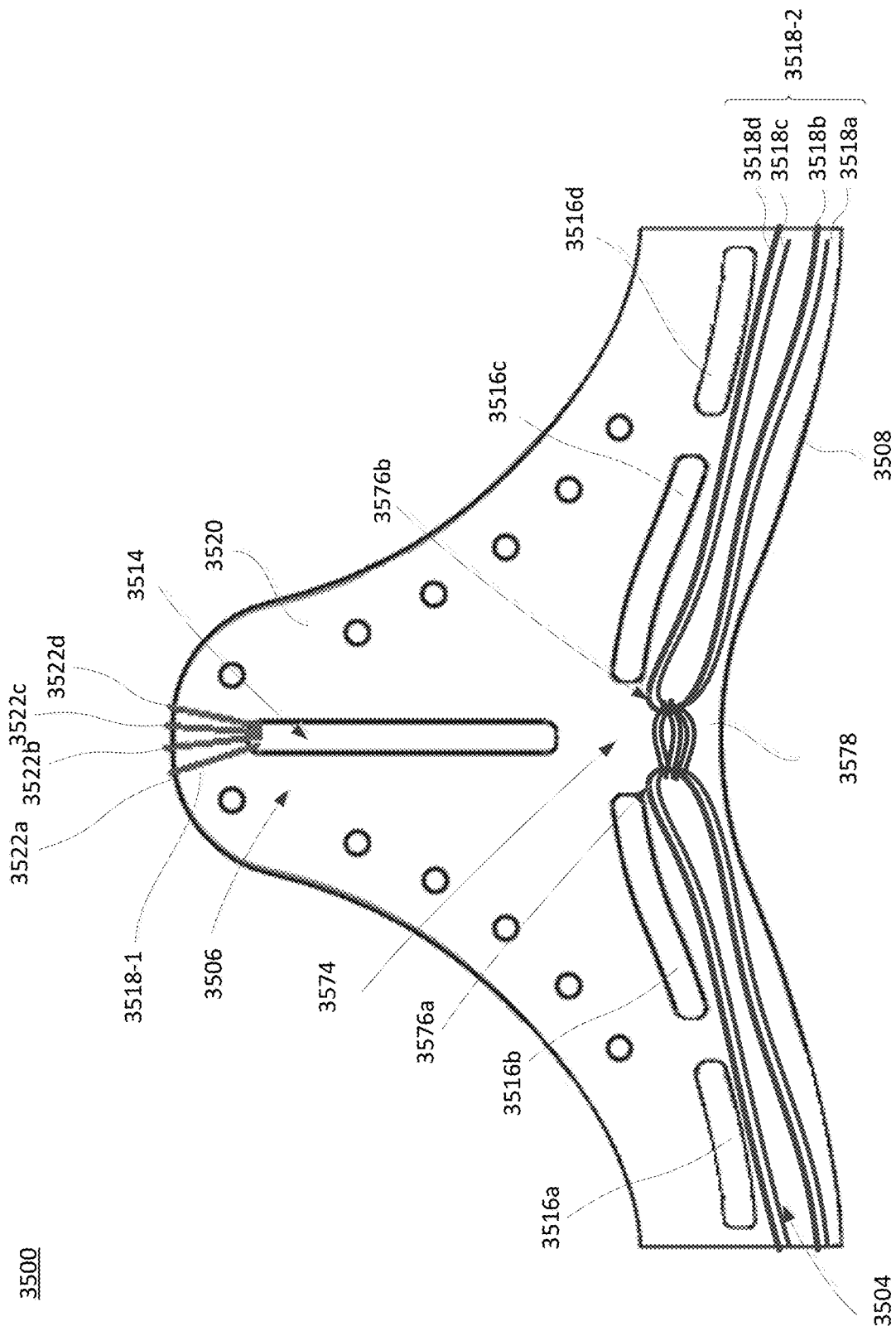
FIG. 24C is a view similar to FIG. 10 according to another embodiment thereof.

Another alternative combination in which radiopaque elements are positioned on both the commissure post 3506 and the base 3504 of a frame is illustrated in FIG. 24C, a one-third section of frame 3500. As shown, a first radiopaque wire 3518-1 extends around the tip 3520 of commissure post 3506 and through commissure post slot 3514. As in the prior examples, first radiopaque wire 3518-1 is wrapped four times through commissure post slot 3514 and around the tip 3520, such that there are four rays 3522a, 3522b, 3522c, and 3522d of wire 3518-1 on commissure post 3506, but any number of wraps may be provided. A second wire 3518-2 can optionally or additionally be provided at the base 3504 of frame 3500 in the form of a C-wrap 3574.

The C-wrap 3574 extends around a portion of the circumference of base 3504 between the inflow edge 3508 of frame 3500 and base openings 3516a-3516d. As shown, in this example, the C-wrap includes a first wrap 3518a, a second wrap 3518b, a third wrap 3518c, and a fourth wrap 3518d that extend around the base 3504. The first end 3576a and the second end 3676b of the C-wrap 3574 are joined together by a suture 3578. For example, the suture 3578 can be wrapped through the first and second looped ends 3576a, 3576b several times to secure the C-wrap 3574 against the frame 3600. In this example, the sutures are shown being wrapped four times through the first and second ends 3576a, 3576b, but in other examples, the suture may alternatively be wrapped through the ends one time, two times, three times, or more than four times.

Radiopaque Elements to Indicate Both Size and Location of Frame

As previously described, prior to a TAVR procedure, the surgeon must understand the size of the structurally deteriorated surgical valve to determine the appropriate transcatheter valve to implant. According to aspects of the disclosure, one way for a surgeon to better understand the size of the surgical valve is to have a radiopaque indicator on the frame of the surgical valve itself to indicate the size of the frame. This may allow a surgeon to confirm the frame size indicated in the patient's medical records, or readily identify the size of the frame when no medical or other records of the frame size exist. The manufacturer of the surgical valve frame may create any system in which a radiopaque symbol, character or the like on the frame correlates to the frame size.

One example of such a radiopaque system is the use of a pre-set number of radiopaque indicators, such as beads, knots, or other indicators, that correlate to a particular frame size. For example, a frame with one radiopaque indicator may indicate a 21 mm frame and a frame with two radiopaque indicators may indicate a 23 mm frame. This progression may continue up through the highest valve size available.

FIG. 25 illustrates an example frame 4100 with radiopaque indicators identifying the frame size. Frame 4100 is otherwise similar to the embodiment of FIGS. 15A-15B, except for the presence of radiopaque knots on one or more of the annular wire wraps. As in the embodiment of FIGS. 15A-B, frame 4100 includes four wraps 4118a-4118d of wire 4118 extending along the base 4104 and adjacent the inflow edge 4108 of frame 4100. Seven knots K1, K2, K3, K4, K5, K6 and K7 are provided on the fourth wrap 4118d of wire 4118, but may be provided on any one of the four wraps 4118a-4118d. Knots K1-K7 act as radiopaque indicators of the size of frame 4100.

Knots K1-K7 are shown evenly spaced apart from one another along the fourth wrap 4118d of wire 4118, but in other examples, the spacing of the knots may vary widely. For example, the knots may be spaced closer to one another, such that they are closely adjacent one another on one side of base 4104, or the spacing between individual knots may vary.

Figure 26:
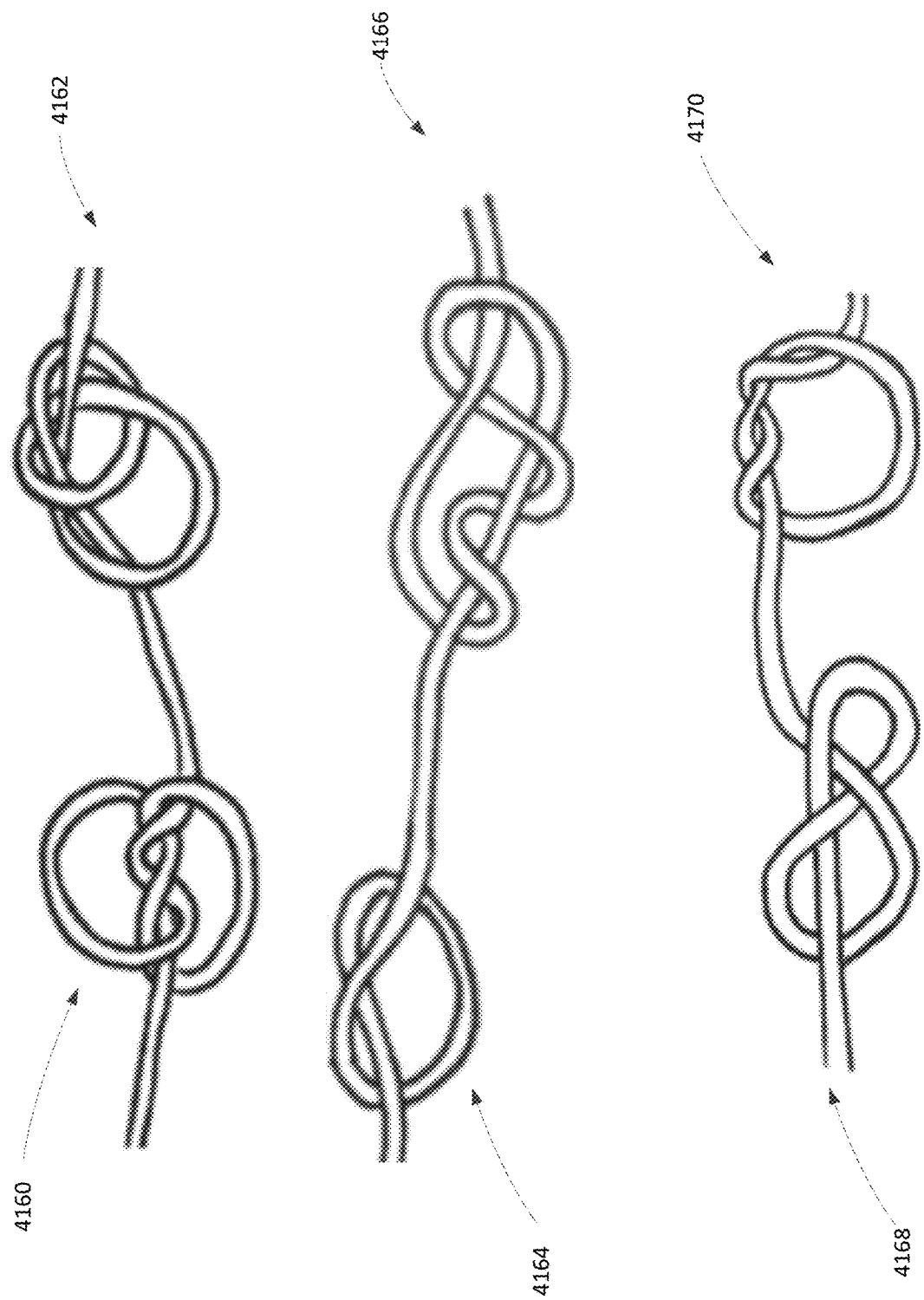
FIG. 26 are views of alternative knots that can be used in connection with a frame according to other embodiments.

The knots may be tied directly into the length of wire 4118. As the fourth wire wrap 4118d is wrapped around base 4104, each knot may be tied directly into the wire. Alternatively, a predetermined length of wire may be prepared ahead of time with the appropriate number and spacing of knots. Still further, knots K1-K7 may be formed from separate wires individually tied in knots to wire 4118. Any style of knot may be utilized on wire 4118. Several known knots, for example, are shown in FIG. 26 and include, without limitation, double 3-ply knot 4160, single 3-ply knot 4162, overhand knot 4164, Steve Dore knot 4166, FIG. 8 knot 4168 and double overhand knot 4170.

Figure 27:
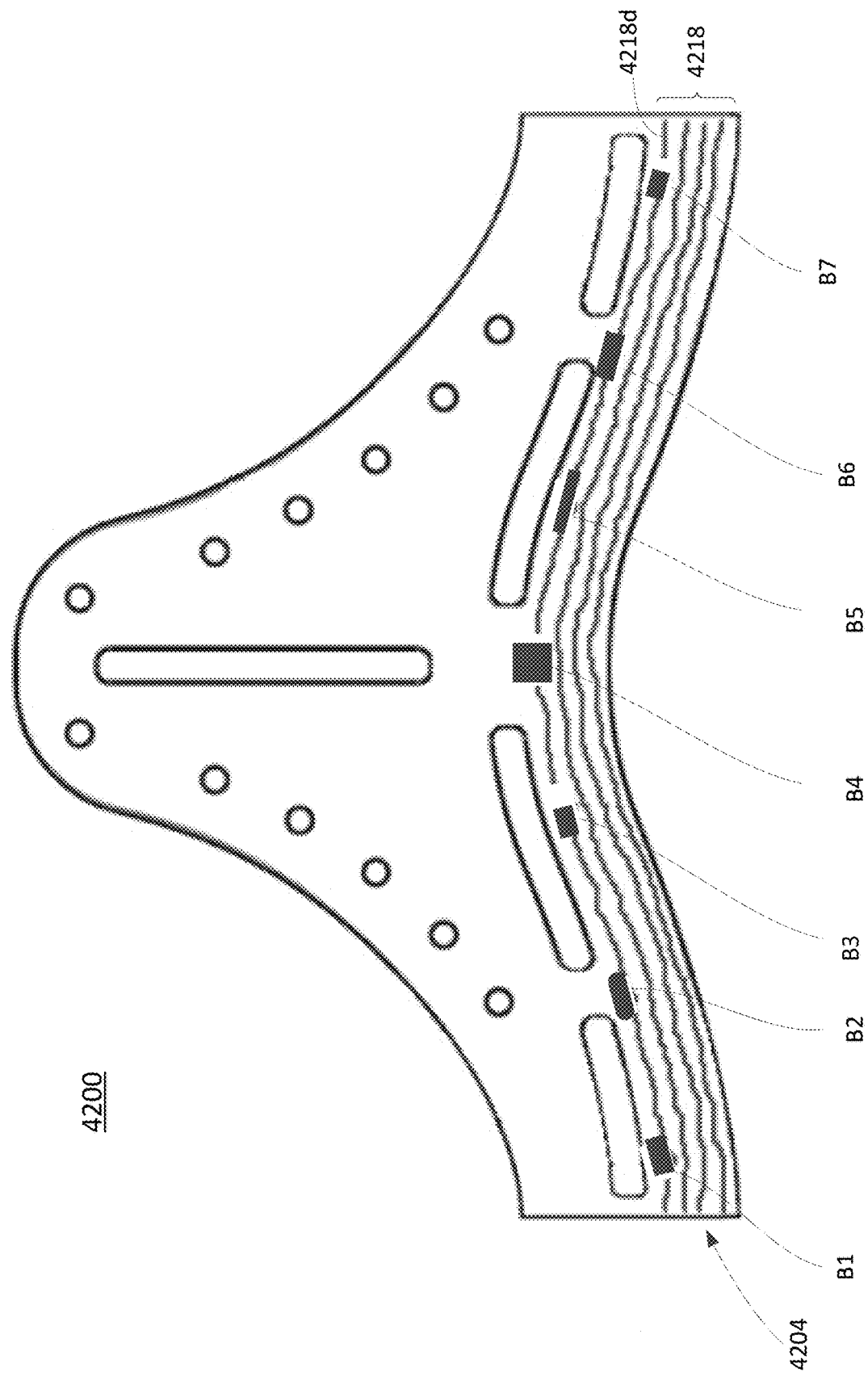
FIG. 27 is a view similar to FIG. 10 according to another embodiment thereof.

In another example system, instead of tying knots onto the annular wire, any number of external radiopaque elements may be secured to the wire. FIG. 27 illustrates a one-third section of an alternative frame 4200 in which seven radiopaque beads B1-B7 are attached to wire 4218. In this example, instead of using knots, radiopaque beads on wire 4218 may be used to represent a pre-set valve size. It is to be appreciated that any other type of radiopaque feature may be attached to the annular wire or frame itself to indicate frame size.

Each of the beads B1-B7 may have a central bore or lumen (not shown) through which wire 4218 may pass. As the fourth wrap 4218d is wrapped around base 4204, each radiopaque bead B1-B7 may be deposited onto the wire. Alternatively, fourth wrap 4218d may be a separate and individual wire wrap with beads thereon. In this example, the beads are loose and capable of moving relative to one another. In other examples, each of beads B1-B7 may be secured in place such as by tying a knot at each end of the bead, or by looping the wire through the bead twice so as to capture the bead by the wire. Alternatively, an adhesive may be used to secure the bead in place, an alternative bead that snaps onto the wire and remains secured in place may be used, or other known arrangements may be used to secure the beads in place on the wire.

The beads may have any shape or size, provided they are at least partially comprised of or coated with a radiopaque material, including those radiopaque materials describe above. For example, referring to FIG. 27, bead B1 has a large rectangular shape; bead B2 has an oval pill-shape; bead B3 has a smaller rectangular shape; bead B4 has a square shape; and bead B5 has an elongated and thin rectangular shape.

Figure 28:
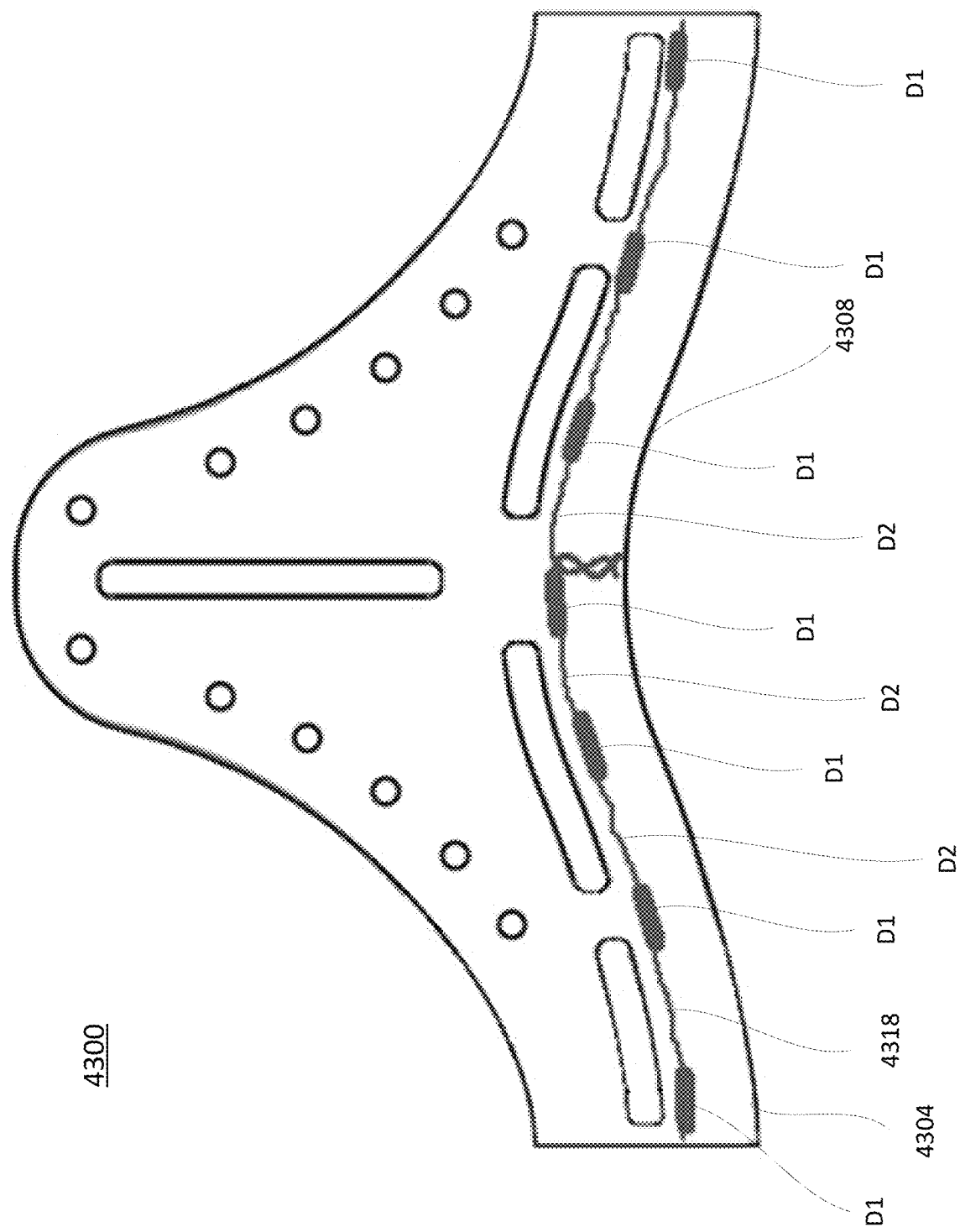
FIG. 28 is a view similar to FIG. 10 according to another embodiment thereof.

In another example system, the diameter of the wire may be changed along its length so that the differing diameters may act as a radiopaque indicator. FIG. 28 illustrates a one-third section of a frame 4300. A single wire 4318 is shown extending along base 4304 of frame 4300 at a position spaced from inflow edge 4308. Wire 4318 has a first diameter D1 and a second diameter D2 that alternate with one another along the length of the wire. Diameter D1 is greater than diameter D2 so as to enable diameter D1 to act as a radiopaque indicator. The number of times the greater diameter D1 appears along the length of the wire may correspond to a surgical valve having a predetermined size. For example, diameter D1 is shown seven times along the illustrated section of frame 4300, which may indicate a specific frame size as dictated by the valve manufacturer.

The enlarged wire diameter D1 may be formed in a variety of ways. In one example, diameter D1 may be formed during the extrusion of the radiopaque wire and may be extruded to have a different diameter than diameter D2. In another example, wire 4318 may be stamped so that a length of the wire has different diameters. Alternatively, diameter D1 may be formed by compressing or pinching along the length of wire 4318 after an initial wire having a uniform diameter D2 has been formed.

Figure 29:
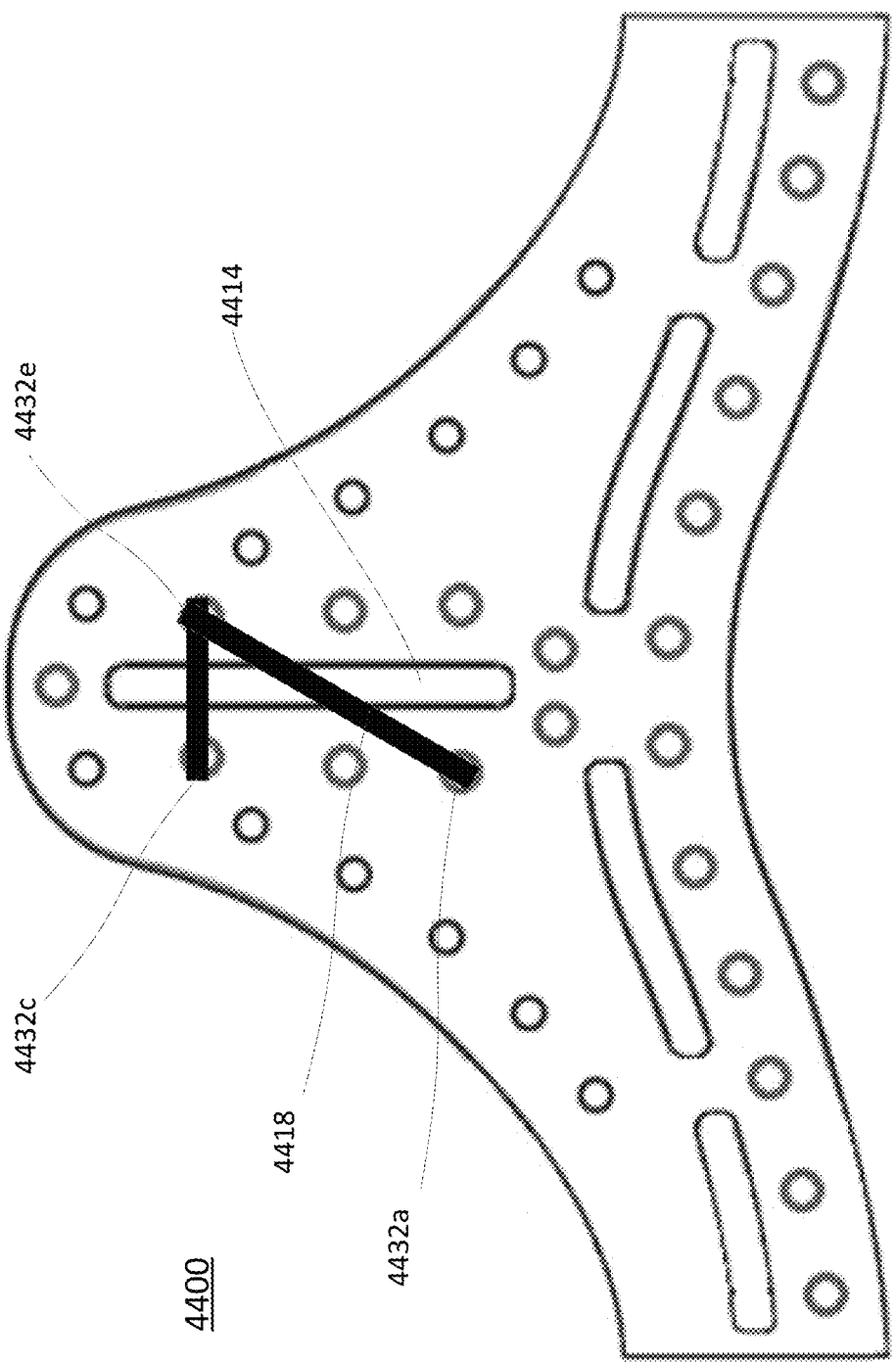
FIG. 29 is a view similar to FIG. 10 according to another embodiment thereof.

Instead of requiring a surgeon to count the number of individual radiopaque elements present on a frame, another system includes providing a radiopaque character directly on the frame to indicate frame size. For example, radiopaque wire or other radiopaque elements may be configured into the shape of any letter, number, or symbol that may be used to directly or indirectly identify the size of a frame. FIG. 29 illustrates an example in which radiopaque wire is configured on frame 4400 into the shape of a specific number corresponding to the size of the frame. As shown, frame 4400 is similar to frame 3100 of FIG. 21, which includes additional apertures along the frame. Wire 4418 may extend through two apertures 4432c and 4432e on directly opposite sides of commissure post slot 4414. Wire 4418 also extends diagonally from aperture 4432e to aperture 4432a. The completed wire creates the number "7". In other examples, any number or symbol may be provided on the frame that ultimately corresponds to the size of the frame, either directly or indirectly. In this example, providing additional apertures around the commissure post slot may provide other options for patterning wire into the shape of a number or other character.

It is to be appreciated that the radiopaque indicators described with regard to FIGS. 25-29 may be implemented on any of the embodiments described herein, including appearing on either or both of the commissure post and base of the frame.

To summarize the foregoing, according to a first aspect of the disclosure, a prosthetic heart valve includes a non-collapsible annular frame extending in a longitudinal direction between an inflow edge and an outflow edge, the frame having a plurality of annularly spaced commissure posts adjacent the outflow edge, each of the commissure posts having a tip and a post slot spaced apart from the tip, a radiopaque element including an elongated main body having a first end and a second end, the radiopaque element extending around the tip and through the post slot of at least one of the commissure posts so that a portion of the main body extends between the post slot and the tip, and a valve assembly connected to the frame and including a plurality of leaflets; and/or the radiopaque element is a metal wire; and/or the first end and the second end of the radiopaque element are intertwined so as to secure the radiopaque element to the tip of the at least one of the commissure posts; and/or the portion of the main body of the radiopaque element overlaps the intertwined first and second ends; and/or the intertwined first and second ends of the radiopaque element overlap the portion of the main body; and/or the intertwined first and second ends are positioned adjacent at least a portion of the main body that extends between the post opening and the tip; and/or the intertwined first and second ends are positioned within the post slot of the at least one of the commissure posts; and/or the radiopaque element is a first radiopaque element and the prosthetic heart valve further comprises a second radiopaque element on a base of the frame adjacent the inflow edge; and/or the second radiopaque element is a radiopaque wire extending at least one revolution around the base of the frame; and/or the radiopaque wire continuously extends a plurality of revolutions around the base of the frame to form a first wire wrap adjacent the inflow edge and a second wire wrap between the first wire wrap and the outflow edge; and/or the radiopaque wire has a first end and a second end, the first end being adjacent the first wire wrap and the second end being adjacent the second wire wrap; and/or the first and second ends of the radiopaque wire are secured to one another; and/or the first and second ends of the radiopaque wire are intertwined; and/or the first and second ends of the radiopaque wire are spaced apart from one another to allow for expansion of the wire; and/or the first and second ends of the radiopaque wire are free ends, the free ends being positioned between the main body and the frame; and/or the second radiopaque element is a radiopaque wire extending at least partially around the base and forming a first wire wrap and a second wire wrap; and/or the radiopaque wire has a first looped end and a second looped end spaced apart from the first looped end, the first looped end being secured to the second looped end by a suture; and/or knots or beads are provided on the wire to identify a characteristic of the prosthetic heat valve; and/or the radiopaque wire has first portions with a first diameter and second portions with a second diameter larger than the first diameter, a number of the second portions indicating the size of the frame; and/or the radiopaque element is a first radiopaque element and the prosthetic heart valve further comprises a second radiopaque element, the second radiopaque element comprising one of a knot, a washer, a bead, or a radiopaque wire; and/or the radiopaque element is a first radiopaque element and the prosthetic heart valve further comprises a second radiopaque element, the second radiopaque element comprising a second wire configured to identify a characteristic of the prosthetic heart valve; and/or wherein the second wire is configured in the shape of a number; and/or wherein the second wire is configured in the shape of a letter or a character; and/or the frame further comprises a plurality of apertures, and wherein the second radiopaque element is a radiopaque wire extending through at least one of the plurality of apertures.

According to a second aspect of the disclosure, a prosthetic heart valve includes a non-collapsible annular frame extending in a longitudinal direction between an inflow edge and an outflow edge, the frame having a plurality of annularly spaced commissure posts adjacent the outflow edge, each of the commissure posts having a tip and a post slot spaced apart from the tip, the frame including a plurality of apertures, a radiopaque wire extending through at least one of the plurality of apertures, and a valve assembly connected to the frame and including a plurality of leaflets; and/or the radiopaque wire includes a plurality of radiopaque wires extending through the at least one of the apertures; and/or the at least one of the apertures includes a first set of apertures and a second set of apertures, each of the apertures in the second set being respectively positioned between an adjacent pair of apertures in the first set, wherein a first end of one of the plurality of radiopaque wires is secured to the frame at a rear of an aperture in the first set of apertures, and a first end of another one of the plurality of wires is secured to the frame at a rear of the aperture in the first set of apertures; and/or the apertures are positioned on at least one of the commissure posts; and/or the post slot on the at least one commissure post is an elongated slot extending in the longitudinal direction, and the apertures are positioned adjacent a periphery of elongated slot; and/or the apertures extend in the longitudinal direction along the at least one commissure post; and/or the at least one of the apertures includes a first set of apertures and a second set of apertures, each of the apertures in the second set being respectively positioned between an adjacent pair of apertures in the first set, wherein a first end of a first wire of the plurality of wires is secured to the frame at a rear of one of the apertures in the first set, and a first end of a second wire of the plurality of wires is secured to the frame at the rear of an the aperture in the second set; and/or the apertures positioned on the at least one commissure post include first apertures and second apertures respectively positioned on opposite sides of the elongated slot, the radiopaque wire extends across the elongated slot from one of the first apertures to one of the second apertures, and a radiopaque element is positioned on a portion of the wire that extends between the one of the first apertures and the one of the second apertures; and/or the radiopaque element is a bead, the wire extending through a portion of the bead; and/or the radiopaque element is a washer, the wire extending through a portion of the washer; and/or a washer is attached to the frame by the radiopaque wire; and/or apertures extend along a base of the frame adjacent the inflow edge; and/or the radiopaque wire includes a plurality of radiopaque wires extending through at least one of the apertures; and/or the at least one aperture includes a first set of apertures and a second set of apertures, each of the apertures in the second set is respectively positioned between an adjacent pair of the apertures in the first set, wherein a first end of a first wire of the plurality of wires is secured to the frame at a rear of one of the apertures in the first set, and a first end of a second wire of the plurality of wires is secured to the frame at the rear of an the aperture in the first set; and/or at least one aperture includes a first set of apertures and a second set of apertures, each of the apertures in the second set is respectively positioned between an adjacent pair of the apertures in the first set, wherein a first end of a first wire of the plurality of wires is secured to the frame at a rear of one of the apertures in the first set, and a first end of a second wire of the plurality of wires is secured to the frame at the rear of an the aperture in the second set; and/or the apertures include post apertures that extend along each of the commissure posts and base apertures that extend around a base of the frame; and/or the wire is a continuous wire that extends through the base apertures and the post apertures; and/or the prosthetic heart valve further comprises one or more radiopaque indicators indicating a characteristic of the prosthetic heart valve, the one or more radiopaque indicators comprising at least one of a washer, a knot, or a bead; and/or the radiopaque wire is a first radiopaque wire and the prosthetic heart valve further comprises a second radiopaque wire extending around the tip and through the post slot.

According to a third aspect of the disclosure, a prosthetic heart valve includes a non-collapsible annular frame extending in a longitudinal direction between an inflow edge and an outflow edge, the frame having an annular base and a plurality of annularly spaced commissure posts adjacent the outflow edge, each of the commissure posts having a tip and a post slot spaced apart from the tip; a radiopaque wire extending a plurality of revolutions around the base so as to form a first wire wrap and a second wire wrap, and a valve assembly connected to the frame and including a plurality of leaflets; and/or the first wire wrap is adjacent the inflow edge and the second wire wrap is positioned between the first wire wrap and the outflow edge; and/or the radiopaque wire extends four revolutions around the base; and/or the first and second wire wraps are directly adjacent one another; and/or the first and second wire wraps are spaced apart from one another; and/or the radiopaque wire has a first end and a second end, the first end being adjacent the first wire wrap and the second end being adjacent the second wire wrap, the first and second ends being intertwined; and/or the radiopaque wire has a first free end and a second free end, the first free end being adjacent the first wire wrap and the second free end being adjacent the second wrap, the first and second free ends being spaced apart from one another; and/or the radiopaque wire forms a third wire wrap extending around the base and overlapping at least portions of the first and second wire wraps; and/or the third wire wrap extends around the base in a sinusoidal pattern; and/or the radiopaque wire extends partially around the base and forms a first wire wrap and a second wire wrap, the radiopaque wire having a first looped end and a second looped end spaced apart from the first looped end, the first looped end being secured to the second looped end by a suture; and/or the prosthetic heart valve further comprises one or more radiopaque indicators indicating a characteristic of the prosthetic heart valve, the one or more radiopaque indicators comprising one of a washer, a knot, or a bead; and/or the radiopaque wire has first portions with a first diameter and second portions with a second diameter larger than the first diameter, a number of the second portions being the one or more radiopaque indicators and indicating the size of the frame; and/or the prosthetic heart valve further comprises a second radiopaque element extending around tip and through the post slot; and/or the frame further comprises a plurality of apertures, and the prosthetic heart valve further comprises another radiopaque element attached to the frame using the plurality of apertures.

According to a fourth aspect of the disclosure, a prosthetic heart valve includes a non-collapsible annular frame extending in a longitudinal direction between an inflow edge and an outflow edge, the frame having an annular base and a plurality of annularly spaced commissure posts adjacent the outflow edge, each of the commissure posts having a tip and a post slot spaced apart from the tip; a radiopaque wire extending at least partially around the base so as to form a first wire wrap and a second wire wrap, and a valve assembly connected to the frame and including a plurality of leaflets; and/or the radiopaque wire extends a plurality of revolutions around the base; and/or the first wire wrap is adjacent the inflow edge and the second wire wrap is positioned between the first wire wrap and the outflow edge; and/or the radiopaque wire extends four revolutions around the base; and/or the first and second wire wraps are directly adjacent one another; and/or the first and second wire wraps are spaced apart from one another; and/or the radiopaque wire has a first end and a second end, the first end being adjacent the first wire wrap and the second end being adjacent the second wire wrap, the first and second ends being intertwined; and/or the radiopaque wire has a first free end and a second free end, the first free end being adjacent the first wire wrap and the second free end being adjacent the second wrap, the first and second free ends being spaced apart from one another; and/or the radiopaque wire forms a third wire wrap extending around the base and overlapping at least portions of the first and second wire wraps; and/or the third wire wrap extends around the base in a sinusoidal pattern; and/or the radiopaque wire extends partially around the base and forms a first wire wrap and a second wire wrap, the radiopaque wire having a first looped end and a second looped end spaced apart from the first looped end, the first looped end being secured to the second looped end by a suture; and/or the radiopaque wire extends partially around the base and forms a first wire wrap and a second wire wrap, the radiopaque wire having a first looped end and a second looped end spaced apart from the first looped end, the first looped end being secured to the second looped end by a suture; and/or the prosthetic heart valve further comprises one or more radiopaque indicators indicating a characteristic of the prosthetic heart valve, the one or more radiopaque indicators comprising one of a washer, a knot, or a bead; and/or the radiopaque wire has first portions with a first diameter and second portions with a second diameter larger than the first diameter, a number of the second portions being the one or more radiopaque indicators and indicating the size of the frame; and/or the prosthetic heart valve further comprises a second radiopaque element extending around tip and through the post slot; and/or the prosthetic heart valve further comprises a plurality of apertures dispose on the frame and a second radiopaque element, and the second radiopaque element is a radiopaque wire extending through at least one of the plurality of apertures.

According to a fifth aspect of the disclosure, a prosthetic heart valve includes a non-collapsible annular frame extending in a longitudinal direction between an inflow edge and an outflow edge, each of the commissure posts having a tip and a post slot spaced apart from the tip, a radiopaque wire extending around a base of the frame with one or more radiopaque indicators indicating a size of the frame, and a valve assembly connected to the frame and including a plurality of leaflets; and/or wherein the radiopaque indicators are knots; and/or wherein the radiopaque indicators are beads; and/or wherein the radiopaque wire has first portions with a first diameter and second portions with a second diameter larger than the first diameter, a number of the second portions comprising the one or more radiopaque indicators and indicating the size of the frame; and/or the frame further comprises a plurality of apertures, and wherein the prosthetic heart valve further comprises a second radiopaque element, the second radiopaque element comprising a radiopaque wire extending through at least one of the plurality of apertures; and/or the frame further comprises a plurality of apertures, and the radiopaque wire extends through at least one of the plurality of apertures; and/or the radiopaque wire is configured in the shape of a number; and/or the radiopaque wire is configured in the shape of a letter or a character.

According to a sixth aspect of the disclosure, a prosthetic heart valve includes a non-collapsible annular frame extending in a longitudinal direction between an inflow edge and an outflow edge, the frame having an annular base and a plurality of annularly spaced commissure posts adjacent the outflow edge, each of the commissure posts having a tip and a post slot spaced apart from the tip; a radiopaque wire extending partially around the base and forming a first wire wrap and a second wire wrap, the radiopaque wire having a first looped end and a second looped end spaced apart from the first looped end, the first looped end being secured to the second looped end by a suture; and a valve assembly connected to the frame and including a plurality of leaflets; and/or the radiopaque wire is a first radiopaque wire, and the prosthetic heart valve further includes a second radiopaque wire having an elongated main body with a first end and a second end, the second radiopaque wire extending around the tip and through the post slot of at least one of the commissure posts so that a portion of the main body extends between the post slot and the tip.

According to a seventh aspect of the disclosure, a prosthetic heart valve includes a non-collapsible annular frame extending in a longitudinal direction between an inflow edge and an outflow edge, the frame having a plurality of annularly spaced commissure posts adjacent the outflow edge, each of the commissure posts having a tip and a post slot spaced apart from the tip; a radiopaque element including an elongated main body having a first end and a second end; and a valve assembly connected to the frame and including a plurality of leaflets; and/or the radiopaque element extends around the tip and through the post slot of at least one of the commissure posts so that a portion of the main body extends between the post slot and the tip; and/or the radiopaque element is a metal wire; and/or the first end and the second end of the radiopaque element are intertwined so as to secure the radiopaque element to the tip of the at least one of the commissure posts; and/or the portion of the main body of the radiopaque element overlaps the intertwined first and second ends; and/or the intertwined first and second ends of the radiopaque element overlap the portion of the main body; and/or the intertwined first and second ends of the radiopaque element are positioned adjacent at least a portion of the main body that extends between the post opening and the tip; and/or the intertwined first and second ends are positioned within the post slot of the at least one of the commissure posts; and/or the radiopaque element is a first radiopaque element and the prosthetic heart valve further comprises a second radiopaque element on a base of the frame adjacent the inflow edge; and/or the second radiopaque element is a radiopaque wire extending at least one revolution around the base of the frame; and/or the frame has an annular base and the radiopaque wire extends at least partially around the base and forms a first wire wrap and a second wire wrap; and/or the radiopaque wire extends a plurality of revolutions around the base, and/or the radiopaque wire extends four revolutions around the base; and/or the radiopaque wire continuously extends a plurality of revolutions around the base of the frame to form a first wire wrap adjacent the inflow edge and a second wire wrap between the first wire wrap and the outflow edge; and/or the radiopaque wire has a first end and a second end, the first end being adjacent the first wire wrap and the second end being adjacent the second wire wrap; and/or the first and second ends of the radiopaque element are secured to one another; and/or the first and second ends of the radiopaque wire are free ends, the free ends being positioned between the main body and the frame; and/or the radiopaque wire has a first looped end and a second looped end spaced apart from the first looped end, the first looped end being secured to the second looped end by a suture; and/or knots or beads are provided on the radiopaque wire to identify a characteristic of the prosthetic heart valve; and/or the radiopaque wire has first portions with a first diameter and second portions with a second diameter larger than the first diameter, a number of the second portions indicating the size of the frame; and/or the radiopaque element is a first radiopaque element and the prosthetic heart valve further comprises a second radiopaque element, the second radiopaque element comprising one of a knot, a washer, a bead, or a second wire; and/or the first wire wrap is adjacent the inflow edge and the second wire wrap is positioned between the first wire wrap and the outflow edge and/or the first and second wire wraps are directly adjacent one another and/or the first and second wire wraps are spaced apart from one another; and/or the radiopaque wire forms a third wire wrap extending around the base and overlapping at least portions of the first and second wire wraps; and/or the radiopaque wire forms a third wire wrap extending around the base and overlapping at least portions of the first and second wire wraps and the third wire wrap extends around the base in a sinusoidal pattern.

It is to be understood that the figures and descriptions of the present disclosure have been simplified to illustrate elements that are relevant for a clear understanding of the present disclosure, while eliminating, for purposes of clarity, many other elements which are conventional in this art. Those of ordinary skill in the art will recognize that other elements may be desirable for implementing the present disclosure.

It is noted that the terminology used above is for the purpose of reference only, and is not intended to be limiting. For example, terms such as "upper," "lower," "above," "below," "rightward," "leftward," "clockwise," and "counterclockwise" refer to directions in the drawings to which reference is made. As another example, terms such as "inward" and "outward" may refer to directions toward and away from, respectively, the geometric center of the component described. As a further example, terms such as "front," "rear," "side," "left side," "right side," "top," "bottom," "inner," "outer," "horizontal," and "vertical" describe the orientation of portions of the component within a consistent but arbitrary frame of reference which is made clear by reference to the text and the associated drawings describing the component under discussion. Such terminology will include the words specifically mentioned above, derivatives thereof, and words of similar import.

While the embodiments disclosed herein have been described in detail, it is evident that many alternatives, modifications, and variations will be apparent to those skilled in the art. Indeed, the disclosure set forth herein includes all possible combinations of the particular features set forth above, whether specifically described herein or not. For example, where a particular feature is described in the context of a particular aspect, arrangement, configuration, or embodiment, that feature may also be used, to the extent possible, in combination with and/or in the context of other particular aspects, arrangements, configurations, and embodiments. Moreover, the disclosure set forth herein includes the mirror image, i.e., mirror configuration, taken from any perspective of any drawing or other configuration shown or described herein. Accordingly, aspects of the disclosure as set forth above are intended to be illustrative, not limiting. Various changes may be made without departing from the spirit and scope of the subject matter as defined in the following claims.

The invention claimed is:

1. A prosthetic heart valve, comprising:
a non-collapsible annular frame extending in a longitudinal direction between an inflow edge and an outflow edge, the frame having an annular base adjacent the inflow edge and a plurality of annularly spaced commissure posts adjacent the outflow edge, each of the commissure posts having a tip and a post slot within the commissure post and spaced apart from the tip;
a radiopaque wire extending partially around the base so as to form a first wire wrap and a second wire wrap, the first wire wrap being connected to the second wire wrap at a first looped end and at a second looped end spaced apart from the first looped end, the first looped end being secured to the second looped end by a suture; and
a valve assembly connected to the frame and including a plurality of leaflets connected to the commissure posts.

2. The prosthetic heart valve of claim 1, wherein the first wire wrap is adjacent the inflow edge and the second wire wrap is positioned between the first wire wrap and the outflow edge.

3. The prosthetic heart valve of claim 1, wherein the prosthetic heart valve further comprises one or more radiopaque indicators indicating a characteristic of the prosthetic heart valve, the one or more radiopaque indicators comprising one of a washer, a knot, or a bead.

4. The prosthetic heart valve of claim 1, further comprising a radiopaque element including an elongated main body having a free first end and a free second end, the radiopaque element extending around the tip and through the post slot of at least one of the commissure posts so that a portion of the main body extends between the post slot and the tip.

5. The prosthetic heart valve of claim 4, wherein the first end and the second end of the radiopaque element are tucked beneath the portion of the main body such that the first end and the second end of the radiopaque element are positioned between the portion of the main body and a surface of the at least one commissure post and the first end is not directly connected to the second end.

6. The prosthetic heart valve of claim 4, wherein the radiopaque element is a metal wire.

7. The prosthetic heart valve of claim 4, wherein the first end and the second end of the radiopaque element are intertwined to secure the radiopaque element to the tip of the at least one of the commissure posts.

8. The prosthetic heart valve as claimed in claim 7, wherein the portion of the main body of the radiopaque element overlaps the intertwined first and second ends.

9. The prosthetic heart valve of claim 7, wherein the intertwined first and second ends are positioned within the post slot of the at least one of the commissure posts.

10. The prosthetic heart valve of claim 1, further comprising a plurality of apertures along at least one of the post slots, and a radiopaque wire extending through at least one of the apertures.

11. The prosthetic heart valve of claim 10, wherein the radiopaque wire extends through a multiplicity of the apertures.

12. The prosthetic heart valve of claim 10, wherein the radiopaque wire extends through each of the apertures.

13. The prosthetic heart valve as claimed in claim 1, wherein the radiopaque wire extends partially around the base to form first, second third and fourth wire wraps, the first, second, third and fourth wire wraps being connected to one another to form the first looped end and the second looped end.

* * * * *